(12) United States Patent
Li et al.

(10) Patent No.: US 7,709,625 B2
(45) Date of Patent: May 4, 2010

(54) METHODS AND COMPOSITIONS FOR BONE MARROW STEM CELL-DERIVED MACROPHAGE DELIVERY OF GENES FOR GENE THERAPY

(75) Inventors: Senlin Li, San Antonio, TX (US); Robert A. Clark, San Antonio, TX (US)

(73) Assignee: The Board of Regents of the University of Texas, Austin, TX (US)

( * ) Notice: Subject to any disclaimer, the term of this patent is extended or adjusted under 35 U.S.C. 154(b) by 436 days.

(21) Appl. No.: 11/199,465

(22) Filed: Aug. 8, 2005

(65) Prior Publication Data

US 2006/0018889 A1 Jan. 26, 2006

Related U.S. Application Data

(63) Continuation-in-part of application No. 11/150,660, filed on Jun. 10, 2005, now abandoned.

(60) Provisional application No. 60/578,646, filed on Jun. 10, 2004.

(51) Int. Cl.
*C07H 21/04* (2006.01)
*C12N 15/63* (2006.01)
*C12N 15/00* (2006.01)
*C12N 5/00* (2006.01)
*C12Q 1/68* (2006.01)

(52) U.S. Cl. .................. 536/24.1; 435/455; 435/320.1; 435/325

(58) Field of Classification Search ........................ None
See application file for complete search history.

(56) References Cited

U.S. PATENT DOCUMENTS 5,502,176 A * 3/1996 Tenen et al. ................. 536/24.1
7,183,395 B2 * 2/2007 Mauro et al. ................ 536/23.1
2005/0227246 A1 * 10/2005 Hahm .......................... 435/6

OTHER PUBLICATIONS

Aiello et al. "Increased Atherosclerosis in Hyperlipidemic Mice With Inactivation of ABCA1 in Macrophages" *Arterioscler Thromb Vasc Biol.* 22:630-637 (2002).
Aiuti et al. "Correction of ADA-SCID by Stem Cell Gene Therapy Combined with Nonmyeloablative Conditioning" *Science* 296(5577):2410-2413 (2002).
Akerud et al. "Persephin-Overexpressing Neural Stem Cells Regulate the Function of Nigral Dopaminergic Neurons and Prevent Their Degeneration in a Model of Parkinson's Disease" *Molecular and Cellular Neuroscience* 21:205-222 (2002).
Akerud et al. "Neuroprotection through Delivery of Glial Cell Line-Derived Neurotrophic Factor by Neural Stem Cells in a Mouse Model of Parkinson's Disease" *The Journal of Neuroscience* 21(20):8108-8118 (2001).
Arenas "Stem cells in the treatment of Parkinson's disease" *Brain Research Bulletin* 57(6):795-808 (2002).
Arnold et al. "Hydrogen peroxide mediates the cell growth and transformation caused by the mitogenic oxidase Nox1" *PNAS* 98(10):5550-5555 (2001).
Babaev et al. "Reduced Atherosclerotic Lesions in Mice Deficient for Total or Macrophage-Specific Expression of Scavenger Receptor-A" *Arterioscler Thromb Vasc Biol.* 20:2593-2599 (2000).
Back et al. "Leukocyte Integrin CD11b Promoter Directs Expression in Lymphocytes and Granulocytes in Transgenic Mice" *Blood* 85(4):1017-1024 (1995).
Banfi et al. "Two Novel Proteins Activate Superoxide Generation by the NADPH Oxidase NOX1" *The Journal of Biological Chemistry* 278(6):3510-3513 (2003).
Biffi et al. "Correction of metachromatic leukodystrophy in the mouse model by transplantation of genetically modified hematopoietic stem cells" *The Journal of Clinical Investigation* 113(8):1118-1129 (2004).
Biffi et al. "Gene therapy of metachromatic leukodystrophy reverses neurological damage and deficits in mice" *The Journal of Clinical Investigation* 116(11):3070-3082 (2006).
Bjorgvinsdottir et al. "Retroviral-Mediated Gene Transfer of $gp91^{phox}$ Into Bone Marrow Cells Rescues Defect in Host Defense Against *Aspergillus fumigatus* in Murine X-Linked Chronic Granulomatous Disease" *Blood* 89(1):41-48 (1997).
Boring et al. "Decreased lesion formation in $CCR2^{-/-}$ mice reveals a role for chemokines in the initiation of atherosclerosis" *Nature* 394:894-897 (1998).
Brenner et al. "Current developments in the design of onco-retrovirus and lentivirus vector systems for hematopoietic cell gene therapy" *Biochimica et Biophysica Acta* 1640:1-24 (2003).
Burke et al. "Macrophages in gene therapy: cellular delivery vehicles and in vivo targets" *Journal of Leukocyte Biology* 72:417-428 (2002).
Cavazzana-Calvo et al. "Gene Therapy of Human Severe Combined Immunodeficiency (SCID)-X1 Disease" *Science* 288:669-672 (2000).
Chawla et al. "A PPARγ-LXR-ABCA1 Pathway in Macrophages Is Involved in Cholesterol Efflux and Atherogenesis" *Molecular Cell* 7:161-171 (2001).

(Continued)

*Primary Examiner*—Quang Nguyen
(74) *Attorney, Agent, or Firm*—Myers Bigel Sibley & Sajovec P.A.

(57) ABSTRACT

The present invention provides an isolated nucleic acid comprising a promoter operably linked to a nucleic acid encoding a peptide or protein and/or an RNA (e.g., antisense or ribozyme), wherein the promoter comprises elements that can include, but are not limited to, a) a myeloid specific promoter element comprising a core sequence GAGGAA; b) a myeloid specific promoter element comprising a core sequence AAGGAGAAG; c) a myeloid specific promoter element comprising a core sequence TTTCCAAA; d) a myeloid specific promoter element comprising a core sequence TGTGGTTGC; e) a myeloid specific promoter element comprising a core sequence TGAGTCA; f) a myeloid associated promoter element comprising a core sequence CCGCCC; and g) any combination of (a), (b), (c), (d), (e) and/or (f), any combination of multiples of (a), (b), (c), (d), (e) and/or (f), in any order and/or in any orientation (forward or reverse).

21 Claims, 3 Drawing Sheets

OTHER PUBLICATIONS

Choi-Lundberg et al. "Dopamingeric neurons protected from degeneration by GDNF gene therapy" *Science* 275:838-841 (1997).

Clark et al. "NADPH Oxidase of Human Neutrophils" *The Journal of Biological Chemistry* 262(9):4065-4074 (1987).

Clarke et al. "Myeloid-specific gene expression" *Journal of Leukocyte Biology* 63:153-168 (1998).

Cunningham et al. "Astrocyte Delivery of Glial Cell Line-Derived Neurotrophic Factor in a Mouse Model of Parkinson's Disease" *Experimental Neurology* 174:230-242 (2002).

Cybulsky et al. "A major rule for VCAM-1, but not ICAM-1, in early atherosclerosis" *The Journal of Clinical Investigation* 107(10):1255-1262 (2001).

Dinauer et al. "Long-term Correction of Phagocyte NADPH Oxidase Activity by Retroviral-Mediated Gene Transfer in Murine X-Linked Chronic Granulomatous Disease" *Blood* 94(3):914-922 (1999).

Dinauer et al. "Variable correction of host defense following gene transfer and bone marrow transplantation in murine X-linked chronic granulomatous disease" *Blood* 97(12):3738-3745 (2001).

Dziennis et al. "The CD11b Promoter Directs High-Level Expression of Reporter Genes in Macrophages in Transgenic Mice" *Blood* 85(2):319-329 (1995).

Emerich et al. "Implants of Encapsulated Human CNTF-Producing Fibroblasts Prevent Behavioral Deficits and Striatal Degeneration in a Rodent Model of Huntington's Disease" *The Journal of Neuroscience* 16(16):5168-5181 (1996).

Emerich et al. "Protective effect of encapsulated cells producing neurotrophic factor CNTF in a monkey model of Huntington's disease" *Nature* 386:395-399 (1997).

Fazio et al. "Increased atherosclerosis in mice reconstituted with apolipoprotein E null macrophages" *Proc. Natl. Acad. Sci. USA* 94:4647-4652 (1997).

Gill et al. "Direct brain infusion of glial cell line-derived neurotrophic factor in Parkinson disease" *Nature Medicine* 9(5):589-595 (2003).

Goebel et al. "Retroviral-Mediated Gene Transfer and Nonmyeloablative Conditioning: Studies in a Murine X-Linked Chronic Granulomatous Disease Model" *Journal of Pediatric Hematology/Oncology* 249(9):787-790 (2002).

Grondin et al. "Glial cell line-derived neurotrophic factor (GDNF): a drug candidate for the treatment of Parkinson's disease" *J Neurol.* 245:35-42 (1998).

Grefhorst et al. "Stimulation of Lipogenesis by Pharmacological Activation of the Liver X Receptor Leads to Production of Large, Triglyceride-rich Very Low Density Lipoprotein Particles" *The Journal of Biological Chemistry* 277(37):34182-34190 (2002).

Hacein-Bey-Abina et al. "A Serious Adverse Event after Successful Gene Therapy for X-linked Severe Combined Immunodeficiency" *The New England Journal of Medicine* 348(3):255-256 (2003).

Hacein-Bey-Abina et al. "Sustained Correction of X-Linked Severe Combined Immunodeficiency by Ex Vivo Gene Therapy" *The New England Journal of Medicine* 349(16):1185-1195 (2002).

Hahn et al. "Correction of murine galactosialidosis by bone marrow-derived macrophages overexpressing human protective protein/cathepsin A under control of the colony-stimulating factor-1 receptor promoter" *Proc. Natl. Acad. Sci. USA* 95:14880-14885 (1998).

Hasty et al. "Retroviral Gene Therapy in ApoE-Deficient Mice ApoE Expression in the Artery Wall Reduces Early Foam Cell Lesion Formation" *Circulation* 99:2571-2576 (1999).

He et al. "Development of a Synthetic Promoter for Macrophage Gene Therapy" *Human Gene Therapy* 17:949-959 (2006).

Ho et al. "Induction of Interleukin-1 Associated with Compensatory Dopaminergic Sprouting in the Denervated Striatum of Young Mice: Model of Aging and Neurodegenerative Disease" *The Journal of Neuroscience* 18(15):5614-5629 (1998).

Horwitz et al. "Treatment of Chronic Granulomatous Disease with Nonmyeloablative Conditioning and a T-Cell-Depleted Hematopoietic Allograft" *New England Journal of Medicine* 344(12):881-888 (2001).

Imren et al. "Permanent and panerythroid correction of murine β thalassemia by multiple lentiviral integration in hematopoietic stem cells" *PNAS* 99(22):14380-14385 (2002).

Jackson et al. "The $p47^{phox}$ Mouse Knock-Out Model of Chronic Granulomatous Disease" *The Journal of Experimental Medicine* 182:751-758 (1995).

Kennedy et al. "Kinetics of Central Nervous System Microglial and Macrophage Engraftment: Analysis Using a Transgenic Bone Marrow Transplantation Model" *Blood* 90(3):986-993 (1997).

Kondo et al. "Biology of Hematopoietic Stem Cells and Progenitors: Implications for Clinical Application" *Annu. Rev. Immunol.* 21:759-806 (2003).

Kordower et al. "Neurodegeneration Prevented by Lentiviral Vector Delivery of GDNF in Primate Models of Parkinson's Disease" *Science* 290:767-773 (2000).

Kordower et al. "In Vivo Delivery of Glial Cell Line-Derived Neurotrophic Factor for Parkinson's Disease" *Ann Neurol* 53:S120-S134 (2003).

Kume et al. "Gene therapy for chronic granulomatous disease" *J Lab Clin Med* 135:122-128 (2000).

Leimig et al. "Functional amelioration of murine galactosialidosis by genetically modified bone marrow hematopoietic progenitor cells" *Blood* 99(9):3169-3178 (2002).

Li et al. "Transcriptional Regulation of the $p67^{phox}$ Gene" *The Journal of Biological Chemistry* 276(42):39368-39378 (2001).

Li et al. "PU.1 Is Essential for $p47^{phox}$ Promoter Activity in Myeloid Cells" *The Journal of Biological Chemistry* 272(28):17802-17809 (1997).

Li et al. "Multiple PU.1 sites cooperate in the regulation of $p40^{phox}$ transcription during granulocyte differentiation of myeloid cells" *Blood* 99(12):4578-4587 (2002).

Li et al. "Critical Flanking Sequences of PU.1 Binding Sites in Myeloid-specific Promoters" *The Journal of Biological Chemistry* 274(45):32453-32460 (1999).

Li et al. "Synthetic muscle promoters: activities exceeding naturally occurring regulatory sequences" *Nature Biotechnology* 17:241-245 (1999).

Okazaki et al. "Elimination of Cholesterol Ester from Macrophage Foam Cells by Adenovirus-mediated Gene Transfer of Hormone-sensitive Lipase" *The Journal of Biological Chemistry* 277(35):31893-31899 (2002).

Pawliuk et al. "Correction of Sickle Cell Disease in Transgenic Mouse Models by Gene Therapy" *Science* 294:2368-2371 (2001).

Phillips et al. "The challenge of gene therapy and DNA delivery" *Journal of Pharmacy and Pharmacology* 53:1169-1174 (2001).

Priller et al. "Targeting gene-modified hematopoietic cells to the central nervous system: Use of green fluorescent protein uncovers microglial engraftment" *Nature Medicine* 7(12):1356-1361 (2001).

Qiao et al. "Increased Expression of Glutathione Reductase in Macrophages Decreases Atherosclerotic Lesion Formation in Low-Density Lipoprotein Receptor-Deficient Mice" *Arterioscler Thromb Vasc Biol.* 27:1375-1382 (2007).

Roesler et al. "Third-generation, self-inactivating $gp91^{phox}$ lentivector corrects the oxidase defect in NOD/SCID mouse-repopulating peripheral blood-mobilized $CD34^+$ cells from patients with X-linked chronic granulomatous disease" *Blood* 100(13):4381-4390 (2002).

Tahara-Hanaoka et al. "Lentiviral vector-mediated transduction of murine CD34 hematopoietic stem cells" *Experimental Hematology* 20:11-17 (2002).

Tenen et al. "Transcription Factors, Normal Myeloid Development, and Leukemia" *Blood* 90:489-519, 1997.

Vigna et al. "Robust and Efficient Regulation of Transgene Expression in Vivo by Improved Tetracycline-Dependent Lentiviral Vectors" *Molecular Therapy* 5(3):252-261 (2002).

Wang et al. "Delayed delivery of AAV-GDNF prevents nigral neurodegeneration and promotes functional recovery in a rat model of Parkinson's disease" *Gene Therapy* 9:381-389 (2002).

Woods et al. "Development of gene therapy for hematopoietic stem cells using lentiviral vectors" *Leukemia* 16:563-569 (2002).

Wu et al. "Distribution and Characterization of GFP+ Donor Hematogenous Cells in Twitcher Mice after Bone Marrow Transplantation" *American Journal of Pathology* 156(6)1849-1854 (2000).

Wu et al. Transcription Start Regions in the Human Genome Are Favored Targets for MLV Integration *Science* 300:1749-1751 (2003).

Yam et al. "Design of HIV Vectors for Efficient Gene Delivery into Human Hematopoietic Cells" *Molecular Therapy* 5(4):479-484 (2002).

* cited by examiner

METHODS AND COMPOSITIONS FOR BONE MARROW STEM CELL-DERIVED MACROPHAGE DELIVERY OF GENES FOR GENE THERAPY

STATEMENT OF PRIORITY

This application is a continuation-in-part of, and claims priority to, U.S. application Ser. No. 11/150,660, filed Jun. 10, 2005, now abandoned which claims the benefit, under 35 U.S.C. § 119(e), of U.S. Provisional Application No. 60/578,646, filed Jun. 10, 2004, the entire contents of each of which are incorporated herein by reference.

STATEMENT OF GOVERNMENT SUPPORT

Studies described herein were supported in part by NIAID Grant No. RO1A12086. The Government has certain rights in this invention.

FIELD OF THE INVENTION

The present invention is directed to compositions and methods of their use in the treatment of various disorders by delivery of therapeutic proteins and peptides to treatment sites via myeloid cells.

BACKGROUND OF THE INVENTION

Neurodegenerative diseases, such as Alzheimer's disease (AD), Parkinson's disease (PD), and lysosomal storage disorders (LSD), affect a large population of patients. For example, PD has a prevalence of 1-2% in people over the age of 50, worldwide distribution, and no gender preference (Kordower and Aebischer, 2001). The common hallmark of neurodegenerative diseases is the selective loss of neurons in different brain regions and in the spinal cord (Djaldetti and Melamed, 2001). PD is characterized by the progressive loss of dopaminergic neurons in the substantia nigra (SN), resulting in resting tremor, rigidity, bradykinesia, and postural imbalance (Goetz et al., 1989). Despite many years of focused research, the causes of this disease remain to be elucidated (Steece-Collier et al., 2002). Levodopa and other dopaminergic medications significantly improve the motor symptoms and quality of life of patients with PD in the early stages of the disease. L-Dopa is most successful during the first few years of treatment, and this period is known as the L-dopa honeymoon. However, once the honeymoon period has waned, patients become progressively more disabled, despite an ever more complex combination of available anti-Parkinsonian treatments (Goetz et al., 1989). Sooner or later, they suffer from dopa-resistant motor symptoms (speech impairment, abnormal posture, gait and balance problems), dopa-resistant non-motor signs (autonomic dysfunction, mood and cognitive impairment, sleep problems, pain) and/or drug-related side effects (especially psychosis, motor fluctuations, and dyskinesias) (Rascol et al., 2003). To fill this therapeutic gap, pallidotomy, deep-brain stimulation, and transplantation of fetal midbrain dopamine-producing neurons have been developed. Nevertheless, the current status of PD treatment cannot be considered as ideal with regard to either efficacy or safety (Djaldetti and Melamed, 2001; Du et al., 2001; Shastry, 2001), although it is favorable as compared with other neurodegenerative disorders such as Alzheimer's disease, Huntington's disease, and amyotrophic lateral sclerosis (Deglon and Aebischer, 2002).

Chronic granulomatous disease (CGD) is an inherited disorder of host defense, in which the generation of superoxide and derivative microbicidal oxidants by the NADPH oxidase in phagocytic leukocytes is absent or markedly deficient due to mutations in oxidase subunit $gp91^{phox}$, $p47^{phox}$, or others. Victims suffer from recurrent and often life-threatening bacterial and fungal infections beginning in early childhood. Chronic inflammatory granulomas, a hallmark of CGD, can obstruct internal organs such as ureter and bowel. Although daily administration of prophylactic antibiotics plus interferon-γ decreases the frequency of infection and allogeneic bone marrow transplantation from HLA-identical donors cures selected patients, the mortality rates are still 2-4% annually. Because CGD results from specific gene defects in hematopoietic stem cells (HSCs), and mouse models that recapitulate the human disease have been developed, CGD has become an attractive target disorder for gene therapy.

Atherosclerosis is the leading cause of mortality in developed countries, accounting for nearly 50% of all deaths. Common risk factors include high cholesterol, diabetes, hypertension, smoking, obesity, and a familial predisposition. Interventions targeting these factors have had limited effects. HMG CoA reductase inhibitors (statins), a potent class of cholesterol-lowering drugs, have been proven to reduce cardiovascular mortality in hypercholesterolemic patients. Percutaneous and surgical treatments are aimed at either disrupting or bypassing flow-limiting lesions. Stem cell and gene therapy holds great promise, but is in its infancy[1].

Atherosclerosis is a disorder of lipid metabolism, as well as a chronic inflammatory disease. Macrophages, participating in both lipid metabolism and inflammation, have key roles in all phases of atherosclerosis, from development of the fatty streak to processes that ultimately contribute to plaque rupture and MI. Macrophage expression of a number of genes may protect against atherosclerosis and inadequate expression or lack of expression of these genes leads to atherogenesis. They are apoE, apoAI, ABCA1, HSL, LXR, and PPARγ, among others. On the other hand, some genes expressed in macrophages are involved in atherogenesis, such as CCR2, MCP-1, CCR5, MCSF, COX-2, 12/15-LO, and macrophage fatty-acid-binding protein aP2. There are a number of genes that can be manipulated in macrophages to benefit patients with atherosclerosis. For instance, apoE, apoAI, ABCA1 (ATP-binding cassette transporter A1), and LXRs (liver X receptors) are among genes to be over-expressed, whereas CCR2, 12/15-lipoxygenase, and macrophage fatty-acid-binding protein aP2 are candidate genes to be knocked down by the powerful RNAi technique.

Many viral promoters, such as CMV, show strong promoter activity, but are generally non-selective, acting in a wide variety of cell types. Lacking cell specificity, they may drive inappropriate gene expression in non-target tissues and cells causing additional problems for the recipient. Furthermore, it was reported that the level of $gp91^{phox}$ expression resulting from transduction with a CMV-driven lentivector was probably inadequate for clinical application[36]. On the other hand, native promoters are either too long to incorporate into the vector used or too weak to drive transgene expression effectively. In studies on roles of interactions between transcription factors and cis-elements in gene regulation, tandem repetitive cis-elements have been successfully used to amplify function. Repetitive regulatory elements are also engineered into other types of constructs. In the tetracycline-regulated system, expression of the gene of interest is controlled by a promoter that contains seven tetracycline response elements (TRE)[37,37,38]. Recently, synthetic muscle promoters have been developed with activity exceeding naturally occurring promoter sequences[39]. Random assembly of E-box, MEF-2, TEF-1, and SRE sites into synthetic promoter recombinant libraries led to the isolation of several artificial promoters whose transcriptional potencies greatly exceed those of natural myogenic and viral gene promoters[39,40].

The present invention overcomes previous shortcomings in the treatment of various disorders such as the ones described above by providing methods and compositions whereby macrophages are engineered to selectively express therapeutic nucleic acids under the control of super macrophage promoters to deliver therapeutic peptides and proteins to the site of disease lesions.

SUMMARY OF THE INVENTION

The present invention provides an isolated nucleic acid comprising a promoter operably linked to a nucleic acid encoding a peptide or protein of interest, wherein the promoter comprises elements selected from the group consisting of: a) myeloid specific promoter element PU.1A; b) myeloid specific promoter element PU.1B; c) myeloid specific promoter element C/EBPα; d) myeloid specific promoter element AML-1; e) myeloid associated promoter element Sp1; f) myeloid associated promoter element AP-1; and g) any combination of (a), (b), (c), (d), (e) and/or (f), in any combination of multiples of (a), (b), (c), (d), (e) and/or (f), in any order and in any orientation (forward or reverse).

Additionally provided herein is a method of producing a cell of this invention, comprising transducing the cell with a vector and/or nucleic acid of this invention.

The present invention still further provides a method of treating a disorder, which can be, but is not limited to, Parkinson's disease, Alzheimer's disease, Huntington's disease, amyotrophic lateral sclerosis (ALS, also known as Lou Gerhig's disease), chronic granulomatous disease, other neurodegenerative diseases and atherosclerosis, in a subject, comprising administering to the subject an effective amount of a cell of this invention to the subject.

Also provided herein is a method of producing a macrophage comprising a nucleic acid of this invention, comprising transducing a hematopoietic stem cell with a viral (e.g., lentiviral) vector comprising the nucleic acid and maintaining the hematopoietic stem cell under conditions whereby it differentiates into the macrophage.

In yet other embodiments, the present invention provides a method of treating a disorder, which can be, but is not limited to, Parkinson's disease, Alzheimer's disease, amytrophic lateral sclerosis (ALS, AKA Lou Gerhig's disease), chronic granulomatous disease, other neurodegenerative diseases and atherosclerosis, comprising: a) transducing a hematopoietic stem cell of the subject with a viral vector comprising a nucleic acid of this invention; and b) delivering the hematopoietic stem cell to the subject.

The present invention further provides a method of identifying a nucleic acid having promoter activity that is greater in myeloid cells than the promoter activity of a CMV promoter, a CSF-1R promoter and/or a CD11b promoter, comprising:

a) producing a nucleic acid comprising a promoter operably linked to a nucleic acid encoding a peptide or protein, wherein the promoter comprises elements selected from the group consisting of: a) myeloid specific promoter element PU.1A; b) myeloid specific promoter element PU.1B; c) myeloid specific promoter element C/EBPα; d) myeloid specific promoter element AML-1; e) myeloid associated promoter element Sp1; f) myeloid associated promoter element AP-1; and g) any combination of (a), (b), (c), (d), (e) and/or (f), any combination of multiples of (a), (b), (c), (d), (e) and/or (f), in any order and in any orientation (forward or reverse); and b) comparing the promoter activity of the nucleic acid of step (a) in myeloid cells with the promoter activity of a CMV promoter, a CSF-1R promoter or a CD11b promoter in myeloid cells, wherein a nucleic acid having activity in myeloid cells that is greater than the promoter activity in myeloid cells of a CMV promoter, a CSF-1R promoter and/or a CD11b promoter is identified as a nucleic acid having promoter activity that is greater in myeloid cells than the promoter activity of a CMV promoter, a CSF-1R promoter or a CD11b promoter. This method of identifying such nucleic acids can be carried out in vitro and/or in vivo according to protocols well known in the art for measuring promoter activity and as described in the Examples herein.

Further provided is a method of producing a nucleic acid comprising a promoter operably linked to a nucleic acid encoding a peptide or protein, wherein the promoter comprises elements selected from the group consisting of: a) myeloid specific promoter element PU.1A; b) myeloid specific promoter element PU.1B; c) myeloid specific promoter element C/EBPα; d) myeloid specific promoter element AML-1; e) myeloid associated promoter element Sp1; f) myeloid associated promoter element AP-1; and g) any combination of (a), (b), (c), (d), (e) and/or (f), any combination of multiples of (a), (b), (c), (d), (e) and/or (f), in any order and in any orientation (forward or reverse), comprising:

1) producing each element (a) through (f) according to protocols as described herein;

2) combining each element under conditions whereby random ligation can occur; and 3) separating each resulting nucleic acid comprising the elements.

In additional embodiments, the present invention provides a promoter comprising, consisting essentially of and/or consisting of the following elements: [C/EBPa forward]-[AM L-1 forward]-[PU.1A reverse]-[PU.1B reverse]-[PU.1A reverse]-[AM L-1 reverse]-[C/EBPa reverse]-[C/EBPa forward]-[AM L-1 forward] [PU.1B reverse] [PU.1A forward]-[Sp1 forward]-[Sp1 forward] [C/EBPa forward]-[AM L-1 forward] (SP-30).

Furthermore, the present invention provides a promoter comprising, consisting essentially of and/or consisting of the following elements: [Sp1 reverse]-[C/EBPa forward]-[AM L-1 forward]-[C/EBPa forward]-[AM L-1 forward]-[C/EBPa forward]-[AM L-1 forward]-[Sp1 forward]-[PU.1A forward] (SP-60).

Also provided herein is a promoter comprising, consisting essentially of and/or consisting of the following elements: [PU.1A forward]-[PU.1B reverse]-[C/EBPa forward]-[AM L-1 forward]-[PU.1A forward]-[PU.1A forward]-[PU.1B reverse]-[PU.1B forward]-[C/EBPa forward]-[AM L-1 forward]-[PU.1B forward]-[PU.1B reverse]-[PU.1A reverse] (SP-107).

In other embodiments, the present invention provides a promoter comprising, consisting essentially of and/or consisting of the following elements: [PU.1B reverse]-[Sp1 forward]-[AM L-1 reverse]-[C/EBPa reverse]-[PU.1A forward]-[PU.1B reverse]-[AP1 forward]-[PU.1B forward]-[AM L-1 reverse]-[C/EBPa reverse]-[AP1 reverse]-[AM L-1 reverse]-[C/EBPa reverse]-[PU.1A forward]-[Sp1 reverse]-[PU.1B forward]-[AM L-1 reverse]-[C/EBPa reverse]-[PU.1B forward]-[C/EBPa forward]-[AM L-1 forward]-[PU.1B forward]-[Sp1 reverse]-[Sp1 reverse]-[AM L-1 reverse]-[C/EBPa reverse]-[PU.1B forward] (SP-144).

The present invention further provides a promoter comprising, consisting essentially of and/or consisting of the following elements: [PU.1B reverse]-[C/EBPa forward]-[AM L-1 forward]-[C/EBPa forward]-[AM L-1 forward]-[PU.1B reverse]-[PU.1A forward]-[PU.1A forward]-[Sp1 reverse]-[AM L-1 reverse]-[C/EBPa reverse]-[PU.1A forward]-[PU.1B reverse]-[PU.1A forward] (SP-146).

Various other objectives and advantages of the present invention will become apparent from the following detailed description.

DETAILED DESCRIPTION OF THE INVENTION

Figure 1:
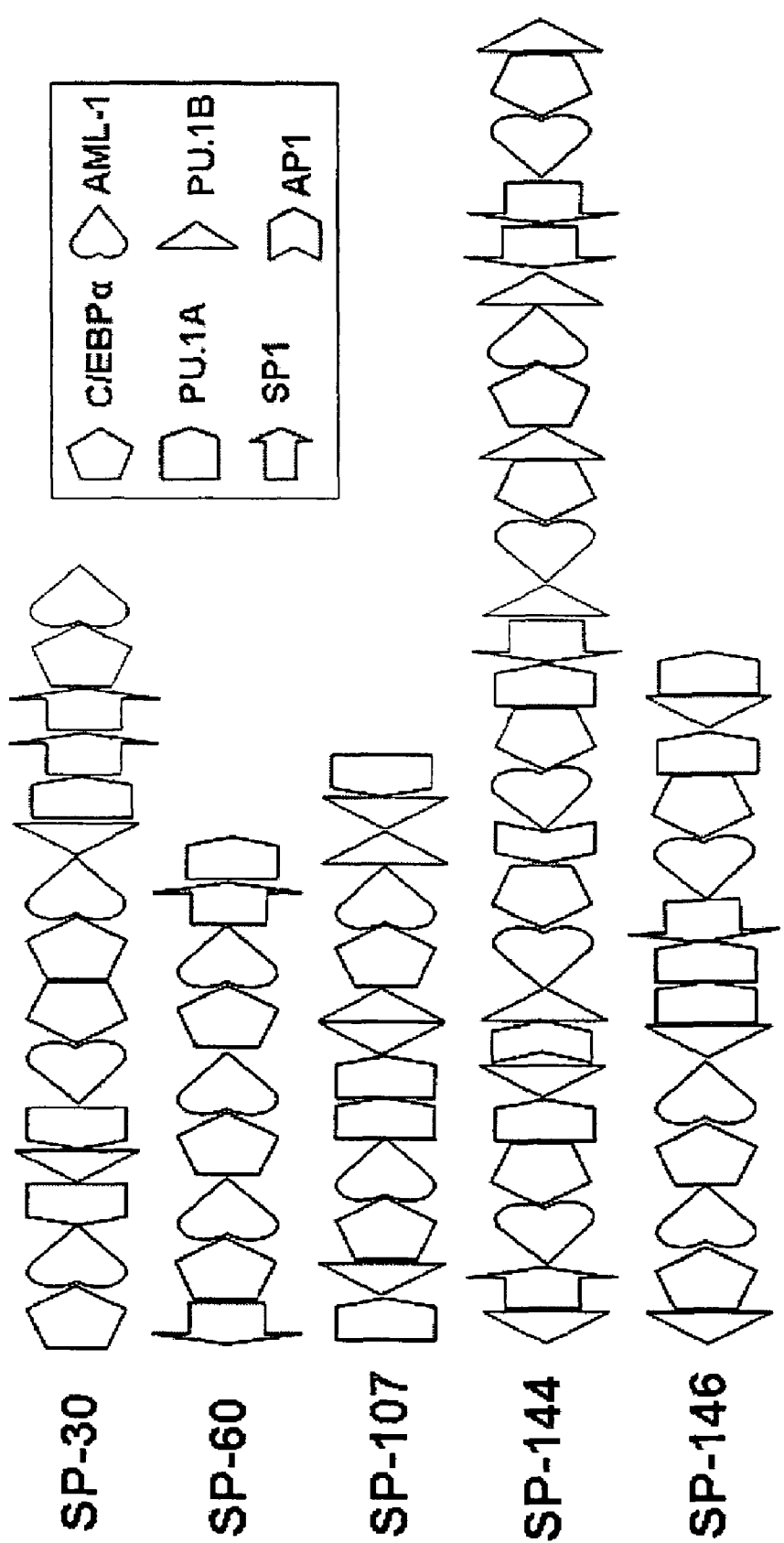
FIG. 1. Design and sequence of synthetic promoters. Synthetic promoter elements in the constructs with the highest in vitro reporter gene activity relative to the basal control pGL3-P47-86.

As used herein, "a" or "an" or "the" can mean one or more than one. For example, "a" cell can mean one cell or a plurality of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The present invention is directed to the unexpected discovery that macrophages, engineered to express high levels of a therapeutic nucleic acid under the direction of a "super macrophage promoter" (SMP), can be used to deliver the therapeutic product encoded by the nucleic acid to a treatment site in a subject. In particular, the SMP carried by the macrophage is designed and selected to express the therapeutic nucleic acid in high yield specifically from the macrophage.

Thus, in one embodiment, the present invention provides an isolated nucleic acid comprising, consisting essentially of and/or consisting of a promoter operably linked to a nucleic acid encoding a peptide or protein and/or an RNA (e.g., antisense RNA or ribozyme), wherein the promoter comprises, consists essentially of and/or consists of elements that can include, but are not limited to: a) myeloid specific promoter element PU.1A; b) myeloid specific promoter element PU.1B; c) myeloid specific promoter element C/EBPα; d) myeloid specific promoter element AML-1; e) myeloid associated promoter element Sp1; f) myeloid associated promoter element AP-1; and g) any combination of (a), (b), (c), (d), (e) and/or (f), any combination of multiples of (a), (b), (c), (d), (e) and/or (f), in any order and/or in any orientation (forward or reverse).

In some embodiments, the promoter of this invention can comprise, consist essentially of and/or consist of one, or more than one, of element (a) myeloid-specific promoter element PU.1A in forward or reverse orientation, one, or more than one, of element (b) myeloid specific promoter element PU.1B in forward or reverse orientation, one, or more than one, of (c) myeloid specific promoter element C/EBPα in forward or reverse orientation, one, or more than one, of (d) myeloid specific promoter element AML-1 in forward or reverse orientation, one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of element (a) myeloid-specific promoter element PU.1A in forward or reverse orientation, one, or more than one, of element (b) myeloid specific promoter element PU.1B in forward or reverse orientation, one, or more than one, of (c) myeloid specific promoter element C/EBPα in forward or reverse orientation, one, or more than one, of (d) myeloid specific promoter element AML-1 in forward or reverse orientation, and one, or more than one of (e) myeloid associated promoter element Sp-1 in forward or reverse orientation.

In other embodiments, the promoter of this invention can comprise, consist essentially of and/or consist of one, or more than one, of element (a) myeloid-specific promoter element PU.1A in forward or reverse orientation, one, or more than one, of element (b) myeloid specific promoter element PU.1B in forward or reverse orientation, one, or more than one, of (c) myeloid specific promoter element C/EBPα in forward or reverse orientation, one, or more than one, of (d) myeloid specific promoter element AML-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of element (a) myeloid-specific promoter element PU.1A in forward or reverse orientation, one, or more than one, of element (b) myeloid specific promoter element PU.1B in forward or reverse orientation, one, or more than one, of (c) myeloid specific promoter element C/EBPα in forward or reverse orientation, one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of element (a) myeloid-specific promoter element PU.1A in forward or reverse orientation, one, or more than one, of element (b) myeloid specific promoter element PU.1B in forward or reverse orientation, one, or more than one, of (d) myeloid specific promoter element AML-1 in forward or reverse orientation, one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of element (a) myeloid-specific promoter element PU.1A in forward or reverse orientation, one, or more than one, of (c) myeloid specific promoter element C/EBPα in forward or reverse orientation, one, or more than one, of (d) myeloid specific promoter element AML-1 in forward or reverse orientation, one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of element (b) myeloid specific promoter element PU.1B in forward or reverse orientation, one, or more than one, of (c) myeloid specific promoter element C/EBPα in forward or reverse orientation, one, or more than one, of (d) myeloid specific promoter element AML-1 in forward or reverse orientation, one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of element (b) myeloid specific promoter element PU.1B in forward or reverse orientation, one, or more than one, of (c) myeloid specific promoter element C/EBPα in forward or reverse orientation, one, or more than one, of (d) myeloid specific promoter element AML-1 in forward or reverse orientation, and one, or more than one of (e) myeloid associated promoter element Sp-1 in forward or reverse orientation.

In other embodiments, the promoter of this invention can comprise, consist essentially of and/or consist of one, or more than one, of element (b) myeloid specific promoter element PU.1B in forward or reverse orientation, one, or more than one, of (c) myeloid specific promoter element C/EBPα in forward or reverse orientation, one, or more than one, of (d) myeloid specific promoter element AML-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of element (b) myeloid specific promoter element PU.1B in forward or reverse orientation, one, or more than one, of (c) myeloid specific promoter element C/EBPα in forward or reverse orientation, one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of element (b) myeloid specific promoter element PU.1B in forward or reverse orientation, one, or more than one, of (d) myeloid specific promoter element AML-1 in forward or reverse orientation, one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of (c) myeloid specific promoter element C/EBPα in forward or reverse orientation, one, or more than one, of (d) myeloid specific promoter element AML-1 in forward or reverse orientation, one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of (c) myeloid specific promoter element C/EBPα in forward or reverse orientation, one, or more than one, of (d) myeloid specific promoter element AML-1 in forward or reverse orientation, and one, or more than one of (e) myeloid associated promoter element Sp-1 in forward or reverse orientation.

In other embodiments, the promoter of this invention can comprise, consist essentially of and/or consist of one, or more than one, of (c) myeloid specific promoter element C/EBPα in forward or reverse orientation, one, or more than one, of (d) myeloid specific promoter element AML-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of (c) myeloid specific promoter element C/EBPα in forward or reverse orientation, one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of (d) myeloid specific promoter element AML-1 in forward or reverse orientation, one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one of (e) myeloid associated promoter element Sp-1 in forward or reverse orientation, and one, or more than one of (f) myeloid associated promoter element AP-1 in forward or reverse orientation.

In some embodiments, the promoter of this invention can comprise, consist essentially of and/or consist of one, or more than one, of (d) myeloid specific promoter element AML-1 in forward or reverse orientation, and one, or more than one of (e) myeloid associated promoter element Sp-1 in forward or reverse orientation.

In some embodiments, the promoter of this invention can comprise, consist essentially of and/or consist of one, or more than one, of (d) myeloid specific promoter element AML-1 in forward or reverse orientation.

In some embodiments, the promoter of this invention can comprise, consist essentially of and/or consist of one, or more than one of (e) myeloid associated promoter element Sp-1 in forward or reverse orientation.

In other embodiments, the promoter of this invention can comprise, consist essentially of and/or consist of one, or more than one of (f) myeloid associated promoter element AP-1 in forward or reverse orientation.

In some embodiments, the promoter of this invention can comprise, consist essentially of and/or consist of one, or more than one, of element (a) myeloid-specific promoter element PU.1A in forward or reverse orientation, one, or more than one, of (c) myeloid specific promoter element C/EBPα in forward or reverse orientation, one, or more than one, of (d) myeloid specific promoter element AML-1 in forward or reverse orientation, and one, or more than one of (e) myeloid associated promoter element Sp-1 in forward or reverse orientation.

In other embodiments, the promoter of this invention can comprise, consist essentially of and/or consist of one, or more than one, of element (a) myeloid-specific promoter element PU.1A in forward or reverse orientation, one, or more than one, of (b) myeloid specific promoter element PU.1B in forward or reverse orientation, one, or more than one, of (d) myeloid specific promoter element AML-1 in forward or reverse orientation, and one, or more than one of (e) myeloid associated promoter element Sp-1 in forward or reverse orientation.

In other embodiments, the promoter of this invention can comprise, consist essentially of and/or consist of one, or more than one, of element (a) myeloid-specific promoter element PU.1A in forward or reverse orientation, one, or more than one, of (b) myeloid specific promoter element PU.1B in forward or reverse orientation, one, or more than one, of (c) myeloid specific promoter element C/EBPα in forward or reverse orientation, and one, or more than one of (e) myeloid associated promoter element Sp-1 in forward or reverse orientation.

In other embodiments, the promoter of this invention can comprise, consist essentially of and/or consist of one, or more than one, of element (a) myeloid-specific promoter element PU.1A in forward or reverse orientation, one, or more than one, of (b) myeloid specific promoter element PU.1B in forward or reverse orientation, one, or more than one, of (c) myeloid specific promoter element C/EBPα in forward or reverse orientation, and one, or more than one of (f) myeloid associated promoter element AP-1 in forward or reverse orientation.

In other embodiments, the promoter of this invention can comprise, consist essentially of and/or consist of one, or more than one, of (b) myeloid specific promoter element PU.1B in forward or reverse orientation, one, or more than one, of (c) myeloid specific promoter element C/EBPα in forward or reverse orientation, and one, or more than one of (d) myeloid specific promoter element AML-1 in forward or reverse orientation.

In other embodiments, the promoter of this invention can comprise, consist essentially of and/or consist of one, or more than one, of element (a) myeloid-specific promoter element PU.1A in forward or reverse orientation, one, or more than one, of (c) myeloid specific promoter element C/EBPα in forward or reverse orientation, and one, or more than one of (d) myeloid specific promoter element AML-1 in forward or reverse orientation.

In other embodiments, the promoter of this invention can comprise, consist essentially of and/or consist of one, or more than one, of element (a) myeloid-specific promoter element PU.1A in forward or reverse orientation, one, or more than one, of (b) myeloid specific promoter element PU.1B in forward or reverse orientation, and one, or more than one of (d) myeloid specific promoter element AML-1 in forward or reverse orientation.

In other embodiments, the promoter of this invention can comprise, consist essentially of and/or consist of one, or more than one, of element (a) myeloid-specific promoter element PU.1A in forward or reverse orientation, one, or more than one, of (b) myeloid specific promoter element PU.1B in forward or reverse orientation, one, or more than one, of (c) myeloid specific promoter element C/EBPα in forward or reverse orientation, and one, or more than one of (d) myeloid specific promoter element AML-1 in forward or reverse orientation.

In other embodiments, the promoter of this invention can comprise, consist essentially of and/or consist of one, or more than one, of element (a) myeloid-specific promoter element PU.1A in forward or reverse orientation, one, or more than one, of (b) myeloid specific promoter element PU.1B in forward or reverse orientation, and one, or more than one, of (c) myeloid specific promoter element C/EBPα in forward or reverse orientation.

In other embodiments, the promoter of this invention can comprise, consist essentially of and/or consist of one, or more than one, of element (a) myeloid-specific promoter element PU.1A in forward or reverse orientation, and one, or more than one, of (b) myeloid specific promoter element PU.1B in forward or reverse orientation.

In other embodiments, the promoter of this invention can comprise, consist essentially of and/or consist of one, or more than one, of element (a) myeloid-specific promoter element PU.1A in forward or reverse orientation and one, or more than one of (d) myeloid specific promoter element AML-1 in forward or reverse orientation.

In other embodiments, the promoter of this invention can comprise, consist essentially of and/or consist of one, or more than one, of (c) myeloid specific promoter element C/EBPα in forward or reverse orientation, and one, or more than one of (d) myeloid specific promoter element AML-1 in forward or reverse orientation.

In other embodiments, the promoter of this invention can comprise, consist essentially of and/or consist of one, or more than one, of (b) myeloid specific promoter element PU.1B in forward or reverse orientation, and one, or more than one of (d) myeloid specific promoter element AML-1 in forward or reverse orientation.

In other embodiments, the promoter of this invention can comprise, consist essentially of and/or consist of one, or more than one, of element (a) myeloid-specific promoter element PU.1A in forward or reverse orientation, and one, or more than one, of (c) myeloid specific promoter element C/EBPα in forward or reverse orientation.

In other embodiments, the promoter of this invention can comprise, consist essentially of and/or consist of one, or more than one, of (b) myeloid specific promoter element PU.1B in forward or reverse orientation, and one, or more than one, of (c) myeloid specific promoter element C/EBPα in forward or reverse orientation.

In other embodiments, the promoter of this invention can comprise, consist essentially of and/or consist of one, or more than one, of (a) myeloid specific promoter element PU.1A in forward or reverse orientation, one, or more than one, of (d) myeloid specific promoter element AML-1 in forward or reverse orientation, one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of (a) myeloid specific promoter element PU.1A in forward or reverse orientation, one, or more than one, of (d) myeloid specific promoter element AML-1 in forward or reverse orientation, and one, or more than one of (e) myeloid associated promoter element Sp-1 in forward or reverse orientation.

In other embodiments, the promoter of this invention can comprise, consist essentially of and/or consist of one, or more than one, of (a) myeloid specific promoter element PU.1A in forward or reverse orientation, one, or more than one, of (d) myeloid specific promoter element AML-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of (a) myeloid specific promoter element PU.1A in forward or reverse orientation, one, or more than one, of (c) myeloid specific promoter element C/EBPα in forward or reverse orientation, one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of (a) myeloid specific promoter element PU.1A in forward or reverse orientation, one, or more than one, of (b) myeloid specific promoter element PU.1B in forward or reverse orientation, one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of (a) myeloid specific promoter element PU.1A in forward or reverse orientation, one, or more than one, of (c) myeloid specific promoter element C/EBPα in forward or reverse orientation, and one, or more than one of (e) myeloid associated promoter element Sp-1 in forward or reverse orientation.

In other embodiments, the promoter of this invention can comprise, consist essentially of and/or consist of one, or more than one, of (a) myeloid specific promoter element PU.1A in forward or reverse orientation, one, or more than one, of (c) myeloid specific promoter element C/EBPα in forward or reverse orientation, and one, or more than one of (f) myeloid associated promoter element AP-1 in forward or reverse orientation.

In other embodiments, the promoter of this invention can comprise, consist essentially of and/or consist of one, or more than one, of (a) myeloid specific promoter element PU.1A in forward or reverse orientation and one, or more than one of (f) myeloid associated promoter element AP-1 in forward or reverse orientation.

In other embodiments, the promoter of this invention can comprise, consist essentially of and/or consist of one, or more than one, of (a) myeloid specific promoter element PU.1A in forward or reverse orientation and one, or more than one of (e) myeloid associated promoter element Sp-1 in forward or reverse orientation.

In other embodiments, the promoter of this invention can comprise, consist essentially of and/or consist of one, or more than one, of (c) myeloid specific promoter element C/EBPα in forward or reverse orientation, and one, or more than one of (e) myeloid associated promoter element Sp-1 in forward or reverse orientation.

In other embodiments, the promoter of this invention can comprise, consist essentially of and/or consist of one, or more than one, of (c) myeloid specific promoter element C/EBPα in forward or reverse orientation and one, or more than one of (f) myeloid associated promoter element AP-1 in forward or reverse orientation.

In other embodiments, the promoter of this invention can comprise, consist essentially of and/or consist of one, or more than one of (e) myeloid associated promoter element Sp-1 in forward or reverse orientation, and one, or more than one of (f) myeloid associated promoter element AP-1 in forward or reverse orientation.

In other embodiments, the promoter of this invention can comprise, consist essentially of and/or consist of one, or more than one, of (d) myeloid specific promoter element AML-1 in forward or reverse orientation, and one, or more than one of (e) myeloid associated promoter element Sp-1 in forward or reverse orientation.

In other embodiments, the promoter of this invention can comprise, consist essentially of and/or consist of one, or more than one, of (d) myeloid specific promoter element AML-1 in forward or reverse orientation and one, or more than one of (f) myeloid associated promoter element AP-1 in forward or reverse orientation.

In other embodiments, the promoter of this invention can comprise, consist essentially of and/or consist of one, or more than one, of (b) myeloid specific promoter element PU.1B in forward or reverse orientation and one, or more than one of (f) myeloid associated promoter element AP-1 in forward or reverse orientation.

In other embodiments, the promoter of this invention can comprise, consist essentially of and/or consist of one, or more than one, of (b) myeloid specific promoter element PU.1B in forward or reverse orientation and one, or more than one of (e) myeloid associated promoter element Sp-1 in forward or reverse orientation.

In other embodiments, the promoter of this invention can comprise, consist essentially of and/or consist of one, or more than one, of (a) myeloid specific promoter element PU.1A in forward or reverse orientation.

In other embodiments, the promoter of this invention can comprise, consist essentially of and/or consist of one, or more than one, of (b) myeloid specific promoter element PU.1B in forward or reverse orientation.

In other embodiments, the promoter of this invention can comprise, consist essentially of and/or consist of one, or more than one, of (c) myeloid specific promoter element C/EBPα in forward or reverse orientation.

In another embodiment of this invention, the present invention provides an isolated nucleic acid comprising a promoter operably linked to a nucleic acid encoding a peptide or protein and/or an RNA (e.g., antisense or ribozyme), wherein the promoter comprises elements that can include, but are not limited to, a) a myeloid specific promoter element comprising a core sequence GAGGAA; b) a myeloid specific promoter element comprising a core sequence AAGGAGAAG; c) a myeloid specific promoter element comprising a core sequence TTTCCAAA; d) a myeloid specific promoter element comprising a core sequence TGTGGTTGC; e) a myeloid specific promoter element comprising a core sequence TGAGTCA; f) a myeloid associated promoter element comprising a core sequence CCGCCC; and g) any combination of (a), (b), (c), (d), (e) and/or (f) (for example in any of the combinations as set forth herein for the elements PU.1A, PU.1B, C/EBPα, Sp1, AML-1 and AP-1), any combination of multiples of (a), (b), (c), (d), (e) and/or (f), in any order and/or in any orientation (forward or reverse).

In some embodiments, the promoter can comprise elements as follows: [(c) forward]-[(d) reverse]-[(a) reverse]-[(b) forward]-[(d) reverse]-[(c) reverse]-[(c) forward]-[(d) forward] [(b) forward] [(a) forward]-[(c) forward]-[(d) forward]. In other embodiments the promoter can exclude a promoter comprising elements as described in this paragraph.

In additional embodiments, the present invention provides a promoter comprising, consisting essentially of and/or consisting of the following elements: [C/EBPa forward]-[AM L-1 forward]-[PU.1A reverse]-[PU.1B reverse]-[PU.1A reverse]-[AM L-1 reverse]-[C/EBPa reverse]-[C/EBPa forward]-[AM L-1 forward] [PU.1B reverse] [PU.1A forward]-

[Sp1 forward]-[Sp1 forward] [C/EBPa forward]-[AM L-1 forward] (SP-30). In other embodiments the promoter can exclude a promoter comprising elements as described in this paragraph.

Furthermore, the present invention provides a promoter comprising, consisting essentially of and/or consisting of the following elements: [Sp1 reverse]-[C/EBPa forward]-[AM L-1 forward]-[C/EBPa forward]-[AM L-1 forward]-[C/EBPa forward]-[AM L-1 forward]-[Sp1 forward]-[PU.1A forward] (SP-60). In other embodiments the promoter can exclude a promoter comprising elements as described in this paragraph.

Also provided herein is a promoter comprising, consisting essentially of and/or consisting of the following elements: [PU.1A forward]-[PU.1B reverse]-[C/EBPa forward]-[AM L-1 forward]-[PU.1A forward]-[PU.1A forward]-[PU.1B reverse]-[PU.1B forward]-[C/EBPa forward]-[AM L-1 forward]-[PU.1B forward]-[PU.1B reverse]-[PU.1A reverse] (SP-107). In other embodiments the promoter can exclude a promoter comprising elements as described in this paragraph.

In other embodiments, the present invention provides a promoter comprising, consisting essentially of and/or consisting of the following elements: [PU.1B reverse]-[Sp1 forward]-[AM L-1 reverse]-[C/EBPa reverse]-[PU.1A forward]-[PU.1B reverse]-[AP1 forward]-[PU.1B forward]-[AM L-1 reverse]-[C/EBPa reverse]-[AP1 reverse]-[AM L-1 reverse]-[C/EBPa reverse]-[PU.1A forward]-[Sp1 reverse]-[PU.1B forward]-[AM L-1 reverse]-[C/EBPa reverse]-[PU.1B forward]-[C/EBPa forward]-[AM L-1 forward]-[PU.1B forward]-[Sp1 reverse]-[Sp1 reverse]-[AM L-1 reverse]-[C/EBPa reverse]-[PU.1B forward] (SP-144). In other embodiments the promoter can exclude a promoter comprising elements as described in this paragraph.

The present invention further provides a promoter comprising, consisting essentially of and/or consisting of the following elements: [PU.1B reverse]-[C/EBPa forward]-[AM L-1 forward]-[C/EBPa forward]-[AM L-1 forward]-[PU.1B reverse]-[PU.1A forward]-[PU.1A forward]-[Sp1 reverse]-[AM L-1 reverse]-[C/EBPa reverse]-[PU.1A forward]-[PU.1B reverse]-[PU.1A forward] (SP-146). In other embodiments the promoter can exclude a promoter comprising elements as described in this paragraph.

In other embodiments, the promoter can comprise elements as follows: [(e) reverse] [(c) forward]-[(d) forward]-[(c) forward]-[(d) forward]-[(c) forward]-[(d) forward]-[(e) forward]-[(a) forward]. In other embodiments the promoter can exclude a promoter comprising elements as described in this paragraph.

In other embodiments, the promoter can comprise elements as follows: [(e) reverse] [(c) forward]-[(d) forward]-[(c) forward]-[(d) forward]-[ (c) forward]-[(d) forward]-[(e) forward]-[(a) reverse]. In other embodiments the promoter can exclude a promoter comprising elements as described in this paragraph.

In yet other embodiments, the promoter can comprise elements as follows: [(a) forward]-[(b) forward]-[(c) forward]-[(d) forward]-[(a) forward]-[(a) forward]-[(b) forward]-[(b) reverse]-[(c) forward]-[(d) forward]-[(b) reverse]-[(b) forward]-[(a) forward]. In other embodiments the promoter can exclude a promoter comprising elements as described for this paragraph.

In other embodiments, the promoter can comprise elements as follows: [(a) reverse]-[(b) forward]-[(c) forward]-[(d) forward]-[(a) reverse]-[(a) reverse]-[(b) forward]-[(b) reverse]-[(c) forward]-[(d) forward]-[(b) reverse]-[(b) forward]-[(a) reverse]. In other embodiments the promoter can exclude a promoter comprising elements as described in this paragraph.

In certain other embodiments, the promoter can comprise elements as follows: [(b) forward]-[(e) forward]-[(d) reverse]-[(c) reverse]-[(a) forward]-[(b) forward]-[(f) forward]-[(b) forward]-[(d) reverse]-[(c) reverse]-[(f) forward]-[(d) reverse]-[(c) reverse]-[(a) reverse]-[(e) reverse]-[(b) forward]-[(d) reverse]-[(c) reverse]-[(b) forward]-[(c) forward]-[(d) forward]-[(b) forward]-[(d) reverse]-[(c) reverse]-[(b) forward]. In other embodiments the promoter can exclude a promoter comprising elements as described in this paragraph.

In various other embodiments, the promoter can comprise elements as follows: [(b) forward]-[(c) forward]-[(d) forward]-[(c) forward]-[(d) forward]-[(b) forward]-[(a) forward]-[(a) forward]-[(e) reverse]-[(d) reverse]-[(c) reverse]-[(a) forward]-[(b) forward]-[(a) forward]. In other embodiments the promoter can exclude a promoter comprising elements as described in this paragraph.

In yet other embodiments, the promoter can comprise elements as follows: [(b) forward]-[(c) forward]-[(d) forward]-[(c) forward]-[(d) forward]-[(b) forward]-[(a) reverse]-[(a) reverse]-[(e) reverse]-[(d) reverse]-[(c) reverse]-[(a) reverse]-[(b) forward]-[(a) reverse]. In other embodiments the promoter can exclude a promoter comprising elements as described in this paragraph.

In other embodiments of the invention, the promoter can comprise elements as follows: [(b) forward]-[(e) forward]-[(d) reverse]-[(c) reverse]-[(a) reverse]-[(b) forward]-[(f) forward]-[(b) reverse]-[(d) reverse]-[(c) reverse]-[(f) reverse]-[(d) reverse]-[(c) reverse]-[(a) reverse]-[(e) reverse]-[(b) reverse]-[(d) reverse]-[(c) reverse]-[(b) reverse]-[(c) forward]-[(d) forward]-[(b) reverse]-[(d) reverse]-[(c) reverse]-[(b) reverse]. In other embodiments the promoter can exclude a promoter comprising elements as described in this paragraph.

In a further embodiment of the invention, the promoter can comprise elements as follows: [(c) forward]-[(d) forward]-[(a) forward]-[(b) forward]-[(d) reverse]-[(c) reverse]-[(c) forward]-[(d) forward] [(b) forward] [(a) reverse]-[(c) forward]-[(d) forward]. In other embodiments the promoter can exclude a promoter comprising elements as described in this paragraph.

In still further embodiments of the invention, the promoter can comprise elements as follows: [(c) forward]-[(d) forward]-[(c) forward]-[(d) forward]-[(c) forward]-[(d) forward]-[(e) forward]-[(a) reverse]. In other embodiments the promoter can exclude a promoter comprising elements as described in this paragraph.

In yet another embodiment of the invention, the promoter can compromise elements as follows: [(a) reverse]-[(b) forward]-[(c) forward]-[(d) forward]-[(a) reverse]-[(a) reverse]-[(b) forward]-[(b) reverse]-[(c) forward]-[(d) forward]-[(b) reverse]-[(b) forward]-[(a) forward]. In other embodiments the promoter can exclude a promoter comprising elements as described in this paragraph.

In a further embodiment of the invention, the promoter can compromise elements as follows: [(b) forward]-[(c) forward]-[(d) forward]-[(c) forward]-[(d) forward]-[(b) forward]-[(a) reverse]-[(a) reverse]-[(e) reverse]-[(d) reverse]-[(c) reverse]-[(a) reverse]-[(b) forward]-[(a) reverse]. In other embodiments the promoter can exclude a promoter comprising elements as described in this paragraph.

The present invention also provides an isolated nucleic acid as described above, wherein the nucleic acid functions as a promoter that is more active in myeloid (CD11b positive) cells than the CMV promoter, the CSF-1R promoter and/or the CD11b promoter. The nucleic acid of this invention can have an activity either in vitro or in vivo that is 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900 or 1000-fold greater, as compared to the activity of the CMV promoter, the CSF-1R promoter and/or the CD11b promoter.

Further provided in the present invention is a super promoter comprising, consisting essentially of and/or consisting of the nucleotide sequence of SEQ ID NO:21, SEQ ID NO:22, SEQ ID NO:23 and/or SEQ ID NO:24, singly or in any combination, in any number of multiples of the same nucleotide sequence and/or in any order relative to one another.

Additionally provided in the present invention is a super promoter comprising, consisting essentially of and/or consisting of the nucleotide sequence of SEQ ID NO:10, SEQ ID NO:11, SEQ ID NO:12, SEQ ID NO:13, SEQ ID NO:25, SEQ ID NO:26 and SEQ ID NO:27, singly or in any combination, in any number of multiples of the same nucleotide sequence and/or in any order relative to one another.

Additionally provided in the present invention is a method of identifying a nucleic acid having promoter activity that is greater in myeloid cells than the promoter activity of a CMV promoter, a CSF-1R promoter and/or a CD11b promoter (as defined herein), comprising:

a) providing a nucleic acid according to the methods described herein, comprising a promoter operably linked to a nucleic acid encoding a peptide or protein, wherein the promoter comprises elements selected from the group consisting of: a) myeloid specific promoter element PU.1A; b) myeloid specific promoter element PU.1B; c) myeloid specific promoter element C/EBPα; d) myeloid specific promoter element AML-1; e) myeloid associated promoter element Sp1; f) myeloid associated promoter element AP-1; and g) any combination of (a), (b), (c), (d), (e) and/or (f), any combination of multiples of (a), (b), (c), (d), (e) and/or (f), in any order and in any orientation (forward or reverse); and b) comparing the promoter activity of the nucleic acid of (a) in myeloid cells with the promoter activity of a CMV promoter, a CSF-1R promoter and/or a CD11b promoter in myeloid cells, wherein a nucleic acid having activity in myeloid cells that is greater than the promoter activity in myeloid cells of a CMV promoter, a CSF-1R promoter and/or a CD11b promoter is identified as a nucleic acid having promoter activity that is greater in myeloid cells than the promoter activity of a CMV promoter, a CSF-1R promoter and/or a CD11b promoter. This method of identifying such nucleic acids can be carried out in vitro and/or in vivo according to protocols well known in the art for measuring promoter activity and as described in the Examples herein.

Further provided is a method of producing a nucleic acid comprising a promoter operably linked to a nucleic acid encoding a peptide or protein, wherein the promoter comprises elements selected from the group consisting of: a) myeloid specific promoter element PU.1A; b) myeloid specific promoter element PU.1B; c) myeloid specific promoter element C/EBPα; d) myeloid specific promoter element AML-1; e) myeloid associated promoter element Sp1; f) myeloid associated promoter element AP-1; and g) any combination of (a), (b), (c), (d), (e) and/or (f), in any combination of multiples of (a), (b), (c), (d), (e) and/or (f), in any order and in any orientation (forward or reverse), comprising:

1) producing each element (a) through (f) according to protocols as described herein;

2) combining each element under conditions whereby random ligation can occur; and 3) separating each resulting nucleic acid comprising the elements.

The term "nucleic acid" as used herein refers to single- or double-stranded molecules which can be DNA, comprised of the nucleotide bases A, T, C and G, or RNA, comprised of the bases A, U (substitutes for T), C, and G. The nucleic acid can represent a coding strand or its complement. Nucleic acids can be identical in sequence to the sequence that is naturally occurring or can include alternative codons, which encode the same amino acid as that which is found in the naturally occurring sequence. Furthermore, nucleic acids may include codons that provide conservative substitutions of amino acids as are well known in the art. The nucleic acids of this invention can also comprise any nucleotide analogs and/or derivatives as are well known in the art.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by well-known techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

Also as used herein, the terms "peptide," "protein" and "polypeptide" are used to describe a chain of amino acids, which correspond to those encoded by a nucleic acid. A peptide usually describes a chain of amino acids of from two to about 30 amino acids and polypeptide or protein usually describes a chain of amino acids having more than about 30 amino acids. The term polypeptide or protein can refer to a linear chain of amino acids or it can refer to a chain of amino acids that have been processed and folded into a functional protein. As presented herein, the terms protein and polypeptide can be used interchangeably. It is understood, however, that 30 is an arbitrary number with regard to distinguishing peptides and polypeptides and the terms can be used interchangeably for a chain of amino acids around 30.

The peptides and polypeptides of the present invention are obtained by isolation and purification of the peptides and polypeptides from cells where they are produced naturally or by expression of a recombinant and/or synthetic nucleic acid encoding the peptide or polypeptide. The peptides and polypeptides of this invention can be obtained by chemical synthesis, by proteolytic cleavage of a polypeptide and/or by synthesis from nucleic acid encoding the peptide or polypeptide.

It is also understood that the peptides and polypeptides of this invention can contain conservative substitutions where a naturally occurring amino acid is replaced by one having similar properties and which does not alter the function of the polypeptide. Such conservative substitutions are well known in the art. Thus, it is understood that, where desired, modifications and changes, which are distinct from the substitutions which enhance immunogenicity, can be made in the nucleic acid and/or amino acid sequence of the peptides and polypeptides of the present invention and still obtain a peptide or polypeptide having like or otherwise desirable characteristics. Such changes can occur in natural isolates or can be synthetically introduced using site-specific mutagenesis, the procedures for which, such as mis-match polymerase chain reaction (PCR), are well known in the art. One of skill in the art will also understand that polypeptides and nucleic acids that contain modified amino acids and nucleotides, respectively (e.g., to increase the half-life and/or the therapeutic efficacy of the molecule), can be used in the methods of the invention.

The nucleic acid of this invention can be part of a recombinant nucleic acid construct comprising any combination of restriction sites and/or functional elements as are well known in the art that facilitate molecular cloning and other recombinant DNA manipulations. Thus, the present invention further provides a recombinant nucleic acid construct comprising a nucleic acid of this invention.

The nucleic acid of this invention can also include, for example, antibiotic resistance markers and/or other selectable and/or screenable markers as are known in the art, origins of replication and/or expression control sequences, such as, for example, a promoter (constitutive or inducible), an enhancer and necessary information processing sites, such as initiation signals, ribosome binding sites, RNA splice sites, multiple cloning sites, polyadenylation sites and transcriptional terminator sequences. The nucleic acid of this invention can also comprise one or more internal ribosome binding sites (IRES) for expression of more than one coding sequence from the same construct.

A nucleic acid encoding a peptide or polypeptide of this invention can readily be determined based upon the genetic code for the amino acid sequence of the selected peptide or polypeptide and many nucleic acids will encode any selected peptide or polypeptide, based upon the redundancy of the genetic code. Modifications in the nucleic acid sequence encoding the peptide or polypeptide are also contemplated. Modifications that can be useful are modifications to the sequences controlling expression of the peptide or polypeptide to make production of the peptide or polypeptide inducible or repressible as controlled by the appropriate inducer or repressor. Such methods are standard in the art. The nucleic acid of this invention can be generated by means standard in the art, such as by recombinant nucleic acid techniques and/or by synthetic nucleic acid synthesis and/or in vitro enzymatic synthesis.

For example, the nucleic acids and vectors of this invention can be introduced into cells via any gene transfer mechanism, such as, for example, virus-mediated gene delivery, calcium phosphate mediated gene delivery, lipofection, electroporation, uptake by cells via endocytosis, microinjection and/or proteoliposomes.

The present invention further provides a vector comprising a nucleic acid of this invention. The vector of this invention can be any type of vector that facilitates delivery of nucleic acid to a cell. A vector of this invention can be a nucleic acid vector such as a plasmid, cosmid, virus, and/or an artificial chromosome. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols.

In some embodiments, the expression vector can comprise, for example, viral nucleic acid including, but not limited to, nucleic acid from vaccinia virus, adenovirus, lentivirus, retrovirus, pseudotyped virus (e.g., pseudotyped lentivirus, pseudotyped retrovirus), alphavirus, herpesvirus, vaccinia virus, polyoma virus, picornavirus, hybrid adeno/adeno-associated virus and/or adeno-associated virus (AAV; see for example, Owens (2002) "Second generation adeno-associated virus type 2-based gene therapy systems with the potential for preferential integration into AAVS1" *Curr. Gene Ther.* 2:145-159, the entire contents of which are incorporated herein by reference for teachings of AAV vectors), as well as any other viral vector now known or later identified according to methods well known in the art.

In yet other embodiments, the vector of this invention can be any vehicle for delivery of nucleic acid into a cell that is lipid-, peptide-, and/or protein-based. For example, the nucleic acid or vector of this invention can also be in a liposome (e.g., FuGene6; VDL liposomes) or a delivery vehicle, which can be taken up by a cell via receptor-mediated or other type of endocytosis. The vectors, liposomes and other delivery vehicles of this invention can further comprise molecules on the surface that allow for specific cell targeting and binding, as are well known in the art.

As one example, the nucleic acid and/or vector of this invention can be in a liposome developed in the Vector Development Laboratory (VDL) of Baylor College of Medicine. According to the manufacturer, "These liposomes and nucleic acid liposome complexes have extended half life in the circulation, are stable in serum, have broad biodistribution, efficiently encapsulate all types of nucleic acids, are targetable to specific organs and cell types, are able to penetrate through tight barriers in several organs, and have been optimized for nucleic acid:lipid ratio and colloidal suspension in vivo."

Introduction of the nucleic acids of this invention into cells can be achieved by any of numerous, well-known approaches, for example, but not limited to, direct transfer of the nucleic acids, in a plasmid or viral vector, or via transfer in cells or in combination with carriers such as cationic liposomes. Such methods are well known in the art and readily adaptable for use in the methods described herein. Furthermore, these methods can be used to target certain cell populations by using the targeting characteristics of the carrier, which would be well known to the skilled artisan.

Physical transduction techniques can also be used, such as liposome delivery and receptor-mediated and other endocytosis mechanisms (see, for example, Schwartzenberger et al., *Blood* 87:472-478, 1996). This invention can be used in conjunction with any of these or other commonly used nucleic acid transfer methods. Appropriate means for transfection, including viral vectors, chemical transfectants, or physico-mechanical methods such as electroporation and direct diffusion of DNA, are described by, for example, Wolff et al., *Science* 247:1465-1468, (1990); and Wolff, *Nature* 352:815-818, (1991).

Thus, in various embodiments, the nucleic acid of this invention can be in a cell, which can be a cell expressing the nucleic acid of this invention. In addition, the vector of this invention can be in a cell, which can be a cell expressing the nucleic acid of the vector in the cell.

The cell of this invention can be a myeloid (CD11b positive) cell, a hematopoietic stem cell, a macrophage, monocyte, neutrophil, eosinophil or basophil and/or any combination of these cells and/or other cells suitable for delivery of nucleic acids to a treatment site, wherein the nucleic acids are expressed under the control of a promoter of this invention. In certain embodiments, the cell of this invention is a cell of the subject to be treated, i.e., an autologous cell. In other embodiments, the cell of this invention can be a cell that is not a cell of the subject to be treated, i.e., the cell is heterologous to the subject to be treated. Thus, in various embodiments of this invention, a composition of this invention can comprise either or both autologous and heterologous cells.

Thus, one embodiment of this invention is a method of producing a cell of this invention, comprising transducing and/or transfecting a cell of this invention with a vector and/or nucleic acid of this invention. Also provided is a cell produced by the methods of this invention.

The nucleic acid of this invention can encode any protein or peptide and in some embodiments, the protein or peptide can be a therapeutic peptide or protein. Examples of therapeutic peptides and proteins of this invention include, but are not limited to, glial cell-derived neurotrophic factor (GDNF), nerve growth factor (NGF), brain-derived neurotrophic factor (BDNF), ciliary neurotrophic factor (CNTF), neprilysin, lysosomal protective protein 1 cathepsin A (PPCA), insulin-like growth factor (IGF-1), glucocerebrosidase, liver X receptors, apoE, apoA1, ATP-binding cassette transporter A1 (ABCA1), gp91phox, p47phox, p67phox and p22phox, as well as any other therapeutic peptide or protein that can be used in a method of this invention to treat a disorder.

As used herein, the nucleic acid encoding a protein or peptide of this invention can be genomic (e.g., a complete gene having all of the known elements of a gene), or a coding sequence (e.g., messenger RNA, cDNA, etc.). Thus, in this context, the term "nucleic acid" is meant to be either a gene or a coding sequence and in some instances the terms are meant to be used interchangeably.

It is further contemplated that the compositions of this invention can be used to treat various disorders in a subject by delivery of a gene to a treatment site in the subject, wherein the gene is expressed under the control of a promoter of this invention. Thus, the present invention also provides a method of treating a disorder in a subject in need thereof, comprising administering to the subject an effective amount of a composition of this invention, which can be a cell of this invention and/or a composition comprising a cell of this invention.

The disorder that can be treated according to the methods of this invention can include but is not limited to Parkinson's disease, Alzheimer's disease, amyotrophic lateral sclerosis (ALS, also known as Lou Gerhig's disease), chronic granulomatous disease, Huntington's disease, Gaucher's disease, galactosialidosis, atherosclerosis and other neurodegenerative diseases now known or later identified that can be treated according to the methods of this invention.

The present invention additionally provides a method of producing a macrophage comprising a nucleic acid of this invention, comprising transducing a hematopoietic stem cell with a viral vector comprising the nucleic acid and maintaining the hematopoietic stem cell under conditions whereby it differentiates into the macrophage. Such conditions can be ex vivo and/or in vivo and are as described in the Examples provided herein and as are well known in the art.

In one embodiment, the present invention provides a method of treating a disorder, which can be, but is not limited to, Parkinson's disease, Alzheimer's disease, Huntington's disease, galactosialidosis, amyotrophic lateral sclerosis, chronic granulomatous disease, other neurodegenerative diseases and atherosclerosis, in a subject in need thereof, comprising: a) transducing a hematopoietic stem cell of the subject with a viral vector comprising a nucleic acid of this invention encoding a peptide or protein that imparts a therapeutic effect to the subject; and b) delivering the hematopoietic stem cell to the subject.

In further embodiments, the nucleic acids and/or cells of this invention can be combined in an administration protocol with a therapeutic agent and/or a surgical procedure. For example, in some embodiments of this invention, the compositions of this invention can be administered to a subject in combination with certain modes of local cell administration (e.g., intra-medullary). In other embodiments, the compositions of this invention can be administered to a subject in combination with various therapeutic agents. One examples of such a therapeutic agent can be a pharmacologic agent that mobilizes cells from the transplanted bone marrow and/or that enhances their functional capabilities in order to improve the therapeutic effect of the gene. Such agents can include, but are not limited to, corticosteroids and hematopoietic colony-stimulating factors (e.g., GM-CSF, G-CSF).

Another therapeutic approach can include MGMT-mediated in vivo selection, which results in elimination of non-transduced bone marrow cells, thereby enriching for cells expressing the therapeutic nucleic acid of this invention. MGMT-mediated in vivo selection is a method that can be employed to increase the proportion of transduced hematopoietic stem cells, involving transduction of a drug-resistance gene followed by chemotherapeutic treatment to mediate selection. For example, the cells can be transduced with O6-methylguanine-DNA-methyltransferase (MGMT), which is expressed to produce the gene product, O6-alkylguanine-DNA-alkyltransferase (AGT), which functions to repair alkylated DNA. The chemotherapeutic agent, chloroethylating agent 1,3-bis(2-chloroethyl)-1-nitrosourea (BCNU), a potent stem cell toxin, can be administered. O6-benzylguanine (BG) inactivates endogenous AGT, but not MGMT mutants (G156A or P140K). Selection based on MGMT (P140K) gene transduction and BG/BCNU treatment has been shown to increase the proportion of transduced cells in vivo to 99% (Zielske et al. "In vivo selection of MGMT (P140K) lentivirus-transduced human NOD/SCID repopulating cells without pretransplant irradiation conditioning" *J. Clin. Invest.* 112(10):1561-70 (2003); Jansen et al. "Hematoprotection and enrichment of transduced cells in vivo after gene transfer of MGMT(P140K) into hematopoietic stem cells" *Cancer Gene Therapy* 9(9):737-46 (2002)).

A therapeutic agent of this invention can be administered before, concurrent with, and/or within a few hours, several hours, and/or 1, 2, 3, 4, 5, 6, 7, 8, 9, and/or 10 days before or after the administration of a nucleic acid and/or cell of this invention to a subject.

A therapeutic agent of this invention can be included in a composition of this invention with a nucleic acid and/or vector and/or cell of this invention so that the therapeutic agent is administered to a subject simultaneously with the nucleic acid and/or vector and/or cell. A therapeutic agent of this invention can also be in a composition without a nucleic acid and/or vector and/or cell of this invention so that the therapeutic agent can be administered either before, simultaneously with, and/or after administration of the nucleic acid and/or vector and/or cell of this invention to a subject. If irradiation and/or a surgical procedure is employed in the methods of this invention, it can be administered to a subject either before, simultaneously with, and/or after administration of the nucleic acid and/or vector and/or cell and/or therapeutic agent of this invention.

When administered to a subject in the same treatment protocol (either simultaneously or at separate time points in any sequence), the nucleic acid and/or vector of this invention and the therapeutic agent of this invention can be administered to the subject in amounts that produce a ratio of nucleic acid/vector to therapeutic agent of 100:1, 90:1, 80:1, 70:1, 60:1, 50:1, 40:1, 30:1. 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90 and/or 1:100 or more.

As indicated above, the nucleic acids, vectors, cells and/or therapeutic agents of this invention can be present in a composition (e.g., a pharmaceutical composition) comprising a pharmaceutically acceptable carrier. Thus, pharmaceutical compositions comprising a nucleic acid, vector, cell and/or therapeutic agent of this invention and a pharmaceutically acceptable carrier are also provided. The compositions described herein can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of this invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier can be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients.

The pharmaceutical compositions of this invention include those suitable for oral, rectal, vaginal, topical, inhalation (e.g., via an aerosol) buccal (e.g., sub-lingual), vaginal, parenteral (e.g., subcutaneous, subconjunctival, intravesicular, intramuscular, intradermal, intraarticular, intrapleural, intratracheal, intraperitoneal, intracerebral, intraarterial, intracranial, intraocular, intratumoral, intravenous, intramedullary, etc.), topical (i.e., both skin and mucosal surfaces, including airway surfaces) and/or transdermal administration, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered. In some embodiments of this invention, the compositions of this invention can be injected into the bone marrow cavity.

In particular embodiments, more than one administration (e.g., two, three, four or more administrations) may be employed to achieve the desired level of gene expression.

In some embodiments of the invention, the composition is administered to the CNS (e.g., to the brain or to the eye). The composition can be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and amygdala), limbic system, neocortex, corpus striatum, cerebrum, and inferior colliculus. The composition can also be administered to different regions of the eye such as the retina, cornea or optic nerve.

The composition can be delivered into the cerebrospinal fluid (e.g., by lumbar puncture) for more disperse administration. The composition can further be administered intravascularly to the CNS in situations in which the blood-brain barrier has been perturbed (e.g., brain tumor or cerebral infarct).

The composition can be administered to the desired region(s) of the CNS by any route known in the art, including but not limited to, intrathecal, intra-ocular, intracerebral, intraventricular, intranasal, intra-aural, intra-ocular (e.g., intra-vitreous, sub-retinal, anterior chamber) and peri-ocular (e.g., sub-Tenon's region) delivery.

Typically, the composition is administered in a liquid formulation by direct injection (e.g., stereotactic injection) to the desired region or compartment in the CNS. In other embodiments, the composition is provided by topical application to the desired region or by intra-nasal administration of an aerosol formulation. Administration to the eye or into the ear, can be by topical application of liquid droplets. As a further alternative, the composition can be administered as a solid, slow-release formulation. For example, controlled release of parvovirus and AAV vectors is described by international patent publication WO 01/91803.

In other embodiments, a composition is administered to the liver of the subject. Administration to the liver may be achieved by any method known in the art, including, but not limited to intravenous administration, intraportal administration, intrabiliary administration, intra-arterial administration, and direct injection into the liver parenchyma.

The compositions disclosed herein may be administered to the lungs of a subject by any suitable means, but are preferably administered via an aerosol suspension of respirable particles comprised of the composition, which the subject inhales. The respirable particles may be liquid or solid. Aerosols of liquid particles comprising the composition may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the composition may likewise be produced with any solid particulate medicament aerosol generator, by techniques known in the pharmaceutical art.

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a composition of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sub-lingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions of this invention suitable for parenteral administration can comprise sterile aqueous and non-aqueous injection solutions of the composition of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration are preferably presented as unit dose suppositories. These can be prepared by admixing the composition with one or more conventional solid carriers, such as for example, cocoa butter and then shaping the resulting mixture.

Pharmaceutical compositions of this invention suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharmaceutical Research* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

Thus the present invention also provides a method of treating a disorder in a subject, comprising administering to the subject an effective amount of a nucleic acid, a vector, a cell and/or a composition of this invention to the subject, thereby treating the disorder in the subject.

The methods of this invention can also include the steps of administering to the subject an effective amount of one or more therapeutic agents, surgical procedures and/or radiation to the subject, either before, simultaneously with, and/or after administration of the nucleic acid, vector, cell and/or composition to the subject.

A subject of this invention is any subject who is susceptible to the disorders of this invention and who is or may be in need of and/or who could acquire a beneficial effect from the treatment methods of this invention (e.g., a subject predisposed to, suspected of having, or diagnosed with a disorder of this invention). The subject of this invention can be, for example, avian or mammalian and in some embodiments, is a human.

Efficacy of the treatment methods of this invention can be determined according to well known protocols for determining the outcome of a treatment of a disorder of this invention. Determinants of efficacy of treatment, include, but are not limited to, overall survival, disease-free survival, improvement in symptoms, time to progression and/or quality of life, etc., as are well known in the art.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art.

"Effective amount" refers to an amount of a compound or composition that is sufficient to produce a desired effect, which can be a therapeutic effect. The effective amount will vary with the age, general condition of the subject, the severity of the condition being treated, the particular composition and/or agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000)).

When cells of this invention are administered to a subject, a dosage range from about $10^4$ to about $10^{11}$ cells in a composition of this invention, including any dosage amount or dosage sub-range within this range, will have therapeutic efficacy, with all weights being calculated based upon the weight of the composition.

As one example, cells of this invention can be administered to a subject intravenously in the dosage range provided herein as a single administration. Efficacy could be monitored by amelioration for signs and symptoms of the disease or slowing of the rate of progression of disease. Surrogate markers would be derived by assessment of expression of the therapeutic gene in blood and tissues (e.g., by mRNA and/or protein levels). The cells can be administered additional times as indicated, for example, by a waning therapeutic effect over time.

When the composition of this invention is to be administered to a subject as a viral vector, a suitable dosage range can be determined for that viral vector according to standard protocols. Dosages of viral vectors to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^3$, $10^{14}$, $10^{15}$ transducing units or more, and can be about $10^8$-$10^{13}$ transducing units in some embodiments, and can also be about $10^9$ to $10^{12}$ transducing units in other embodiments.

As one example, if the nucleic acid of this invention is delivered to the cells of a subject in an adenovirus vector, the dosage for administration of adenovirus to humans can range from about $10^7$ to $10^9$ plaque forming units (pfu) per injection, but can be as high as $10^{12}$ pfu per injection (Crystal (1997) "Phase I study of direct administration of a replication deficient adenovirus vector containing *E. coli* cytosine deaminase gene to metastatic colon carcinoma of the liver in association with the oral administration of the pro-drug 5-fluorocytosine" *Human Gene Therapy* 8:985-1001; Alvarez and Curiel (1997) "A phase I study of recombinant adenovirus vector-mediated delivery of an anti-erbB-2 single chain (sFv) antibody gene from previously treated ovarian and extraovarian cancer patients" *Hum. Gene Ther.* 8:229-242; the entire contents of which are incorporated by reference herein for teachings of administration of viral vectors).

The frequency of administration of a composition of this invention can be as frequent as necessary to impart the desired therapeutic effect. For example, the composition(s) can be administered one, two, three, four or more times per day, one, two, three, four or more times a week, one, two, three, four or more times a month, one, two, three or four times a year, etc., as necessary to control the symptoms and/or effects of the disorder being treated. The different compositions described herein can be administered simultaneously and/or sequentially in any order, which can be repeated, reversed and/or otherwise varied. Intervals between sequential administrations of different compounds can be optimized according to methods known in the art such that an advantageously combined effect is achieved. The amount and frequency of administration of the composition(s) of this invention will vary depending on the particular condition being treated and the desired therapeutic effect.

The compositions of this invention can be administered to a cell of a subject in vivo or ex vivo. For administration to a cell of the subject in vivo, as well as for administration to the subject, the compositions of this invention can be administered, for example as noted above, orally, parenterally (e.g., intravenously or intra-arterially), by intramuscular injection, intradermally (e.g., by gene gun), by intraperitoneal injection, subcutaneous injection, transdermally, extracorporeally, topically, intratumorally and the like.

If ex vivo methods are employed, cells or tissues can be removed and maintained outside the body according to standard protocols well known in the art while the compositions of this invention are introduced into the cells or tissues. For example, the nucleic acids and vectors of this invention can be introduced into cells via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or transplanted back into the subject per standard methods for the cell or tissue type. Standard methods are known for transplantation or infusion of various cells into a subject.

The present invention additionally provides kits comprising the nucleic acid and/or vectors and/or cells and/or compositions of this invention, with or without therapeutic agents, along with appropriate buffers, diluents, vessels and/or devices, etc. for measuring a specific amount and for administering the compositions to a subject of this invention.

EXAMPLES

Example 1

Parkinson's Disease

Neurodegenerative diseases, such as Alzheimer's disease (AD), Parkinson's disease (PD), and lysosomal storage disorders (LSD), affect a large population of patients. Existing therapies only manage to ameliorate the symptoms without halting the progression of these diseases. Gene therapy holds the potential for revolutionizing medicine by treating the causes of disease rather than the symptoms. The major challenges have been delivery of DNA to the target cells and duration and level of expression, particularly in the central nervous system (CNS) due to the exquisite anatomy of the brain. The present invention is thus directed, in certain embodiments, to gene therapy protocols for the treatment of neurodegenerative disorders that exploit the fact that macrophages are recruited from bone marrow to most tissues of the body, including the brain.

By random assembly of E-box, MEF-2, TEF-1, and SRE sites into synthetic promoter recombinant libraries, and screening of hundreds of individual clones for transcriptional activity in vitro and in vivo, several artificial promoters were isolated whose transcriptional potencies greatly exceed those of natural myogenic and viral gene promoters (Li et al., 1999). A series of super macrophage promoters (SMP) have been developed that are up to 100-fold stronger than some currently characterized macrophage promoters, including CSF-1R promoter. These promoters are employed in gene therapy protocols in a mouse model of PD, the second most common progressive neurodegenerative disorder. PD is caused by massive degeneration of nigrostriatal dopaminergic neurons.

This aspect of the present invention is directed to the highly effective CNS delivery of GDNF through its expression in macrophages/microglia by ex vivo transduction of hematopoietic stem cells (HSCs) with lentiviral vectors carrying the super-macrophage promoters, followed by syngeneic transplantation of these HSCs, resulting in correction of the pathologic changes and neurological defects in animal models of PD.

The super macrophage promoters of this invention are characterized using 1) transplantation of bone marrow stem cells transduced ex vivo with lentiviral vectors and 2) expression in transgenic mice using EGFP (enhanced green fluorescent protein) as a reporter. Lentiviral particles are produced by transient cotransfection of Lenti-SMP-EGFP lentivector plasmids with the three packaging plasmids into 293T cells. Mouse bone marrow cells are collected, transduced with the concentrated lentiviral particles, and infused back into lethally irradiated syngeneic recipients. Transgenic mice are made with the super promoter-EGFP cassette, flanked by a 1.2 kb DNA fragment of chromatin insulator to avoid silencing of the transgene. Transgene copy number is assessed by Southern blot analysis. To check monocyte/macrophage expression of the transgene, peripheral blood leukocytes, peritoneal cells, bone marrow cells and splenocytes are isolated and analyzed by fluorescence activated cell sorting (FACS) for co-expression of EGFP with leukocyte markers. Immunocytochemistry of brain sections is performed to examine EGFP expression in macrophage/microglia. For the transgenic mice, EGFP transcripts and protein in various tissues are tested by northern or real-time RT-PCR and western blot analyses, respectively. Promoters with the greatest strength and tissue-specificity for macrophages/microgliocytes are used in further studies described herein.

Studies are conducted to demonstrate the amelioration of neurodegeneration in the MPTP (1-methyl-4-phenyl-1,2,3,6-tetrahydropyridine) mouse model of Parkinson's disease by syngeneic transplantation of HSC transduced ex vivo with lentivectors expressing GDNF nucleic acid in macrophages/microglia driven by the SMP. Human and mouse GDNF cDNA is separately inserted into Lenti-SMP-GFP to replace the EGFP gene. The GDNF is either tagged by flag sequence (DYKDDDDK, SEQ ID NO:1) at the carboxyl terminus or not. The resulting constructs, Lenti-SMP-hGDNF, Lenti-SMP-hGDNFflag, Lenti-SMP-mGDNF, Lenti-SMP-mGDNFflag and the parent vector Lenti-SMP-GFP are each co-transfected together with the three packaging plasmids into 293T cells to produce lentiviral particles, which are concentrated by ultra-centrifugation and used to transduce mouse bone marrow stem cells ex vivo for 6 hours. The transduced bone marrow cells are infused into lethally irradiated recipient mice by tail vein injection. Four weeks after bone marrow transplantation, the recipient mice are injected subcutaneously with four doses of MPTP (14 mg/kg) at 2 h intervals. At selected time points post MPTP treatment, positron emission tomography (PET) scans and behavioral testing is performed, and the mice are killed for tissue collection. Dopamine uptake and expression of tyrosine hydroxylase (TH) are measured. Dopaminergic neurons are counted and apoptosis in cells of the substantia nigra pars compacta (SN) is examined by TUNEL staining and immunohistochemical analysis for active caspase-3.

Studies are also conducted to demonstrate the amelioration of neurodegeneration in the MPTP mouse model of Parkinson's disease by syngeneic transplantation of HSC transduced ex vivo with tetracycline-regulatable lentivectors expressing GDNF gene in macrophages/macrogliocytes. The Tet-on switch is included in 1) a two-vector system and 2) a combined vector carrying both the tetracycline trans-activator and the transgene expression units within the same backbone. Bone marrow stem cells are transduced ex vivo with the lentivirus and transplanted into mice of three different ages: 8 weeks (young), 8 months (middle-aged), and 20 months (old). Young mice receive a single dose of MPTP at 55 mg/kg, middle-aged mice a dose at 40 mg/kg, and old mice a reduced dose. To evaluate the effects of macrophage/super promoter-mediated delivery and expression of GDNF upon degenerating nigrostriatal neurons in the MPTP model of PD, GDNF expression is initiated by tetracycline treatment before and at various times (1, 4, 8, 14, 28 days) after MPTP administration. Again, at specific time points post-MPTP treatment and initiation of GDNF expression, GDNF effects on dopaminergic neuroprotection, restoration, and functional enhancement are examined as described herein.

A series of super macrophage promoters (5-100-fold stronger than CSF-1R or CD11b promoters) have been selected from a synthetic library. This library was constructed by random ligation of myeloid-specific promoter elements PU.1, C/EBPα, and AML-1 and myeloid-associated promoter elements Sp1 and AP-1 (Table 3), and then splicing them upstream of a mini-myeloid promoter/luciferase vector, pGL3-p47-86, characterized previously. The CD68 basal promoter can also be used. High monocyte/macrophage promoter activity was screened for by transient transfections of monocyte cell line THP-1. One of the selected super promoters has been tested in vivo by various methods to demonstrate its utility in targeted gene delivery. A method is also developed to transduce HSC with lentiviral vectors to levels sufficient for pan-target cell expression of therapeutic nucleic acids, while maintaining their stem cell nature. Evidence is also provided that bone marrow-derived macrophages/microglial cells accumulate in sites of MPTP-induced lesions.

The PU.1 binding site of the p47$^{phox}$ promoter is essential for transcriptional activity in myeloid cells: The p47$^{phox}$ protein, an essential cytosolic component of the phagocyte NADPH oxidase, is exclusively expressed in macrophages and neutrophils. Primer extension analysis demonstrated a predominant transcriptional start site (TSS) 21 nucleotides upstream of the translation initiation codon. Transcription of p47$^{phox}$ in HL-60 cells was largely dependent on elements contained in the proximal portion of the 5' flanking region, specifically between positions −36 and −86, relative to the TSS. DNAse I footprint analysis identified a protected region between −37 and −53 that contains a consensus binding site for the myeloid-specific transcription factor PU.1. Moreover, this element binds specifically to PU.1 from either myeloid cell nuclear extracts or in vitro synthesis and mutations of the PU.1 site abolished binding and promoter activity. The promoter was active in a number of myeloid cells, but not in non-myeloid cells, unless a PU.1 expression vector was co-transfected. Thus, p47$^{phox}$ transcription requires PU.1, likely accounting for the limitation of its expression to phagocytic cells.

Flanking sequences of PU.1 binding sites are functionally critical in monocyte/macrophage promoters: The consensus PU.1 binding sequence (GAGGAA) is located on the lower DNA strand from bp −40 to −45 relative to the p47$^{phox}$ transcriptional start site. Although p47phox promoter-luciferase reporter construct −46 dictates tissue-specific expression, the −86 construct has maximum activity. The role of immediate upstream flanking sequences of the PU.1 binding site was investigated using the human monocyte cell line Thp-1. Although less active than construct −86, construct −48 showed enhanced promoter activity relative to construct −46. Mutations at bp −48 had little effect, whereas mutations of nucleotide G at bp −46 and/or T at −47 dramatically reduced both PU.1 binding and promoter activity. The PU.1 binding avidity of these sequences correlated closely with their capacity to dictate reporter gene transcription. Analogous studies of the promoter of CD 18, another PU.1-regulated myeloid-specific gene, showed that mutations of the corresponding G and T residues reduced PU.1 binding and nearly abolished promoter activity. The immediate upstream flanking sequences of the PU.1 consensus motif are important and their significant effects on myeloid gene promoter activity are determined by their influences on PU.1 binding avidity. Specific flanking nucleotides both 5' and 3' from the core, as well as core binding residues, form a critical PU.1 binding array.

Cooperation between PU.1/HAF1, Sp1 and AP-1 of p67$^{phox}$ promoter in phagocytes: The myeloid-specific transcriptional regulation of p67$^{phox}$, an essential component of phagocyte respiratory burst NADPH oxidase, was investigated. Analysis was carried out on the p67$^{phox}$ 5'-flanking region from −3669 to −4 (relative to ATG), including the first exon and intron and part of the second exon. The construct extending from −985 to −4 produced the highest luciferase activity in myeloid HL-60 cells, but was not active in HeLa or Jurkat cells, indicating myeloid-specific expression. Four active elements were identified: Sp1/Sp3 at −694, PU.1 at −289, AP-1 at −210, and PU.1/HAF1 at −182, the latter three being in the first intron. These cis elements bound their cognate transacting factors both in vitro and in vivo. Mutation of the Sp1, PU.1, or PU.1/HAF 1 site each decreased promoter activity by 35-50%. Mutations in all three sites reduced promoter activity by 90%. However, mutation of the AP-1 site alone nearly abolished promoter activity. The AP-1 site bound Jun and Fos proteins from HL-60 cell nuclear extract and in the intact cells as demonstrated by chromatin immunoprecipitation (ChIP) assay. Co-expression with Jun-B in AP-1-deficient cells increased promoter activity. These data showed that full $p_{67}^{phox}$ promoter activity requires cooperation between myeloid-specific and broad transcription factors, with AP-1 being most critical for function.

Multiple PU.1 binding sites contribute to the $p40^{phox}$ promoter activity: The $p40^{phox}$ protein, a regulatory component of the phagocyte NADPH oxidase, is preferentially expressed in cells of myeloid lineage. Transcriptional regulation of the $p40^{phox}$ gene was investigated in HL-60 myeloid cells. Deletion analysis of ~6 kb of the 5'-flanking sequence of the gene demonstrated that the proximal 106 bp of the promoter exhibited maximum reporter activity. This region contains three potential binding sites for PU.1. Mutation or deletion of each PU.1 site decreased promoter activity and the level of activity mediated by each site correlated with its binding avidity for PU.1, as determined by gel shift competition assays. Mutation of all three sites abolished promoter activity in myeloid cells. ChIP assays demonstrated occupation of the PU.1 sites by PU.1 in vivo in HL-60 cells. Co-transfection of the pGL3-p40-106 reporter construct with a dominant-negative PU.1 mutant dramatically reduced promoter activity, whereas overexpression of PU.1 increased promoter activity. The $p40^{phox}$ promoter activity and transcript levels were increased in HL-60 cells during DMSO-induced differentiation towards a granulocyte phenotype and this was associated with increased cellular levels of PU.1 protein. These findings demonstrate that PU.1 binding at multiple sites in the proximal region is required for $p40^{phox}$ gene transcription in myeloid cells.

Construction of a synthetic promoter library: Myeloid-specific cis promoter elements for PU.1, C/EBPα, and AML-1 and myeloid-associated cis promoter elements for Sp1 and AP-1 (38-41) were chosen for the promoter libraries. There are two different categories of PU.1 binding sites, GAGGAA and GGAGAA. Both were chosen and designated as PU.1A and PU.1B, respectively. Native sequences adjacent to the core motif of each cis regulatory element were included to avoid loss of potentially important sequences (Table 3). The synthetic promoter element oligonucleotides were 20 or 30 base pairs in length, such that regulatory elements would appear on the same face of the DNA helix when reassembled. Double-strand oligo-nucleotides of PU.1A, PU.1B, C/EBPα, AML-1, Sp1, and AP-1 promoter elements with a ratio of 2:2:2:2:1:1 were randomly ligated and products were gel separated. DNA fragments 100-500 bp in length were collected and ligated to a NheI linker, which also contained an Sp1 element for protection of CpG islands and also non-island DNA regions from de novo methylation. The resulting DNA was then inserted into the pGL3-p47-86 plasmid at the NheI site to generate synthetic promoter libraries. Other basal promoters, such as the CD68 basal promoter, could also be used.

Screening for synthetic promoters with strong activity: To measure the strength of the synthetic promoters, the in vitro luciferase activity was assayed for more than 200 different clones in 24-well plates containing transiently transfected human Thp-1 monocytic cells. The cytomegalovirus (CMV) basic promoter was used as a ubiquitous promoter control. PGL3-p47-86 was used as a basal activity control. Thirty-eight independent clones showing promoter activity at least 5-fold higher than the basal control were confirmed by repeating experiments. Ten of these were sequenced (FIG. 1) and characterized further.

Macrophage-specific activity of the super-promoters: The specificity of the super-promoters was evaluated by transient transfections in several macrophage and non-macrophage cell lines. In human monocytic cell Thp-1, Mono Mac-1, mouse macrophage cell RAW264.7, J774, and WEHI-3, luciferase activity of the super-promoters was extremely high, 10-200-fold over that of the CSF1R (42) or CD11b (43) promoters. In contrast, in human intestinal epithelial cell Caco-2, cervix epithelioid carcinoma cell HeLa, embryonic kidney cell 293, T lymphocyte Jurkat, and mouse osteoblasts Oct-1, specific luciferase activity of the super-promoters was quite low compared with the CMV promoter.

In vivo activity of the super macrophage promoters: Selected synthetic promoters were subcloned into the pEGFP-C1 vector (Clontech) where CMV promoter had been removed. An in vivo gene delivery system (TransIT™) developed by Mirus Corporation (Madison, Wis.) was used. Ten micrograms of one of the most potent synthetic promoter-EGFP constructs (pEGFPC1-SP-144) and the pEGFP-C1 vector were injected into the tail vein of Balb/c mice. Twenty hours later, the mice were sacrificed and liver leukocytes isolated. The isolated cells were reacted with APC-conjugated antibody to CD11b and then subjected to FACS analysis. As shown in Table 1, there is little difference between the numbers of GFP(+)/CD11b(+) cells driven either by ubiquitous active CMV promoter or by the macrophage promoter, while there is a significant difference (p<0.01) between the numbers of GFP(+)/CD11b(−) cells driven by the two promoters. CD11b served as a macrophage marker. This result demonstrates the in vivo great macrophage specificity and strength of the selected synthetic promoter.

In vivo promoter activity was also investigated with the use of bone marrow transplantation (BMT). The method of Pawliuk (Pawliuk et al., 2001) was adapted to transduce HSC with lentiviral vectors, while leaving their stem cell nature unchanged, to levels of efficiency sufficient for pan-target cell expression of therapeutic genes. Briefly, bone marrow cells were harvested from donor mice, treated with Lympholyte-M (CedarLane Laboratories, Hornby, Ontario, Canada) to enrich for hematopoietic stem cells, pre-cultured overnight with cytokines, and transduced in 0.85 ml of culture with concentrated lentiviral super-promoter (SP)-EGFP for 6 hours. Approximately $10^6$ cells were transplanted by i.v. injection into lethally irradiated (950 cGy of total body irradiation) recipient mice. At week 10 post-transplantation, GFP expression in peripheral blood was analyzed by FACS. Using CD11b/Mac-1 as a macrophage/myeloid marker, it was shown that GFP expressed strongly (~$2\times10^3$ relative units) in monocytes/macrophages, but weakly (~$6\times10^1$ relative units) in some Mac-1 negative leukocytes. GFP also expressed at moderate levels in a fraction of Mac-1 positive neutrophils. These data demonstrate strong macrophage-specific activity of these promoters.

Dopamine uptake after MPTP treatment in the mouse striatum: High-affinity synaptosomal dopamine uptake is a sensitive quantitative indicator of dopaminergic axonal terminal density. Determination of dopamine uptake at various times after MPTP treatment revealed an initial comparable loss in dopamine uptake levels in both age groups in the dorsal as well as in the ventral striatum. In the dorsal striatum, MPTP produced a significant reduction in dopamine uptake levels at 4 d after MPTP in young (8 weeks old) and middle-aged (8 months old) mice (59 and 41% of control, respectively). A reduction in dopamine uptake levels in the dorsal striatum was still observed at 8 and 14 d in both age groups. However, between 14 and 30 d, a significant recovery in dopamine uptake levels was observed in young mice. Dopamine uptake levels increased to 87% of control levels after MPTP treatment in the dorsal striatum of young mice, whereas older mice did not exhibit such recovery.

Dopaminergic neuronal degeneration in mice after MPTP treatment: The use of TH-IR neuronal counts has not been a reliable method to measure for MPTP-induced degeneration of dopaminergic neurons. It was shown that MPTP can cause a loss in TH expression without producing neuronal death (Jackson-Lewis et al., 1995). To determine whether SN dopaminergic neurons are in fact degenerating after MPTP treatment, SN cells were prelabeled with fluorescent microspheres before MPTP administration. The mice were sacrificed 8 d after saline and MPTP treatment, and midbrain sections were reacted with antibodies to TH and Mac-1, a microglia marker specific for the mouse. In saline-treated mice, retrogradely transported fluorescent microspheres labeled the cell body of a subpopulation of TH-IR neurons in the SN. In MPTP-treated mice, although some fluorescent microspheres were found in TH-IR neurons, they were also found to be aggregated and scattered throughout the SN. Mac-1-IR cells with internalized fluorescent microspheres were found at the level of the SN cell bodies, suggesting that microglia are phagocytosing degenerating SN dopaminergic neurons.

Figure 2:
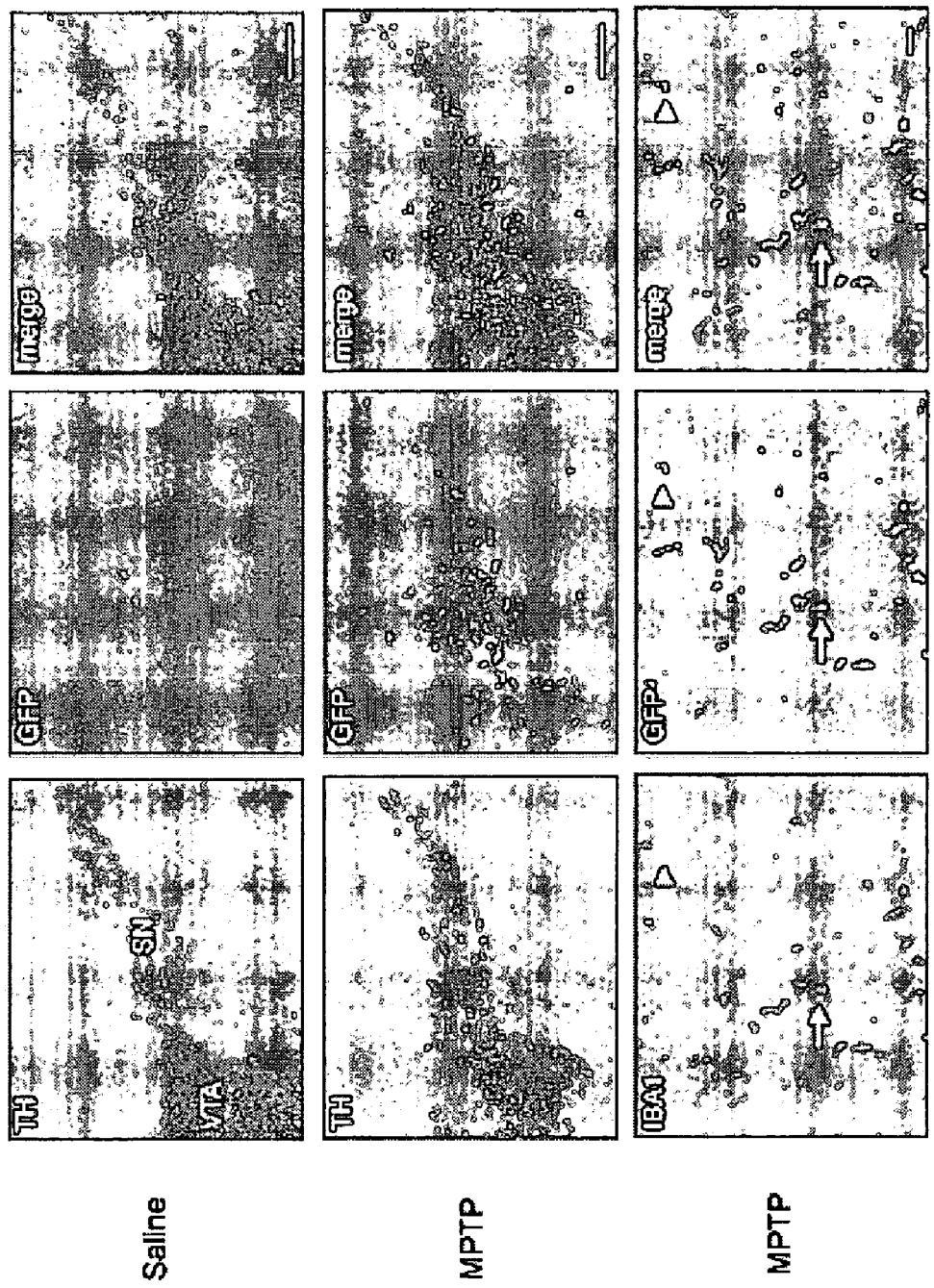
FIG. 2. Immunohistochemistry of coronal sections showing the substantia nigra (SN) and ventral tegmental area (VTA) from bone marrow transplanted mice 7 days after saline or MPTP treatment. The location of the dopaminergic neurons identified by TH immunoreactivity and infiltrating GFP labeled cells after saline and MPTP treatment is shown. Following MPTP lesion, the infiltrating GFP labeled cells are seen predominantly in the substantia nigra, the specific location of the MPTP injury. 50-60% of GFP positive cells are shown to express the macrophage and microglial marker IBAL (shown by arrow). IBA1 negative, GFP positive cells are shown by arrowhead.

Bone marrow-derived macrophages/microgliocytes accumulation in the SN of MPTP treated mice: Bone marrow cells collected from C57B/6 EGFP transgenic mice were transplanted into lethally irradiated 6-week old mice. Five weeks post transplantation, a group of 5 randomly selected recipient mice received a dose of 4×13 mg/kg body weight of MPTP-HCl injected subcutaneously at 2 hr intervals. One week after MPTP administration, the mice were intracardially perfused first with PBS, PH 7.4, followed by 4% phosphate-buffered paraformaldehyde (PFA, pH 7.4) for 10 minutes. The brains were removed and post-fixed in 4% PFA overnight and then cryoprotected in 30% sucrose. The tissues were frozen and sectioned at 20 μm for a total of 75 serial sections on a cryostat. For immunohistochemistry, the sections blocked with normal goat and/or donkey serum were incubated with the following primary antibodies: Ibal, 1:500 (Wake Pure Chemicals); TH, 1:1000 (Novus); GFAP, 1:50 (Biomeda); and Gr-1, 1:50 (Pharmingen). Fluorescently conjugated secondary antibodies (Texas Red-goat anti rabbit, Texas red-donkey anti rat) were from Jackson Immuno Research. The images were taken with a computer-assisted image analysis system equipped with a digital camera (Zeiss Axioplan 2 photomicroscope). As shown in FIG. 2, following MPTP lesion, the infiltrating GFP positive cells are seen predominantly in the substantia nigra, the specific location of the MPTP injury. Up to 60% of GFP positive cells were identified as macrophage/microglia.

Glial cells transduced with GDNF expressing lentivectors secret GDNF protein: Human and mouse GDNF were separately inserted into Lenti-SMP-GFP to replace the EGFP gene. The resulting constructs, Lenti-SMP-hGDNF, Lenti-SMP-mGDNF, and the parent vector Lenti-SMP-GFP were each co-transfected together with the three packaging plasmids to produce viral particles. While GDNF protein was almost undetectable in the medium where cells were cultured without the virus, the GDNF concentration was ~2.65 ng/ml and ~1.15 ng/ml in the medium of lentiviral vector-infected C6 and 293T cells, respectively, indicating that the lentivirus-carried GDNF transgene is highly produced and secreted.

The synthetic promoters described above are highly active in macrophages/myeloid cells, but inactive or weakly active in other blood cell lineages in bone marrow recipient mice. A complete characterization of these promoters is done in transgenic mouse models. Recent findings that bone marrow stem cells (probably mesenchymal stem cells) can trans-differentiate into and/or fuse with various non-hematopoietic cell types such as neurons and endothelial cells (Jiang et al., 2002; Hubner et al., 2003; Horwitz et al., 2002; Kozorovitskiy and Gould, 2003) allow for the full characterization of these super-promoters in vivo. EGFP is used as a reporter gene. The EGFP gene encodes a protein with a single red-shifted excitation peak and 30- to 40-fold more fluorescence intensity than wild-type GFP when excited at 488 nm (Shariatmadari et al., 2001).

In consideration of moving into clinical trials, both human and murine GDNF genes are used in the proposed study. The genes are also flag-tagged to facilitate detection. The flag sequence has been shown not to interfere with GDNF activity (Wang et al., 2002). The murine and human GDNF protein sequences are highly similar, and exhibit cross-species activity (Gouhier et al., 2002; Ugarte et al., 2003; Wang et al., 2002).

For MPTP administration, either a single injection (55 mg/kg) or multiple (4×14 mg/kg) subcutaneous injections is used. A single administration of MPTP can lead to some mortality in the experimental animals. Multiple administrations are much better tolerated.

The super macrophage promoters are characterized using 1) transplantation of bone marrow stem cells transduced ex vivo with lentiviral vectors and 2) expression in transgenic mice using EGFP (enhanced green fluorescent protein) as a reporter.

Lentiviral vector construction The replication incompetent third generation lentivectors are gifts from Dr. Didier Trono (Geneva, Switzerland) (Miyoshi et al., 1998) and Dr. Nakauchi (Tsukuba, Japan) through Dr. Inder Verma (Salk Institute) (Tahara-Hanaoka et al., 2002). They are self-inactivating, stripped of all HIV accessory proteins, and are strictly dependent on complementation of Rev protein in trans. The CMV or EF-1α promoter upstream of EGFP reporter gene is replaced with the testing promoters. The resulting constructs are designated Lenti-SMP-EGFP where Lenti represents lentivector and SMP represents super macrophage promoter. Lenti-SMP-EGFP viral particle production, bone marrow stem cell collection, enrichment, ex vivo transduction, and transplantation are done as described herein. The commercially available lentivirus from Invitrogen can also be employed in the compositions and methods described herein.

Construction of synthetic promoter-EGFP reporter transgene The current pEGFPC1-SP constructs are modified so that the transcriptional unit will be flanked by a 1.2 kb DNA fragment of chromatin insulator (a gift from Dr. Felsenfeld, NIH, Bethesda) (Bell et al., 1999; Recillas-Targa et al., 1999) to avoid gene silencing. In the construction process, restriction enzyme sites are included to facilitate release of the transgene DNA fragment that contains the least vector sequences. Two or three promoters selected by the bone marrow cell ex vivo transduction and transplantation method are modified for making transgenic mice. Plasmid DNA is prepared either by Qiagen EndoFree™ Plasmid kit or by banding twice on CsCl gradients to ensure DNA quality. Alternatively, Lenti-SMP-EGFP viral particles are used to infect murine ES cells and make transgenic mice directly (Pfeifer et al., 2002).

Generation of SP-EGFP transgenic mice. The DNA is injected into C57BL6/J zygotes at a concentration 3 ng/μl. Transgenic founder mice are identified by PCR and the results confirmed by Southern blotting. Founder mice are mated with C57BL/6 mice, and progeny screened 3-4 weeks of age for the presence of the transgene by PCR using genomic DNA isolated from tail biopsy samples. They are bred to homozygosity before experimentation to reduce the work load in the later identification of transgene-bearing mice, and to eliminate variation of gene expression introduced by genomic volume (Hahn et al., 1998).

Assessment of transgene copy number by Southern blotting The copy number of a transgene has been shown to contribute to the subsequent levels of gene expression (Rhoades et al., 2000; Fedorov et al., 2001). Although it is hard to predict, higher copy number often leads to higher expression levels. Therefore, the copy number of the transgene is determined by comparison with defined amounts of the DNA used for pronuclear injections.

Isolation of leukocytes peritoneal cells, bone marrow, and splenocytes Peripheral blood leukocytes are isolated by separation in Ficoll-Hypaque gradients, hypotonic lysis in 0.15 mmol/L $NH_4Cl$, 1 mmol/L $KHCO_3$, 0.1 mmol/L EDTA, followed by washing in PBS. Peritoneal cells are isolated by peritoneal lavage with 20 ml PBS at times indicated after the intraperitoneal administration of 1 ml of a 10% solution of thioglycollate (DIFCO, Detroit, Mich.). Bone marrow is flushed from femurs and tibias with PBS (Hahn et al., 1998; Dziennis et al., 1995). Splenocytes will be isolated using 70 μm cell strainers (FALCON). Spleen tissue is rubbed into 5 ml tissue cell wash buffer (DMEM medium containing 2% FCS, 1% P/S, 10 mM HEPES). To collect the single-cell suspension, the tube is placed in ice for 5 min, the supernatant transferred to a fresh tube, and 1 ml of red blood cell lysis buffer (Sigma) is added for 1-3 min to lyse the red blood cells. The remaining spleen cells are adjusted to $2 \times 10^6$/ml for immunofluorescence staining (Back et al., 1995).

Immunofluorescence staining and FACS analysis for the co-expression of EGFP with leukocyte markers To detect macrophage/monocytes, neutrophils and T cells, CD11b or CD68, Gr-1, and CD4, respectively, are used as cell surface markers, using either direct or indirect immunofluorescence staining. For CD11b on macrophage/monocytes, Gr-1 on neutrophils and CD4 on T cells, direct immunofluorescence staining is used. $10^6$ cells are washed in cold PBS containing 0.5% BSA (0.5% BSA/PBS), and incubated with either specific conjugated anti-mouse antibody or the corresponding conjugated $IgG_{2\alpha}$ (control) for 15 min at 4° C. in 100 μl 0.5% BSA/PBS. After washing, cells are subjected to FACS analysis immediately, or by using 1% formalin to fix cells, the analysis can be done the next day. The antibodies used include APC-conjugated anti-mouse CD11b, PerCP-conjugated anti-mouse CD4 and PE-conjugated anti-mouse Gr-1. As controls, the corresponding conjugated immunoglobulin isotype is used. FITC-conjugated antibody is not used because of interference with the green fluorescence of GFP. To detect CD68 on macrophage/monocytes, indirect immunofluorescence is used. $10^6$ cells will be stained by a BAC immunostaining system, using goat anti-mouse CD68 (polyclonal IgG), biotin-conjugated rabbit anti-goat Ig and APC-conjugated streptavidin in that order. Cells are washed after each step in PBS (Blum, 1998; Ho and Blum, 1998).

Detection of EGFP in frozen sections by fluorescence and confocal microscopy using a slow freezing protocol Animals are anesthetized with Rompun, xylazine and Ketaset (1:1) and killed by intracardiac perfusion with 1% paraformaldehyde in 0.15M phosphate buffer, pH 7.2 (PBS), followed by 4% paraformaldehyde. Tissues are dissected, washed once in PBS, and embedded in Tissue-Tek at room temperature. The embedded tissues are kept in the dark at 4° C. for 34 h and then slowly frozen at −70° C. in a box covered with cotton wool. The tissues can be stored at −70° C. before sectioning. The fluorescent light emitted by EGFP is evaluated by confocal microscopy (Olympus FluoView™ 500). The tissue sections are exposed to a 488 nm excitation wavelength and emission obtained at 500-520 nm. Ten images with 2 μm intervals in the z-axis are collected (Shariatmadari et al., 2001).

Northern blot analysis RNA is size-fractionated on 1.0% agarose gels containing 2.2 M formaldehyde and transferred to nylon membranes (GeneScreen Plus™; NEN DuPont) by using a transblot apparatus (Bio-Rad) in 10×SSC (1×SSC is 0.15M NaCl and 0.015M citrate). Blots are hybridized overnight to radiolabeled probes in the presence of 1% SDS, 10% dextran sulfate, 1 mM NaCl, and 50% formamide at 42° C. After hybridization, membranes are washed twice with 2×SSC for 5 min each at room temperature, twice with 2×SSC containing 1% SDS or 0.1% SDS at 60° C. for 30 min, and twice with 0.05×SSC at room temperature for 15 min prior to autoradiography.

Western blot analysis Western blotting is used to monitor EGFP expression in various tissues. Animals are sacrificed and their hearts, livers, spleens, lungs, kidneys, and brains dissected and lysed in extraction buffer (40 mM Tris, pH 6.8, 2% 2-mercaptoethanol, 1% SDS, 5% glycerol, 10 mM EDTA, 50 μg/ml aprotinin, 50 μg/ml leupeptin, 500 μg/ml Pefabloc and 10 μg/ml pepstatin A). Samples are boiled for 5 min and insoluble debris removed by centrifugation for 3 min at 12,000 g. The protein concentration of the cleared supernatant is determined using the DC Protein Assay kit (BioRad Labs., Hercules, Calif.). Extracted cellular proteins (80 μg/sample) are fractionated by SDS-PAGE and electrophoretically transferred to nitrocellulose (BA85; 0.45 μm, Midwest Scientific, Valley Park, Mo.). Blots are pretreated in PBS blocking buffer (5% NFDM, 0.2% Tween-20 in PBS) for 1 h at 23° C. and then incubated in blocking buffer for 2 h at 23° C. with a polyclonal anti-EGFP (Clontech). Antigen-antibody complexes are visualized by enhanced chemiluminescence (SuperSignal kit, Pierce, Inc., Rockford, Ill.).

Amelioration of neurodegeneration in the MPTP (1-methyl-4-phenyl-1,2,3,6-tetrahydropyridine) mouse model of Parkinson's disease by syngeneic transplantation of HSC transduced ex vivo with lentivectors expressing GDNF gene in macrophages/microglia driven by the SMP.

Mice Mice are given drinking water with 100 mg/liter neomycin and 10 mg/liter polymyxin B for 3 days before and 14 days after transplantation.

Lentiviral vector construction Human and mouse GDNF cDNA is separately inserted into Lenti-SMP-GFP to replace the EGFP gene. The GDNF is either tagged by a flag sequence (DYKDDDDK, SEQ ID NO:1) at the carboxyl terminus or not. The resulting constructs are named Lenti-SMP-hGDNF, Lenti-SMP-hGDNFflag, Lenti-SMP-mGDNF and Lenti-SMP-mGDNFflag. The flag sequence has been shown not to interfere with GDNF activity.

Lentiviral vector production VSV-G-pseudotyped lentiviral particles are generated by transient cotransfection of plasmid DNA of the transfer vectors (Lenti-SMP-hGDNF, Lenti-SMP-hGDNFflag, Lenti-SMP-mGDNF, Lenti-SMP-mGDNFflag and the parent vector Lenti-SMP-GFP) with the three packaging plasmids (pMDLg/pRRE, the gag-pol plasmid; pRSV-Rev, a Rev expressing plasmid; and pMD.G, a VSV-G envelope expressing plasmid) into 293T cells as described. Lentivector supernatant is filtered, concentrated by twice ultracentrifugation (55,000 g for 3 hours), and stored at −70° C. (Imren et al., 2002; Pawliuk et al., 2001). The viral titers are estimated by transduction of 293T cells with the CMV-EGFP lentivector processed simultaneously.

Bone marrow cell culture lentiviral infection, and transplantation Isolation, transduction, and transplantation of murine bone marrow (BM) cells is as described (Pawliuk et al., 2001). Briefly, BM is obtained from femurs and tibias of 6- to 8-week-old male mice 4 days after i.v. injection of 5-FU at a dose of 100 mg/kg body weight. Bone marrow cells are treated with Lympholyte-M (Gibco, Cat # 10639-011) for enrichment of HSCs, and stimulated overnight in StemPro medium along with 6 ng/ml of IL-3, 10 ng/ml of IL-6, 10 ng/ml of murine IL-1α and 100 ng/ml of Stem Cell factor. The next day, cells are pelleted and resuspended in 0.85 ml of the aforementioned medium containing the same growth factor combination with concentrated VSV glycoprotein G-pseudotyped SP-LXR lentivectors at a final virus concentration of $2-10 \times 10^9$ infectious units/ml. Infection is performed for 6 h on fibronectin-coated Petri dishes in the presence of 8 μg/ml protamine sulfate. After infection, $2 \times 10^6$ cells are transplanted, without selection, by i.v. injection into each syngeneic recipient given 950 cGy of total body irradiation.

Secondary bone marrow transplantation (BMT) Secondary BMT is performed to confirm that integration of functional lentivector provirus has occurred in reconstituting stem cells. BM from primary recipients is harvested 4 to 8 months post-transplantation and used for secondary transplants (Bjorgvinsdottir et al., 1997).

Real-time PCR analysis of proviral copy number Vector copy number in mouse peripheral blood cells is determined by real-time quantitative TaqMan polymerase chain reaction (PCR) (PE Applied Biosystems, Foster City, Calif.). Primers and probes completely within the extended LTR lentivector sequence that can be used regardless of the transgene are used. Forward primer, TGAAAGCGAAAGGGAAACCA (SEQ ID NO:2); 6FAM-labeled probe, AGCTCTCTC-GACGCAGGACTC (SEQ ID NO:3); reverse primer, CCGT-GCGCGCTTCAG (SEQ ID NO:4). The following incubation periods are applied: 2 min at 50° C., 10 min at 95° C., 40 cycles of 15 sec at 95° C., and 60 sec at 60° C. Standard curves for the TaqMan PCR analyses are obtained by using vector single-copy clones of NIH 3T3 cells transduced with the lentiviral vector. (Roesler et al., 2002).

Examination of GDNF expression and secretion in SNpc and striatum. At different time points post-MTPT treatment, animals are anesthetized and killed by intracardiac perfusion with 1% paraformaldehyde followed by 4% paraformaldehyde. After post-fixing, twenty-micrometer coronal frozen brain sections are processed for immunohistochemistry. Sections are incubated in blocking buffer, followed by incubation overnight with primary antibodies to flag or GDNF and TH (dopaminergic neurons marker) or IBA1 (macrophage/microglial marker). After washing, sections are incubated in biotinylated anti-IgG to primary antibody for 2 hr at room temperature and incubated in ExtraAvidin (usually 1:1000) for 1 hr. Samples are washed and processed with 0.05% 3,3'-diaminobenzidine tetrachloride with 0.003% $H_2O_2$. Sections are washed, mounted on coated slides and examined under a light microscope.

Striatum GDNF assay by ELISA Striatum is collected at different time point post-MPTP treatment. Each striatum is dissected separately using clearly defined landmarks and homogenized in lysis buffer containing 137 mM NaCl, 20 mM Tris-HCl (pH 8.0), 1% NP40, 10% glycerol, 1 mM phenylmethylsulfonyl fluoride (10 μg/mL), and 0.5 mM sodium vanadate. Homogenate is centrifuged at 12,000 g for 20 min at 4° C. Supernatants are removed, acid-treated with 1M HCl (1 μL/10 μL of sample), and then neutralized with 1M NaOH (1 μL/10 μL of sample) to increase the sensitivity of the assay (Okragly and Haak-Frendscho, 1997). Samples are assayed for GDNF protein using an ELISA kit (Promega) according to the protocol provided.

MPTP treatment MPTP hydrochloride is dissolved in physiological saline. Four weeks post-BMT, a group of eight randomly selected recipient mice receive a dose of 4×14 mg/kg MPTP injections subcutaneously at 2 hr intervals.

Coordination Testing on a Rota-Rod Mice are trained twice on two consecutive days for a 5-min period at low speed (3 rpm) to become accustomed to the accelerating rotarod (Columbus Instruments). On the third and fourth days, they are placed on the rotarod at accelerating speeds from 3 to 50 rpm (increments of 5 rpm/30 sec) and tested four times with a 5-min break between tests. The mice are kept on the apparatus for a maximum of 280 sec. The time each mouse remains on the rod is registered automatically. For each mouse, a single measurement is calculated to represent the average performance of four attempts and be presented as latency to fall. All testing is performed between 2 and 5 p.m. (Hahn et al., 1998).

PET imaging of [$^{18}$F]Dopamine uptake Recent advances in in vivo imaging techniques have allowed use of dedicated positron emission tomograghy (PET) instrumentation with high-resolution and signal sensitivity in applications involving a small animal model. In vivo dynamic imaging of [$^{18}$F] Dopamine uptake in the MPTP mouse model of Parkinson's disease will be studied. $^{18}$F-6-fluorodopa ($^{18}$F-dopa) PET is a marker of presynaptic dopaminergic terminal function and reflects dopa transport into the terminal, dopa decarboxylase activity, and dopamine storage capacity and has been used extensively to assess dopamine changes in clinical Parkinson's disease (Brooks, 2003).

$^{18}F_2$ preparation and radiolabeling of dopamine $^{18}F_2$ is produced from 0.2% $F_2$ in Neon with a cyclotron. [$^{18}$F] Dopamine is synthesized by a published method. The radiolabeling efficiency is determined by integrating areas with High Pressure Liquid Chromatography (HPLC) and calculating the percentage of radioactivity associated with the [$^{18}$F] Dopamine peak.

In vivo microPET imaging scans The microPET-R4 rodent scanner (Concorde Microsystems, Knoxville, Tenn.) contains four rings of 24 detectors and each detector consists of a lutetium orthosilieate crystal block (2×2×1 cm) that is subdivided into an 8×8 matrix. The scanner provides a 10 cm by 8 cm field of view, and the scanner is currently capable of an axial and transaxial resolution of 2 mm, with an absolute sensitivity of 900 counts per second per μCi. This resolution allows for distinguishable head imaging of the stratum tissue (~2.5 mm) of the MPTP mouse model. Images are reconstructed using Fourier rebinning followed by two-dimensional filtered back projection. During imaging experiments, mice are injected with [$^{18}$F]Dopamine by lateral tail vein under anesthesia with 1-2% vaporized isofluorane. Data are collected continuously for 0-90 min. Specific activity of delivered doses is determined by counting each sample syringe prior to and following injection using a dose calibration instrument (Radioisotope Calibrator CRC-12, Capintec Inc., N.J.). Quantitation is performed by viewing regions of interest over the selected tissues and averaging the activity concentration over the contained voxels. [$^{18}$F]Dopamine influx constants (Ki) is calculated based on the parametric imaging data.

Counting of dopaminergic neurons Animals are anesthetized and sacrificed by transcardiac perfusion first with phosphate buffered saline (PBS, PH 7.4) followed by 4% phosphate-buffered paraformaldehyde (PFA, pH 7.4) for 10 minutes. The brains are removed and post-fixed in 4% PFA at 4° C. overnight and then cryoprotected in 30% sucrose. The tissues are frozen and sectioned at 50 µm on a cryostat for unbiased counting of dopaminergic neurons in SNpc with a Stero-Investigator.

For immunohistochemistry, the sections are rinsed and floated in PBS, then blocked with 0.3% Triton X-100 and 3% normal goat serum in PBS for 30 min followed by incubation with rabbit polyclonal anti-TH antibody(1:500; Pel-Freeze Biologicals) overnight. Then sections are washed for 3×10 min with PBS and incubated in biotinylated goat anti-rabbit IgG for 2 hrs at room temperature. Then sections are washed for 3×10 min with PBS and incubated in peroxidase conjugated-Extravindin (1;1000, Sigma) for 1 hr at room temperature followed by a 5-min-incubation with 0.05% 3,3'-diaminobenzidine tetrachloride (Sigma) and 0.03% H2O2 in PBS. After processing, sections are washed in distilled water, dehydrated through graded alcohols, cleared in xylene, and coverslipped in mounting medium (Electron Microscopy Sciences). The number of TH-IR neurons is determined by counting every other section from sections covered the whole length of SNpc in midbrain at a magnification of 100×.

[$^3$H]Dopamine uptake Animals are decapitated, and the brains quickly removed into cold sterile saline. Dorsal, ventral striatum and ventral midbrain are separated carefully. Then tissues are homogenized in 500 µl of ice-coldprelysis buffer (10 mM Tris, pH 7.5, and 0.32M sucrose) using a Teflon pestle-glass mortar pair. Homogenized tissue is removed and centrifuged for 10 min at 1000 g at 4° C. to remove nuclei. The supernatant containing the synaptosomes is collected, and aliquots removed for the determination of protein concentration and dopamine uptake (total high-affinity and mazindol noninhibitable). Fifty microliters of supernatant is diluted in 450 µl of Krebs-Ringer phosphate buffer (0.1M) with added EDTA (1.3 mM), glucose (5.6 mM), and ascorbic acid (0.2 mg/ml) and incubated at 37° C. in the presence or absence of 10 µM mazindol (Research Biochemicals), a high-affinity dopamine uptake inhibitor. [$^3$H]Dopamine (specific activity, 20-40 Ci/mmol; Amersham, Arlington Heights, Ill.) is added to a final concentration of 0.025 µM, and incubation is at 37° C. for 6 min. Synaptosomes are collected on presoaked nitrocellulose filters by filtration, and nonspecific radioactivity is washed with Krebs-Ringer phosphate buffer followed by filtration. The filters are transferred into scintillation vials of Hionic-fluor and measured by liquid scintillation spectrometry. Specific high-affinity neuronal dopamine uptake is expressed as femtomoles of dopamine uptake per microgram of protein minus the femtomoles of mazindol uptake. Values are presented as the change in dopamine uptake (Ho and Blum, 1998).

Western blot analysis of TH expression Striatum and ventral midbrain are cut from blocks of brain tissue frozen at −80° C., then individually homogenized in RIPA buffer (0.1M PBS, 1% non-ionic detergent (Igepal), 0.5% sodium deoxycholate, 0.1% sodium dodecyl sulfate, 1 mM dithiothreitol) containing the protease inhibitors phenyl-methlsulfonyl fluoride (0.1 mM), leupeptin (2 mg/ml), and aprotinin (4.6 mg/ml). After incubation in buffer for 30 min at 4° C., samples are centrifuged at 10,000 g for 10 min at 4° C. Supernatants are collected and protein concentration is determined. A 30 mg sample of total protein is denatured for 5 min in sample buffer (0.125M Tris-HCl, pH 6.8, 4% sodium dodecyl sulfate, 20% glycerol, 10% β-mercaptoethanol and 0.006% bromophenol blue), electrophoresed onto a 7% SDS-PAGE, and transferred to a Hybond ECL nitrocellulose membrane (Amersham Pharmacia Biotech UK, Buckinghamshire, UK). To verify the quality and equal concentration of the proteins in the filter, staining with Ponceau S is carried out. The blot is washed in Tris-buffered saline containing 0.05% Tween 20, saturated with 5% bovine serum albumin and 5% skim milk for 1 h and incubated overnight at 4° C. with TH-mouse monoclonal antibody (Roche Diagnostics, Mannhein, Germany) diluted 1:2000. After washing, the blot is incubated with horse anti-mouse IgG linked with peroxidase (Roche Diagnostics, Mannhein, Germany), diluted 1:2000, for 1 h. The reaction is developed using an ECL chemiluminescence method.

Tyrosine hydroxylase assay Each striatum is homogenized in 50 mM Tris buffer (pH 7.4) also containing 1 mM EDTA and 0.2% Triton X-100, and TH activity is measured (Morgan et al., 1975; Morgan and Nelson, 2001). An aliquot of each homogenate is saved for subsequent analysis of protein concentration using the method of Bradford. To chemically cleave the $^{14}$C-labeled carboxyl group from the radiolabeled-dihydroxyphenylalanine, 25 µl of a 16.9 mM iodotyrosine-240 mM ethylmaleimide solution is added to each sample tube (10×75-mm, glass) immediately following the 20-min 37° C. incubation step. Each tube is incubated at room temperature for 30 min and then 25 µl of a 33.3 mM solution of potassium ferricyanide added. Each incubation tube is dropped in a 15-ml glass tube, and the latter is sealed with a rubber cap. A plastic basket containing 50 µl of Protosol and a paper wick is suspended from this cap. Each TH assay and each protein assay is performed in duplicate. Tyrosine hydroxylase activity is expressed as nanomoles (nmol) of carbon dioxide ($CO_2$) generated per hour per gram of protein.

Double immunolabeling Young mice are lesioned with MPTP and killed at 8 d, along with a saline-matched control, and processed for combined fluorescence immunocytochemistry for GDNF or flag and IBA1 (macrophage/microglial marker). Sections are incubated in blocking buffer (0.3% Triton X-100 in PBS and 3% goat serum in PBS) for 30 min, followed by an overnight incubation of primary antibody (sheep-anti-GDNF, Biocompare and IBA1, Wake Pure Chemicals) in blocking buffer at 4° C. GDNF is visualized by incubation with donkey anti-sheep IgG directly conjugated to fluorescein (1:200), whereas IBA1 immunoreactivity is reacted to Texas Red-goat anti rabbit. After processing, sections are mounted on coated slides, dried, and coverslipped in Permafluor (Lipshaw, Pittsburgh, Pa.) mounting medium (Ho and Blum, 1998).

Catecholamine Analysis One striatum from each animal is homogenized in cold (4° C.) 0.1N perchloric acid ($HClO_4$) containing 1 mM sodium metabisulfite ($Na_2S_2O_5$) and 100 nM dihydroxybenzylamine (DHBA). The latter compound is used as an internal standard. Norepinephrine, DA, and DOPAC in duplicate aliquots of each striatal sample are extracted with alumina and subsequently analyzed by high performance liquid chromatography (Morgan and Nelson, 2001). Briefly, an Alltech Associates (Deerfield, Ill.) 5-micrometer, 15-centimeter reverse-phase column will is used to resolve the catecholamines, which is analyzed using a Waters Corporation (Milford, Mass.) Model 464 electrochemical (EC) detector. The potential on the EC electrode is set at +0.7 volts, and the mobile phase is a 75 mM phosphate buffer (pH 2.5) containing 25 micromolar (µM) EDTA (ethylenediaminetetraacetic acid), 2.3 mM octane sulfonate, and 5% acetonitrile. Protein concentration is determined in duplicate aliquots of each homogenate, and the concentration of each catecholamine is ultimately expressed as picomoles per milligram of protein (Morgan et al., 1975; Morgan and Nelson, 2001).

Detection of apoptotic neurodegeneration Cryostat sections are prepared at 20 µm thickness and sections mounted on slides. TUNEL reaction is carried out using ApopTag-Red™ (Intergen, Purchase, N.Y.) per manufacturer directions. The evidence shows that a single nuclear morphology is not sufficient to identify apoptosis and that cytochrome c, pro-caspase 9, and caspase 3 pathways are operative in PD nigral apoptosis. Active caspase-3 is examined by APO Active 3 detection kit (Cell Signaling Technologies).

Peripheral blood cell counts To examine whether the hematopoiesis is altered by the proposed manipulation, blood cell counts (hematocrit, white blood cell, differential, and reticulocyte counts) are determined at various times post-transplant using blood obtained from the tail vein. In some cases, blood is obtained either from the retro-orbital plexus or from the inferior vena cava postmortem for platelet counts (Bjorgvinsdottir et al., 1997).

Safety testing Genomic DNA from peripheral blood cells is screened for the presence of replication competent retrovirus by using a PCR assay to detect sequence encoding the envelope (Galimi and Verma, 2002; Roesler et al., 2002; Brenner and Malech, 2003).

Amelioration of neurodegeneration in the MPTP mouse model of Parkinson's disease by syngeneic transplantation of HSC transduced ex vivo with tetracycline-regulatable lentivectors expressing GDNF gene in macrophages/macroglio-cytes.

Lentiviral vector construction and ex vivo transduction Tetracycline-regulatable lentiviral vectors LV-TA1, LV-R1, and LV-TA1/R2 were provided by Dr. Vigna (Candiolo, Italy) (Vigna et al., 2002a). Whereas LV-TA1/R2 is a combined vector, LV-TA1 and LV-R1 constitute a two-vector Tet-off system and these need to be co-transduced in order to apply tetracycline regulated expression of reporter or therapeutic gene. Lentivector viral production, transduction of HSC, and bone marrow transplantation are done as described above.

Tetracycline administration Doxycycline (Dox) is used instead of tetracycline for advantages of dosing and stability. To prevent growth of bacteria or fungi, drinking water and drinking bottles are autoclaved and kept sterile as much as possible. To suppress GDNF expression, recipient animals receive Dox (1 mg/ml) plus 5% sucrose immediately after bone marrow transplantation in drinking water protected from light since Dox is light-sensitive. Higher doses may be chosen since the concentration may decrease through the blood-brain barrier. Trial experiments are done to determine the best dose and the time course of the increase in human GDNF protein levels (Rhoades et al., 2000).

MPTP treatment Four weeks after transplantation of ex vivo transduced bone marrow cells, mice of three different age groups are used: 8 weeks (young), 8 months (middle-aged), and 20 months (old) of age. MPTP hydrochloride (Research Biochemicals, Natick, Mass.) is administered subcutaneously. Young mice receive a single dose of MPTP of 55 mg/kg, middle-aged mice a dose of 40 mg/kg, and old mice a reduced dose. These doses are selected (and can be readjusted) mainly based on titration studies that produced comparable initial depletions of dopamine uptake in the striatum of young and middle-aged mice. Age-matched controls receive saline. GDNF expression is initiated by withdrawal of tetracycline before and at various times (e.g., 1, 4, 8, and 14 days) after MPTP administration. Animals are sacrificed at various time points after the lesion and GDNF expression is measured in these mice, along with their matched controls (n=5-8/group) (Ho and Blum, 1998).

Other procedures PET scan, rotarod test, neurodegeneration examination are done as described above.

Statistical Analysis ANOVA is used to examine any statistical difference among groups, followed by Newman-Keuls comparison or Bonferroni comparison analysis.

REFERENCE LIST FOR EXAMPLE 1

Aiuti, A., Slavin, S., Aker, M., Ficara, F., Deola, S., Mortellaro, A., Morecki, S., Andolfi, G., Tabucchi, A., Carlucci, F., Marinello, E., Cattaneo, F., Vai, S., Servida, P., Miniero, R., Roncarolo, M. G., and Bordignon, C. (2002). Correction of ADA-SCID by stem cell gene therapy combined with nonmyeloablative conditioning. Science 296, 2410-2413.

Akerud, P., Canals, J. M., Snyder, E.Y., and Arenas, E. (2001). Neuroprotection through delivery of glial cell line-derived neurotrophic factor by neural stem cells in a mouse model of Parkinson's disease. J. Neurosci. 21, 8108-8118.

Back, A., East, K., and Hickstein, D. (1995). Leukocyte integrin CDI lb promoter directs expression in lymphocytes and granulocytes in transgenic mice. Blood 85, 1017-1024.

Balicki, D. and Beutler, E. (2002). Gene therapy of human disease. Medicine (Baltimore) 81, 69-86.

Bell, A. C., West, A. G., and Felsenfeld, G. (1999). The protein CTCF is required for the enhancer blocking activity of vertebrate insulators. Cell 98, 387-396.

Bjorgvinsdottir, H., Ding, C., Pech, N., Gifford, M. A., Li, L. L., and Dinauer, M. C. (1997). Retroviral-mediated gene transfer of gp91phox into bone marrow cells rescues defect in host defense against Aspergillus fumigatus in murine X-linked chronic granulomatous disease. Blood 89, 41-48.

Blum, M. (1998). A null mutation in TGF-alpha leads to a reduction in midbrain dopaminergic neurons in the substantia nigra. Nat. Neurosci. 1, 374-377.

Brenner, S. and Malech, H. L. (2003). Current developments in the design of onco-retrovirus and lentivirus vector systems for hematopoietic cell gene therapy. Biochim. Biophys. Acta 1640, 1-24.

Brooks, D. J. (2003). Imaging end points for monitoring neuroprotection in Parkinson's disease. Ann. Neurol. 53 Suppl 3, S110-S118.

Burke, B., Sumner, S., Maitland, N., and Lewis, C. E. (2002). Macrophages in gene therapy: cellular delivery vehicles and in vivo targets. J. Leukoc. Biol. 72, 417428.

Cavazzana-Calvo, M., Hacein-Bey, S., de Saint, B. G., Gross, F., Yvon, E., Nusbaum, P., Selz, F., Hue, C., Certain, S., Casanova, J. L., Bousso, P., Deist, F. L., and Fischer, A. (2000). Gene therapy of human severe combined immunodeficiency (SCID)-X1 disease. Science 288, 669-672.

Choi-Lundberg, D. L., Lin, Q., Chang, Y. N., Chiang, Y. L., Hay, C. M., Mohajeri, H., Davidson, B. L., and Bohn, M. C. (1997). Dopaminergic neurons protected from degeneration by GDNF gene therapy. Science 275, 838-841.

Clarke, S. and Gordon, S. (1998). Myeloid-specific gene expression. J. Leukoc. Biol. 63, 153-168.

Cunningham, L. A. and Su, C. (2002). Astrocyte delivery of glial cell line-derived neurotrophic factor in a mouse model of Parkinson's disease. Exp. Neurol. 174, 230-242.

Deglon, N. and Aebischer, P. (2002). Lentiviruses as vectors for CNS diseases. Curr. Top. Microbiol. Immunol. 261, 191-209.

Djaldetti, R. and Melamed, E. (2001). New therapies for Parkinson's disease. J. Neurol. 248, 357-362.

Du, Y., Ma, Z., Lin, S., Dodel, R. C., Gao, F., Bales, K. R., Triarhou, L. C., Chernet, E., Perry, K. W., Nelson, D. L., Luecke, S., Phebus, L. A., Bymaster, F. P., and Paul, S. M. (2001). Minocycline prevents nigrostriatal dopaminergic neurodegeneration in the MPTP model of Parkinson's disease. Proc. Natl. Acad. Sci. U.S.A 98, 14669-14674.

Dziennis, S., Van Etten, R. A., Pahl, H. L., Morris, D. L., Rothstein, T. L., Blosch, C. M., Perlmutter, R. M., and Tenen, D. G. (1995). The CD11b promoter directs high-level expression of reporter genes in macrophages in transgenic mice. Blood 85, 319-329.

Emerich, D. F., Lindner, M. D., Winn, S. R., Chen, E. Y., Frydel, B. R., and Kordower, J. H. (1996). Implants of encapsulated human CNTF-producing fibroblasts prevent behavioral deficits and striatal degeneration in a rodent model of Huntington's disease. J. Neurosci. 16, 5168-5181.

Emerich, D. F., Winn, S. R., Hantraye, P. M., Peschanski, M., Chen, E. Y., Chu, Y., McDermott, P., Baetge, E. E., and Kordower, J. H. (1997). Protective effect of encapsulated cells producing neurotrophic factor CNTF in a monkey model of Huntington's disease. Nature 386, 395-399.

Fedorov, L. M., Tyrsin, O. Y., Sakk, O., Ganscher, A., and Rapp, U. R. (2001). Generation dependent reduction of tTA expression in double transgenic NZL-2/tTA(CMV) mice. Genesis. 31, 78-84.

Galimi, F. and Verma, I. M. (2002). Opportunities for the use of lentiviral vectors in human gene therapy. Curr. Top. Microbiol. Immunol. 261, 245-254.

Gill, S. S., Patel, N. K., Hotton, G. R., O'Sullivan, K., McCarter, R., Bunnage, M., Brooks, D. J., Svendsen, C. N., and Heywood, P. (2003). Direct brain infusion of glial cell line-derived neurotrophic factor in Parkinson disease. Nat. Med. 9, 589-595.

Goetz, C. G., Olanow, C. W., Koller, W. C., Penn, R. D., Cahill, D., Morantz, R., Stebbins, G., Tanner, C. M., Klawans, H. L., and Shannon, K. M. (1989). Multicenter study of autologous adrenal medullary transplantation to the corpus striatum in patients with advanced Parkinson's disease. N. Engl. J. Med. 320, 337-341.

Gouhier, C., Chalon, S., Aubert-Pouessel, A., Venier-Julienne, M. C., Jollivet, C., Benoit, J. P., and Guilloteau, D. (2002). Protection of dopaminergic nigrostriatal afferents by GDNF delivered by microspheres in a rodent model of Parkinson's disease. Synapse 44, 124-131.

Grondin, R. and Gash, D. M. (1998). Glial cell line-derived neurotrophic factor (GDNF): a drug candidate for the treatment of Parkinson's disease. J. Neurol. 245, 35-42.

Hacein-Bey-Abina, S., de Saint, B. G., and Cavazzana-Calvo, M. (2003a). Gene therapy of X-linked severe combined immunodeficiency. Methods Mol. Biol. 215, 247-259.

Hacein-Bey-Abina, S., Le Deist, F., Carlier, F., Bouneaud, C., Hue, C., De Villartay, J. P., Thrasher, A. J., Wulffraat, N., Sorensen, R., Dupuis-Girod, S., Fischer, A., Davies, E. G., Kuis, W., Leiva, L., and Cavazzana-Calvo, M. (2002). Sustained correction of X-linked severe combined immunodeficiency by ex vivo gene therapy. N. Engl. J. Med. 346, 1185-1193.

Hacein-Bey-Abina, S., von Kalle, C., Schmidt, M., Le Deist, F., Wulffraat, N., McIntyre, E., Radford, I., Villeval, J. L., Fraser, C. C., Cavazzana-Calvo, M., and Fischer, A. (2003b). A serious adverse event after successful gene therapy for X-linked severe combined immunodeficiency. N. Engl. J. Med. 348, 255-256.

Hahn, C. N., del Pilar, M. M., Zhou, X. Y., Mann, L. W., and d'Azzo, A. (1998). Correction of murine galactosialidosis by bone marrow-derived macrophages overexpressing human protective protein/cathepsin A under control of the colony-stimulating factor-1 receptor promoter. Proc. Natl. Acad. Sci. U.S.A 95, 14880-14885.

Ho, A. and Blum, M. (1998). Induction of interleukin-1 associated with compensatory dopaminergic sprouting in the denervated striatum of young mice: model of aging and neurodegenerative disease. J. Neurosci. 18, 5614-5629.

Horwitz, E. M., Gordon, P. L., Koo, W. K., Marx, J. C., Neel, M. D., McNall, R. Y., Muul, L., and Hofmann, T. (2002). Isolated allogeneic bone marrow-derived mesenchymal cells engraft and stimulate growth in children with osteogenesis imperfecta: Implications for cell therapy of bone. Proc. Natl. Acad. Sci. U.S.A 99, 8932-8937.

Hubner, K., Fuhrmann, G., Christenson, L. K., Kehler, J., Reinbold, R., De La, F. R., Wood, J., Strauss, J. F., III, Boiani, M., and Scholer, H. R. (2003). Derivation of oocytes from mouse embryonic stem cells. Science 300, 1251-1256.

Imren, S., Payen, E., Westerman, K. A., Pawliuk, R., Fabry, M. E., Eaves, C. J., Cavilla, B., Wadsworth, L. D., Beuzard, Y., Bouhassira, E. E., Russell, R., London, I. M., Nagel, R. L., Leboulch, P., and Humphries, R. K. (2002). Permanent and panerythroid correction of murine beta thalassemia by multiple lentiviral integration in hematopoietic stem cells. Proc. Natl. Acad. Sci. U. S. A 99, 14380-14385.

Jiang, Y., Jahagirdar, B. N., Reinhardt, R. L., Schwartz, R. E., Keene, C. D., Ortiz-Gonzalez, X. R., Reyes, M., Lenvik, T., Lund, T., Blackstad, M., Du, J., Aldrich, S., Lisberg, A., Low, W. C., Largaespada, D. A., and Verfaillie, C. M. (2002). Pluripotency of mesenchymal stem cells derived from adult marrow. Nature 418, 41-49.

Kennedy, D. W. and Abkowitz, J. L. (1997). Kinetics of central nervous system microglial and macrophage engraftment: analysis using a transgenic bone marrow transplantation model. Blood 90, 986-993.

Kordower, J. H. (2003). In vivo gene delivery of glial cell line—derived neurotrophic factor for Parkinson's disease. Ann. Neurol. 53 Suppl 3, S120-S132.

Kordower, J. H. and Aebischer, P. (2001). Gene therapy to the rescue in Parkinson's disease. Response from Kordower and Aebischer. Trends Pharmacol. Sci. 22, 105-106.

Kordower, J. H., Emborg, M. E., Bloch, J., Ma, S. Y., Chu, Y., Leventhal, L., McBride, J., Chen, E. Y., Palfi, S., Roitberg, B. Z., Brown, W. D., Holden, J. E., Pyzalski, R., Taylor, M. D., Carvey, P., Ling, Z., Trono, D., Hantraye, P., Deglon, N., and Aebischer, P. (2000). Neurodegeneration prevented by lentiviral vector delivery of GDNF in primate models of Parkinson's disease. Science 290, 767-773.

Kozorovitskiy, Y. and Gould, E. (2003). Stem cell fusion in the brain. Nat. Cell Biol. 5, 952-954.

Leimig, T., Mann, L., Martin, M. P., Bonten, E., Persons, D., Knowles, J., Allay, J. A., Cunningham, J., Nienhuis, A. W., Smeyne, R., and d'Azzo, A. (2002). Functional amelioration of murine galactosialidosis by genetically modified bone marrow hematopoietic progenitor cells. Blood 99, 3169-3178.

Li, X., Eastman, E. M., Schwartz, R. J., and Draghia-Akli, R. (1999). Synthetic muscle promoters: activities exceeding naturally occurring regulatory sequences. Nat. Biotechnol. 17, 241-245.

McBride, J. L., During, M. J., Wuu, J., Chen, E. Y., Leurgans, S. E., and Kordower, J. H. (2003). Structural and functional neuroprotection in a rat model of Huntington's disease by viral gene transfer of GDNF. Exp. Neurol. 181, 213-223.

Metcalfe, B. L., Sellers, K. W., Jeng, M. J., Huentelman, M. J., Katovich, M. J., and Raizada, M. K. (2001). Gene therapy for cardiovascular disorders: is there a future? Ann. N. Y. Acad. Sci. 953, 3142.

Miyoshi, H., Blomer, U., Takahashi, M., Gage, F. H., and Verma, I. M. (1998). Development of a self-inactivating lentivirus vector. J. Virol. 72, 8150-8157.

Morgan, W. W. and Nelson, J. F. (2001). Chronic administration of pharrnacological levels of melatonin does not ameliorate the MPTP-induced degeneration of the nigrostriatal pathway. Brain Res. 921, 115-121.

Morgan, W. W., Rudeen, P. K., and Pfeil, K. A. (1975). Effect of immobilization stress on serotonin content and turnover in regions of the rat brain. Life Sci. 17, 143-150.

Okragly, A. J. and Haak-Frendscho, M. (1997). An acid-treatment method for the enhanced detection of GDNF in biological samples. Exp. Neurol. 145, 592-596.

Pawliuk, R., Westerman, K. A., Fabry, M. E., Payen, E., Tighe, R., Bouhassira, E. E., Acharya, S. A., Ellis, J., London, I. M., Eaves, C. J., Humphries, R. K., Beuzard, Y., Nagel, R. L., and Leboulch, P. (2001). Correction of sickle cell disease in transgenic mouse models by gene therapy. Science 294, 2368-2371.

Persons, D. A. and Nienhuis, A. W. (2000). Gene therapy for the hemoglobin disorders: past, present, and future. Proc. Natl. Acad. Sci. U.S.A 97, 5022-5024.

Pfeifer, A., Ikawa, M., Dayn, Y., and Verma, I. M. (2002). Transgenesis by lentiviral vectors: lack of gene silencing in mammalian embryonic stem cells and preimplantation embryos. Proc. Natl. Acad. Sci. U.S.A 99, 2140-2145.

Phillips, A. J. (2001). The challenge of gene therapy and DNA delivery. J. Pharm. Pharmacol. 53, 1169-1174.

Priller, J., Flugel, A., Wehner, T., Boentert, M., Haas, C. A., Prinz, M., Fernandez-Klett, F., Prass, K., Bechmann, I., de Boer, B. A., Frotscher, M., Kreutzberg, G. W., Persons, D. A., and Dimagl, U. (2001). Targeting gene-modified hematopoietic cells to the central nervous system: use of green fluorescent protein uncovers microglial engraftment. Nat. Med. 7, 1356-1361.

Rascol, O., Payoux, P., Ory, F., Ferreira, J. J., Brefel-Courbon, C., and Montastruc, J. L. (2003). Limitations of current Parkinson's disease therapy. Ann. Neurol. 53 Suppl 3, S3-12.

Recillas-Targa, F., Bell, A. C., and Felsenfeld, G. (1999). Positional enhancer-blocking activity of the chicken beta-globin insulator in transiently transfected cells. Proc. Natl. Acad. Sci. U.S.A 96, 14354-14359.

Rhoades, K. L., Hetherington, C. J., Harakawa, N., Yergeau, D. A., Zhou, L., Liu, L. Q., Little, M. T., Tenen, D. G., and Zhang, D. E. (2000). Analysis of the role of AML1-ETO in leukemogenesis, using an inducible transgenic mouse model. Blood 96, 2108-2115.

Roesler, J., Brenner, S., Bukovsky, A. A., Whiting-Theobald, N., Dull, T., Kelly, M., Civin, C. I., and Malech, H. L. (2002). Third-generation, self-inactivating gp91(phox) lentivector corrects the oxidase defect in NOD/SCID mouse-repopulating peripheral blood-mobilized CD34+ cells from patients with X-linked chronic granulomatous disease. Blood 100, 4381-4390.

Sclimenti, C. R., Baba, E. J., and Calos, M. P. (2000). An extrachromosomal tetracycline-regulatable system for mammalian cells. Nucleic Acids Res. 28, E80.

Shariatmadari, R., Sipila, P. P., Huhtaniemi, I. T., and Poutanen, M. (2001). Improved technique for detection of enhanced green fluorescent protein in transgenic mice. Biotechniques 30, 1282-1285.

Shastry, B. S. (2001). Parkinson disease: etiology, pathogenesis and future of gene therapy. Neurosci. Res. 41, 5-12.

Steece-Collier, K., Maries, E., and Kordower, J. H. (2002). Etiology of Parkinson's disease: Genetics and environment revisited. Proc. Natl. Acad. Sci. U.S.A 99, 13972-13974.

Tahara-Hanaoka, S., Sudo, K., Ema, H., Miyoshi, H., and Nakauchi, H. (2002). Lentiviral vector-mediated transduction of murine CD34(-) hematopoietic stem cells. Exp. Hematol. 30, 11-17.

Tatton, W. G., Chalmers-Redman, R., Brown, D., and Tatton, N. (2003). Apoptosis in Parkinson's disease: signals for neuronal degradation. Ann. Neurol. 53 Suppl 3, S61-S70.

Tenen, D. G., Hromas, R., Licht, J. D., and Zhang, D. E. (1997). Transcription factors, normal myeloid development, and leukemia. Blood 90, 489-519.

Tolba, K. A., Bowers, W. J., Hilchey, S. P., Halterman, M. W., Howard, D. F., Giuliano, R. E., Federoff, H. J., and Rosenblatt, J. D. (2001). Development of herpes simplex virus-1 amplicon-based immunotherapy for chronic lymphocytic leukemia. Blood 98, 287-295.

Tseng, J. L., Baetge, E. E., Zurn, A. D., and Aebischer, P. (1997). GDNF reduces drug-induced rotational behavior after medial forebrain bundle transection by a mechanism not involving striatal dopamine. J. Neurosci. 17, 325-333.

Ugarte, S. D., Lin, E., Klann, E., Zigmond, M. J., and Perez, R. G. (2003). Effects of GDNF on 6-OHDA-induced death in a dopaminergic cell line: modulation by inhibitors of PI3 kinase and MEK. J. Neurosci. Res. 73, 105-112.

Vigna, E., Cavalieri, S., Ailles, L., Geuna, M., Loew, R., Bujard, H., and Naldini, L. (2002b). Robust and efficient regulation of transgene expression in vivo by improved tetracycline-dependent lentiviral vectors. Mol. Ther. 5, 252-261.

Vigna, E., Cavalieri, S., Ailles, L., Geuna, M., Loew, R., Bujard, H., and Naldini, L. (2002a). Robust and efficient regulation of transgene expression in vivo by improved tetracycline-dependent lentiviral vectors. Mol. Ther. 5, 252-261.

Wang, L., Muramatsu, S., Lu, Y., Ikeguchi, K., Fujimoto, K., Okada, T., Mizukami, H., Hanazono, Y., Kume, A., Urano, F., Ichinose, H., Nagatsu, T., Nakano, I., and Ozawa, K. (2002). Delayed delivery of AAV-GDNF prevents nigral neurodegeneration and promotes functional recovery in a rat model of Parkinson's disease. Gene Ther. 9, 381-389.

Winkler, J., Thal, L. J., Gage, F. H., and Fisher, L. J. (1998). Cholinergic strategies for Alzheimer's disease. J. Mol. Med. 76, 555-567.

Wipke, B. T., Wang, Z., Kim, J., McCarthy, T. J., and Allen, P. M. (2002). Dynamic visualization of a joint-specific autoimmune response through positron emission tomography. Nat. Immunol. 3, 366-372.

Wu, X., Li, Y., Crise, B., and Burgess, S. M. (2003). Transcription start regions in the human genome are favored targets for MLV integration. Science 300, 1749-1751.

Wu, Y. P., McMahon, E., Kraine, M. R., Tisch, R., Meyers, A., Frelinger, J., Matsushima, G. K., and Suzuki, K. (2000). Distribution and characterization of GFP(+) donor hematogenous cells in Twitcher mice after bone marrow transplantation. Am. J. Pathol. 156, 1849-1854.

Example 2

Parkinson's Disease

Human GDNF cDNA is inserted into Lenti-SMP-GFP to replace the EGFP gene. The GDNF is either tagged byflag sequence (DYKDDDDK, SEQ ID NO:1) at the carboxyl terminus or not. The resulting constructs, Lenti-SMP-GDNF and Lenti-SMP-GDNFflag and the parent vector Lenti-SMP-GFP are each co-transfected respectively together with the three packaging plasmids into 293T cells to produce lentiviral particles, which will then be concentrated by ultra-centrifugation and used to transduce mouse bone marrow stem cells ex vivo for 6 hours. The transduced bone marrow cells will be transplanted into lethally irradiated mice. Five weeks after BMT, the recipient mice will be subject to either acute or chronic MPTP treatment. Rotorod testing will be performed weekly. At days 1, 14 and 56 after MPTP administration, the mice will be killed either by decapitation or intracardiac perfusion for tissue collection. Dopamine uptake and expression of tyrosine hydroxylase (TH) will be measured. Dopaminergic neurons will be counted, and apoptosis in cells of the SN examined by TUNEL staining and immunohistochemical analysis of active caspase-3.

Mice C57BL/6 mice are purchased from The Jackson Laboratory. BMT recipient mice will be given drinking water with 100 mg/liter neomycin and 10 mg/liter polymyxin B for 3 days before and 14 days after transplantation.

Lentiviral vector production VSV-G-pseudotyped lentiviral particles are generated by transient cotransfection of plasmid DNA of the transfer vectors (Lenti-SMP-GDNF, Lenti-SMP-GDNFflag and the parent vector Lenti-SMP-GFP) with the three packaging plasmids (pMDLg/pRRE, the gag-pol plasmid; pRSV-Rev, a Rev expressing plasmid; and pMD.G, a VSV-G envelope expressing plasmid) into 293T cells as described. Lentivector supernatants are filtered, concentrated by twice ultracentrifugation (55,000 g for 3 hours), and stored at −70° C.[27,28]. The viral titers are estimated by transduction of 293T cells with the CMV-EGFP lentivector processed simultaneously.

Bone marrow cell culture, lentiviral infection, and transplantation. Isolation, transduction, and transplantation of murine bone marrow (BM) cells are done as described[27]. Briefly, BM is obtained from femurs and tibias of 7-week-old female mice 4 days after i.v. injection of 5-FU at a dose of 100 mg/kg body weight. Bone marrow cells are treated with Lympholyte-M for enrichment of HSCs, and stimulated overnight in StemPro medium along with 6 ng/ml of IL-3, 10 ng/ml of IL-6, 10 ng/ml of murine IL-1α and 100 ng/ml of Stem Cell factor. The next day, cells are pelleted and resuspended in 0.85 ml of the aforementioned medium containing the same growth factor combination with concentrated, vesicular stomatitis virus glycoprotein-G-pseudotyped lentivectors at a final virus concentration of $2\text{-}8\times10^9$ infectious units/ml. Infection is performed for 6 h on fibronectin-coated Petri dishes in the presence of 8 μg/ml protamine sulfate. After infection, $2\times10^6$ cells are transplanted, without selection, by i.v. injection into each syngeneic recipient (5-week-old male mice) given 950 cGy of total body irradiation.

MPTP treatment Although acute MPTP animal models are available, progressive destruction of dopaminergic nigrostriatal neurons occurs in mice treated daily with low doses of MPTP for a few weeks and mirrors closely the pattern of evolution assumed to be that of Parkinson's disease. Such a chronic model is being developed. Both acute and chronic models are used in this invention. Five weeks post-transplantation, a group of eight randomly selected recipient mice receive four doses of 13 mg/kg body weight of MPTP-HCl injected subcutaneously at 2 hr intervals. Another group receives this treatment followed by a daily injection with 13 mg/kg MPTP-HCl for 20 days. Controls receive saline only.

Coordination Testing on a Rota-Rod Mice will be trained twice on 2 consecutive days for a 5-min period at low speed (3 rpm) to become accustomed to the accelerating rotarod (Rotamex-4/8, Columbus Instruments). On the third and fourth days, they will be placed on the rotarod at accelerating speeds from 3 to 50 rpm (increments of 5 rpm/30 sec) and will be tested four times with a 5-min break between tests. The mice will be kept on the apparatus for a maximum of 280 sec. The time each mouse remained on the rod will be registered automatically. For each mouse, a single measurement will be calculated to represent the average performance of these four attempts and be presented as latency to fall. All testing will be performed between 2 and 5 p.m.[30].

Counting of dopaminergic neurons Animals are anesthetized with Avertin and sacrificed by transcardic perfusion first with phosphate buffered saline(PBS, PH 7.4) followed by 4% phosphate-buffered paraformaldehyde(PFA, pH 7.4) for 10 minutes. The brains are removed and post-fixed in 4% PFA at 4° C. overnight and then cryoprotected in 30% sucrose. The tissues are frozen and sectioned at 50 μm on a cryostat for unbiased counting of dopaminergic neurons in SNpc with Stero-Investigator.

For immunohistochemistry, the sections are rinsed and floated in PBS, then blocked with 0.3% Triton X-100 and 3% normal goat serum in PBS for 30 min followed by incubation with rabbit polyclonal anti-TH antibody(1:500; Pel-Freeze Biologicals) overnight. Then sections are washed for 3×10 min with PBS and incubated in biotinylated goat anti-rabbit IgG for 2 hrs at room temperature. Then sections are washed for 3×10 min with PBS and incubated in peroxidase conjugated-Extravindin (1;1000, Sigma) for 1 hr at room temperature followed by a 5-min-incubation with 0.05% 3,3'-diaminobenzidine tetrachloride (Sigma) and 0.03% $H_2O_2$ in PBS. After processing, sections are washed in distilled water, dehydrated through graded alcohols, cleared in xylene, and coverslipped in mounting medium (Electron Microscopy Sciences). The number of TH-IR neurons is determined by counting every other section from sections covered the whole length of SNpc in midbrain at a magnification of 100×.

Microglial GDNF expression in SN and striatum Combined fluorescence immunocytochemistry (double immunolabeling) for GDNF or flag and IBA1 (macrophage/microglial marker) is used. Sections are incubated in blocking buffer 0.3% Triton X-100 in PBS and 3% goat serum in PBS) for 30 min, followed by an overnight incubation of primary antibody (sheep-anti-GDNF, Biocompare and IBA1, Wake Pure Chemicals) in blocking buffer at 4° C. GDNF is visualized by incubation with donkey anti-sheep IgG directly conjugated to fluorescein (1:200), whereas IBA1 immunoreactivity is reacted to Texas Red-goat anti rabbit. After processing, sections are mounted on coated slides, dried, and coverslipped in Permafluor mounting medium [52]. GDNF expression is also measured by ELISA (Promega, cat#G7620) and Western Blot with anti-flag and/or anti-GDNF antibody.

[$^3$H]Dopamine uptake Animals are decapitated, and the brains quickly removed into cold sterile saline. Dorsal and ventral striatum are separated carefully using the anterior commissure as an anatomical landmark. Then tissues are homogenized in 500 μl of ice-cold prelysis buffer (10 mM Tris, pH 7.5, and 0.32M sucrose) using a Teflon pestle-glass mortar pair. Homogenized tissue is removed and centrifuged for 10 min at 1000 g at 4° C. to remove nuclei. The supernatant containing the synaptosomes is collected, and aliquots are removed for the determination of protein concentration and dopamine uptake (total high-affinity and mazindol-non-inhibitable). Fifty microliters of supernatant are diluted in 450 μl of Krebs-Ringer phosphate buffer (0.1M) with added EDTA (1.3 mM), glucose (5.6 mM), and ascorbic acid (0.2 mg/ml) and incubated at 37° C. in the presence or absence of 10 μM mazindol (Research Biochemicals), a high-affinity dopamine uptake inhibitor. [³H]Dopamine (specific activity, 20-40 Ci/mmol; Amersham, Arlington Heights, Ill.) is added to a final concentration of 0.025 µM, and incubation is at 37° C. for 6 min. Synaptosomes are collected on presoaked nitrocellulose filters by filtration, and nonspecific radioactivity is washed with Krebs-Ringer phosphate buffer followed by filtration. The filters are transferred into scintillation vials of Hionic-fluor and measured by liquid scintillation spectrometry. Specific high-affinity neuronal dopamine uptake is expressed as femtomoles of dopamine uptake per microgram of protein minus the femtomoles of mazindol uptake. Values are presented as the change in dopamine uptake[52].

Detection of apoptotic neurodegeneration Cryostat sections are prepared at 20 µm thickness and sections mounted on slides. TUNEL reaction is carried out using the ApopTag-Red (Intergen, Purchase, N.Y.) per manufacturer directions.

Western blot analysis of TH expression Striatum and ventral midbrain are cut from blocks of brain tissue frozen at −80° C. carefully, then individually homogenized in RIPA buffer (0.1 M PBS, 1% non-ionic detergent (Igepal), 0.5% sodium deoxycholate, 0.1% sodium dodecyl sulfate, 1 mM dithiothreitol) containing the protease inhibitors phenyl-methlsulfonyl fluoride (0.1 mM), leupeptin (2 m g/ ml), and aprotinin (4.6 m g/ ml). After incubation in buffer for 30 min at 4° C., samples are centrifuged at 10,000 g for 10 min at 4° C. Supernatants are collected and protein concentration determined. A 30-mg sample of total protein is denatured for 5 min in sample buffer (0.125 M Tris-HCl, pH 6.8, 4% sodium dodecyl sulfate, 20% glycerol, 10% β-mercaptoethanol and 0.006% bromophenol blue), electrophoresed onto a 7% SDS-PAGE, and transferred to a Hybond ECL nitrocellulose membrane. To verify the quality and equal concentration of the proteins in the filter, staining with Ponceau S is carried out. The blot is washed in Tris-buffered saline containing 0.05% Tween 20, saturated with 5% bovine serum albumin and 5% skim milk for 1 h and incubated overnight at 4° C. with TH-mouse monoclonal antibody (Roche Diagnostics, Mannhein, Germany), diluted 1:2000. After washing, the blot is incubated with horse anti-mouse IgG linked with peroxidase diluted 1:2000 for 1 h. The reaction is developed using an ECL method[50,51].

Other measurements Tyrosine hydroxylase assay and catecholamine (including dopamine) analysis is carried out following described protocols[54]. Real-time quantitative PCR is used to determine analysis proviral copy number in recipient blood cells[36]. Peripheral blood cells (hematocrit, white blood cell, differential, and reticulocyte counts) are counted to examine whether the hematopoiesis is altered by the proposed manipulation[55]. Secondary BMT is performed to confirm that integration of functional lentivector provirus has occurred in reconstituting stem cells. BM from primary recipients is harvested 4 to 8 months post-transplantation and used for secondary transplants[55].

Safety testing Genomic DNA from peripheral blood cells is screened for the presence of replication competent retrovirus by using a PCR assay to detect sequence encoding the envelope[25,36,56].

Statistical Analysis ANOVA is used to examine any statistical difference among groups, followed by Newman-Keuls comparison or Bonferroni comparison analysis.

REFERENCE FOR EXAMPLE 2

(1) Kordower J H, Aebischer P. Gene therapy to the rescue in Parkinson's disease. Response from Kordower and Aebischer. Trends Pharmacol Sci. 2001; 22:105-106.

(2) Djaldetti R, Melamed E. New therapies for Parkinson's disease. J Neurol. 2001; 248:357-362.

(3) Goetz C G, Olanow C W, Koller W C et al. Multicenter study of autologous adrenal medullary transplantation to the corpus striatum in patients with advanced Parkinson's disease. N Engl J Med. 1989; 320:337-341.

(4) Du Y, Ma Z, Lin S et al. Minocycline prevents nigrostriatal dopaminergic neurodegeneration in the MPTP model of Parkinson's disease. Proc Natl Acad Sci USA. 2001; 98:14669-14674.

(5) Shastry B S. Parkinson disease: etiology, pathogenesis and future of gene therapy. Neurosci Res. 2001; 41:5-12.

(6) Deglon N, Aebischer P. Lentiviruses as vectors for CNS diseases. Curr Top Microbiol Immunol. 2002; 261:191-209.

(7) Gill S S, Patel N K, Hotton G R et al. Direct brain infusion of glial cell line-derived neurotrophic factor in Parkinson disease. Nat Med. 2003; 9:589-595.

(8) Kordower J H, Emborg M E, Bloch J et al. Neurodegeneration prevented by lentiviral vector delivery of GDNF in primate models of Parkinson's disease. Science. 2000; 290:767-773.

(9) Kordower J H. In vivo gene delivery of glial cell line—derived neurotrophic factor for Parkinson's disease. Ann Neurol. 2003; 53 Suppl 3:S120-S132.

(10) Emerich D F, Lindner M D, Winn S R et al. Implants of encapsulated human CNTF-producing fibroblasts prevent behavioral deficits and striatal degeneration in a rodent model of Huntington's disease. J Neurosci. 1996; 16:5168-5181.

(11) Emerich D F, Winn S R, Hantraye P M et al. Protective effect of encapsulated cells producing neurotrophic factor CNTF in a monkey model of Huntington's disease. Nature. 1997; 386:395-399.

(12) McBride J L, During M J, Wuu J et al. Structural and functional neuroprotection in a rat model of Huntington's disease by viral gene transfer of GDNF. Exp Neurol. 2003; 181:213-223.

(13) Winkler J, Thal L J, Gage F H, Fisher L J. Cholinergic strategies for Alzheimer's disease. J Mol Med. 1998; 76:555-567.

(14) Choi-Lundberg D L, Lin Q, Chang Y N et al. Dopaminergic neurons protected from degeneration by GDNF gene therapy. Science. 1997; 275:838-841.

(15) Grondin R, Gash D M. Glial cell line-derived neurotrophic factor (GDNF): a drug candidate for the treatment of Parkinson's disease. J Neurol. 1998; 245:35-42.

(16) Akerud P, Canals J M, Snyder E Y, Arenas E. Neuroprotection through delivery of glial cell line-derived neurotrophic factor by neural stem cells in a mouse model of Parkinson's disease. J Neurosci. 2001; 21:8108-8118.

(17) Cunningham L A, Su C. Astrocyte delivery of glial cell line-derived neurotrophic factor in a mouse model of Parkinson's disease. Exp Neurol. 2002; 174:230-242.

(18) Cavazzana-Calvo M, Hacein-Bey S, de Saint B G et al. Gene therapy of human severe combined immunodeficiency (SCID)-X1 disease. Science. 2000; 288:669-672.

(19) Aiuti A, Slavin S, Aker M et al. Correction of ADA-SCID by stem cell gene therapy combined with nonmyeloablative conditioning. Science. 2002; 296:2410-2413.

(20) Hacein-Bey-Abina S, Le Deist F, Carlier F et al. Sustained correction of X-linked severe combined immunodeficiency by ex vivo gene therapy. N Engl J Med. 2002; 346:1185-1193.

(21) Hacein-Bey-Abina S, von Kalle C, Schmidt M et al. A serious adverse event after successful gene therapy for X-linked severe combined immunodeficiency. N Engl J Med. 2003; 348:255-256.

(22) Hacein-Bey-Abina S, de Saint B G, Cavazzana-Calvo M. Gene therapy of X-linked severe combined immunodeficiency. Methods Mol Biol. 2003; 215:247-259.

(23) Wu X, Li Y, Crise B, Burgess S M. Transcription start regions in the human genome are favored targets for MLV integration. Science. 2003; 300:1749-1751.

(24) Balicki D, Beutler E. Gene therapy of human disease. Medicine (Baltimore). 2002; 81:69-86.

(25) Brenner S, Malech H L. Current developments in the design of onco-retrovirus and lentivirus vector systems for hematopoietic cell gene therapy. Biochim Biophys Acta. 2003; 1640:1-24.

(26) Pfeifer A, Ikawa M, Dayn Y, Verma I M. Transgenesis by lentiviral vectors: lack of gene silencing in mammalian embryonic stem cells and preimplantation embryos. Proc Natl Acad Sci U S A. 2002; 99:2140-2145.

(27) Pawliuk R, Westerman K A, Fabry M E et al. Correction of sickle cell disease in transgenic mouse models by gene therapy. Science. 2001; 294:2368-2371.

(28) Imren S, Payen E, Westerman K A et al. Permanent and panerythroid correction of murine beta thalassemia by multiple lentiviral integration in hematopoietic stem cells. Proc Natl Acad Sci U S A. 2002; 99:14380-14385.

(29) Clarke S, Gordon S. Myeloid-specific gene expression. J Leukoc Biol. 1998; 63:153-168.

(30) Hahn C N, del Pilar M M, Zhou X Y, Mann L W, d'Azzo A. Correction of murine galactosialidosis by bone marrow-derived macrophages overexpressing human protective protein/cathepsin A under control of the colony-stimulating factor-1 receptor promoter. Proc Natl Acad Sci USA. 1998; 95:14880-14885.

(31) Burke B, Sumner S, Maitland N, Lewis C E. Macrophages in gene therapy: cellular delivery vehicles and in vivo targets. J Leukoc Biol. 2002; 72:417-428.

(32) Kennedy D W, Abkowitz J L. Kinetics of central nervous system microglial and macrophage engraftment: analysis using a transgenic bone marrow transplantation model. Blood. 1997; 90:986-993.

(33) Wu Y P, McMahon E, Kraine M R et al. Distribution and characterization of GFP(+) donor hematogenous cells in Twitcher mice after bone marrow transplantation. Am J Pathol. 2000; 156:1849-1854.

(34) Priller J, Flugel A, Wehner T et al. Targeting gene-modified hematopoietic cells to the central nervous system: use of green fluorescent protein uncovers microglial engraftment. Nat Med. 2001; 7:1356-1361.

(35) Leimig T, Mann L, Martin M P et al. Functional amelioration of murine galactosialidosis by genetically modified bone marrow hematopoietic progenitor cells. Blood. 2002; 99:3169-3178.

(36) Roesler J, Brenner S, Bukovsky A A et al. Third-generation, self-inactivating gp91(phox) lentivector corrects the oxidase defect in NOD/SCID mouse-repopulating peripheral blood-mobilized CD34+ cells from patients with X-linked chronic granulomatous disease. Blood. 2002; 100:4381-4390.

(37) Sclimenti C R, Baba E J, Calos M P. An extrachromosomal tetracycline-regulatable system for mammalian cells. Nucleic Acids Res. 2000; 28:E80.

(38) Vigna E, Cavalieri S, Ailles L et al. Robust and efficient regulation of transgene expression in vivo by improved tetracycline-dependent lentiviral vectors. Mol Ther. 2002; 5:252-261.

(39) Li X, Eastman E M, Schwartz R J, Draghia-Akli R. Synthetic muscle promoters: activities exceeding naturally occurring regulatory sequences. Nat Biotechnol. 1999; 17:241-245.

(40) Draghia-Akli R, Ellis K M, Hill L A, Malone P B, Fiorotto M L. High-efficiency growth hormone-releasing hormone plasmid vector administration into skeletal muscle mediated by electroporation in pigs. FASEB J. 2003; 17:526-528.

(41) Li S L, Valente A J, Zhao S J, Clark R A. PU.1 is essential for p47(phox) promoter activity in myeloid cells. J Biol Chem. 1997; 272:17802-17809.

(42) Li S L, Schlegel W, Valente A J, Clark R A. Critical flanking sequences of PU.1 binding sites in myeloid-specific promoters. J Biol Chem. 1999; 274:32453-32460.

(43) Li S L, Valente A J, Wang L, Gamez M J, Clark R A. Transcriptional regulation of the p67phox gene: role of AP-1 in concert with myeloid-specific transcription factors. J Biol Chem. 2001; 276:39368-39378.

(44) Li S L, Valente A J, Qiang M et al. Multiple PU.1 sites cooperate in the regulation of p40(phox) transcription during granulocytic differentiation of myeloid cells. Blood. 2002; 99:4578-4587.

(45) Ward A C, Loeb D M, Soede-Bobok A A, Touw I P, Friedman A D. Regulation of granulopoiesis by transcription factors and cytokine signals. Leukemia. 2000; 14:973-990.

(46) Shivdasani R A, Orkin S H. The transcriptional control of hematopoiesis. Blood. 1996; 87:4025-4039.

(47) Tenen D G, Hromas R, Licht J D, Zhang D E. Transcription factors, normal myeloid development, and leukemia. Blood. 1997; 90:489-519.

(48) Roberts W M, Shapiro L H, Ashmun R A, Look A T. Transcription of the human colony-stimulating factor-1 receptor gene is regulated by separate tissue-specific promoters. Blood. 1992; 79:586-593.

(49) Dziennis S, Van Etten R A, Pahl H L et al. The CD11b promoter directs high-level expression of reporter genes in macrophages in transgenic mice. Blood. 1995; 85:319-329.

(50) Bezard E, Dovero S, Bioulac B, Gross C E. Kinetics of nigral degeneration in a chronic model of MPTP-treated mice. Neurosci Lett. 1997; 234:47-50.

(51) Antolin I, Mayo J C, Sainz R M et al. Protective effect of melatonin in a chronic experimental model of Parkinson's disease. Brain Res. 2002; 943:163-173.

(52) Ho A, Blum M. Induction of interleukin-1 associated with compensatory dopaminergic sprouting in the denervated striatum of young mice: model of aging and neurodegenerative disease. J Neurosci. 1998; 18:5614-5629.

(53) Tatton W G, Chalmers-Redman R, Brown D, Tatton N. Apoptosis in Parkinson's disease: signals for neuronal degradation. Ann Neurol. 2003; 53 Suppl 3:S61-S70.

(54) Morgan W W, Nelson J F. Chronic administration of pharmacological levels of melatonin does not ameliorate the MPTP-induced degeneration of the nigrostriatal pathway. Brain Res. 2001; 921:115-121.

(55) Bjorgvinsdottir H, Ding C, Pech N et al. Retroviral-mediated gene transfer of gp91phox into bone marrow cells rescues defect in host defense against *Aspergillus fumigatus* in murine X-linked chronic granulomatous disease. Blood. 1997; 89:41-48.

(56) Galimi F, Verma I M. Opportunities for the use of lentiviral vectors in human gene therapy. Curr Top Microbiol Immunol. 2002; 261:245-254.

(57) Gouhier C, Chalon S, Aubert-Pouessel A et al. Protection of dopaminergic nigrostriatal afferents by GDNF delivered by microspheres in a rodent model of Parkinson's disease. Synapse. 2002; 44:124-131.
(58) Ugarte SD, Lin E, Kann E, Zigmond M J, Perez R G. Effects of GDNF on 6-OHDA-induced death in a dopaminergic cell line: modulation by inhibitors of P13 kinase and MEK. J Neurosci Res. 2003; 73:105-112.
(59) Wang L, Muramatsu S, Lu Y et al. Delayed delivery of AAV-GDNF prevents nigral neurodegeneration and promotes functional recovery in a rat model of Parkinson's disease. Gene Ther. 2002; 9:381-389.
(60) Shariatmadari R, Sipila P P, Huhtaniemi I T, Poutanen M. Improved technique for detection of enhanced green fluorescent protein in transgenic mice. Biotechniques. 2001; 30:1282-1285.
(61) Brooks D J. Imaging end points for monitoring neuroprotection in Parkinson's disease. Ann Neurol. 2003; 53 Suppl 3:S110-S118.
(62) Wipke B T, Wang Z, Kim J, McCarthy T J, Allen P M. Dynamic visualization of a joint-specific autoimmune response through positron emission tomography. Nat Immunol. 2002; 3:366-372.

Example 3

Atheroscleorsis

Atherosclerosis, which leads to myocardial infarction (MI), stroke, and peripheral occlusive vascular disease, is the leading cause of mortality in this country. Atherosclerosis is considered to be a disorder of lipid metabolism, as well as a chronic inflammatory disease. Macrophages, critical in all phases of atherosclerosis, from fatty streak development to plaque rupture and MI, are a prime target for therapeutic intervention in this disease.

Liver X receptors (LXRα and LXRβ) reciprocally regulate lipid metabolism and inflammation. Lack of LXR expression in macrophages markedly increases susceptibility to atherosclerosis, whereas synthetic LXR agonists inhibit atherosclerosis development in both apoE−/− and LDLR−/− mouse models. However, LXRs also cause hyperlipidemia, a risk factor for atherosclerosis, mainly via induction of sterol regulatory element-binding protein 1c (SREBP-1c)-mediated lipogenesis in the liver. In this embodiment, macrophage gene therapy is applied to separate the adverse effects (in liver) from the anti-atherogenic function (in macrophages) of LXR. Atherosclerosis can be reduced by long-lasting, effective enhancement of LXR expression in macrophages achieved by ex vivo transduction with lentiviral vectors carrying a SMP and subsequent syngeneic transplantation of HSCs. The goal of this study is to apply the same experimental procedures described above to enhance LXR expression driven by a SMP in macrophages and thus reduce atherosclerosis in the well-studied LDLR −/− murine model. Expression of transgenic LXR is examined and atherosclerotic lesions quantified by computer-assisted image analysis. Atherosclerotic plaques are shown to be decreased in experimental mice compared with controls.

Liver X receptors—good targets for the treatment of atherosclerosis—Liver X receptors (LXRs) are sterol-responsive transcription factors that regulate expression of genes involved in cholesterol metabolism and homeostasis[15]. LXRα and LXRβ have a high degree of amino acid identity (78%) and similar ligand-binding affinity to endogenous oxysterols. While the expression of LXRα is limited to organs such as liver, intestine, kidney, adipose tissue, and adrenals, LXRβ is expressed ubiquitously[15]. Both LXRα and LXRβ are expressed in wild type mouse macrophages. Studies using LXRα−/− and LXRβ−/− indicated that the two LXR genes are functionally redundant in this cell type[7]. In macrophages, these oxysterols may be derived from internalized oxLDL or generated intracellularly through modification of cholesterol[16]. Activation of LXR in macrophages induces expression of several genes involved in lipid metabolism and reverse cholesterol transport, including ABCA1, ABCG1 and ApoE (19). Using DNA microarrays, Joseph and colleagues examined the effect of LXR activation on LPS-induced gene transcription in thioglycolate-elicited peritoneal macrophages[17]. They identified genes regulated by LXR ligand (GW3965) in LXR-positive, but not Nr1h3−/−Nr1h2−/− cells. As expected, the most highly induced genes were those involved in lipid metabolism, including established LXR target genes such as ABCA1. A large cluster of genes involved in the macrophage innate immune response was inhibited by the LXR agonist. These genes encoded iNOS and COX-2, cytokines such as IL-6, IL-1, and granulocyte colony-stimulating factor (G-CSF), chemokines such as monocyte chemoattractant protein-1 (MCP-1), MCP-3, macrophage inflammatory protein-1 (MIP-1) and interferon-inducible protein-10 (IP-10), and the metalloproteinase MMP-9. The specificity of GW3965 was confirmed as the expression of genes involved in other cellular processes was not significantly altered by LXR ligand 7 Thus, in activated macrophages, the cholesterol efflux pathway and the innate immune response are reciprocally regulated by LXRs, implying a potential anti-atherogenic role of the two receptor/transcription factors in the lesion development.

Studies have demonstrated that LXRs exert an important athero-protective effect in macrophages[7,16]. LXR agonists induce expression of ABCA1 and inhibit inflammatory gene (MMP-9) expression in the aortas of atherosclerotic mice. Systemic administration of an LXR agonist reduced atherosclerosis in LDLR−/− and ApoE−/− mice[17]. Conversely, loss of LXR expression from bone marrow increases lesion formation in these same models[7]. Therefore, the LXR family may function as master transcriptional regulators that confer resistance to atherogenesis.

LXR−/− mice are deficient in the expression of several genes in the lipogenic pathway, including sterol regulatory element binding protein 1c (SREBP-1c)[7,18,19]. Administration of the synthetic LXR ligands to mice triggers induction of the lipogenic pathway and elevates plasma and hepatic triglyceride levels[20]. The primary mechanism by which LXR agonists stimulate lipogenesis appears to be through direct activation of the SREBP-1c promoter in liver, white adipose tissue, and intestine. In addition, direct actions of LXR on certain lipogenic genes such as hepatic FAS, Angptl3, and PLTP are also likely to contribute to the ability of LXR agonists to cause hypertriglyceridemial[6,21,22]. Thus, although they have many beneficial effects on cholesterol metabolism as described above, LXR agonists have certain undesirable effects. At present, the lipogenic activity of LXR agonists represents a significant obstacle to the development of these compounds as drugs. Macrophage LXR expression will avoid causing the hepatic lipogenesis and liver-related hypertriglyceridemia.

Synthetic promoters—Many viral promoters, such as CMV, show strong promoter activity, but are generally non-selective, acting in a wide variety of cell types. Lacking cell specificity, they may drive inappropriate gene expression in non-target tissues and cells causing additional problems for the recipient. Moreover, viral promoters are vulnerable to gene silencing[31,32] which is a major problem encountered both in transgenic mice and in gene therapy. Skeletal muscle is an attractive target for somatic gene therapy. However, relatively low levels of expression from naturally occurring promoters have limited the use of muscle as a gene therapy target. By random assembly of E-box, MEF-2, TEF-1, and SRE sites into synthetic promoter recombinant libraries, and screening of hundreds of individual clones for transcriptional activity in vitro and in vivo, several artificial promoters were isolated whose transcriptional potencies greatly exceed those of natural myogenic and viral gene promoters[33]. Synthetic promoters are usually small in size and provide more flexibility in constructing viral vectors. In gene therapy generally, there is a pressing need for strong tissue or cell-specific promoters; in the context of this invention, strong macrophage specific promoters.

The macrophage LXR gene enhancement therapy, devoid of the adverse hyperlipidemic side effects, represents a novel strategy for treatment of atherosclerotic diseases, as the LXR appears to induce elevation of plasma HDL levels and reduction of vascular inflammation, in contrast to the statin class of lipid-lowering drugs.

A proof-of-concept study has been conducted, demonstrating that macrophage apoE replacement can ameliorate atherosclerosis in apoE−/− mice by ex vivo transduction with lentiviral vectors carrying a SMP and subsequent transplantation of bone marrow stem cells.

The apoE- and LDLR-null mice are the best characterized animal models for atherosclerosis research. Transgenic mice are made with the super promoter-EGFP cassette, flanked by a 1.2 kb DNA fragment of chromatin insulator to avoid silencing of the transgene. Transgene copy number is assessed by Southern blot analysis. To check monocyte/macrophage expression of the transgene, peripheral blood leukocytes, peritoneal cells, bone morrow cells, and splenocytes are isolated and analyzed by FACS for co-expression expression of EGFP with leukocyte markers. EGFP transcripts and protein in various tissues is tested by Northern (or RT-PCR) and Western blot analyses, respectively.

Figure 3:
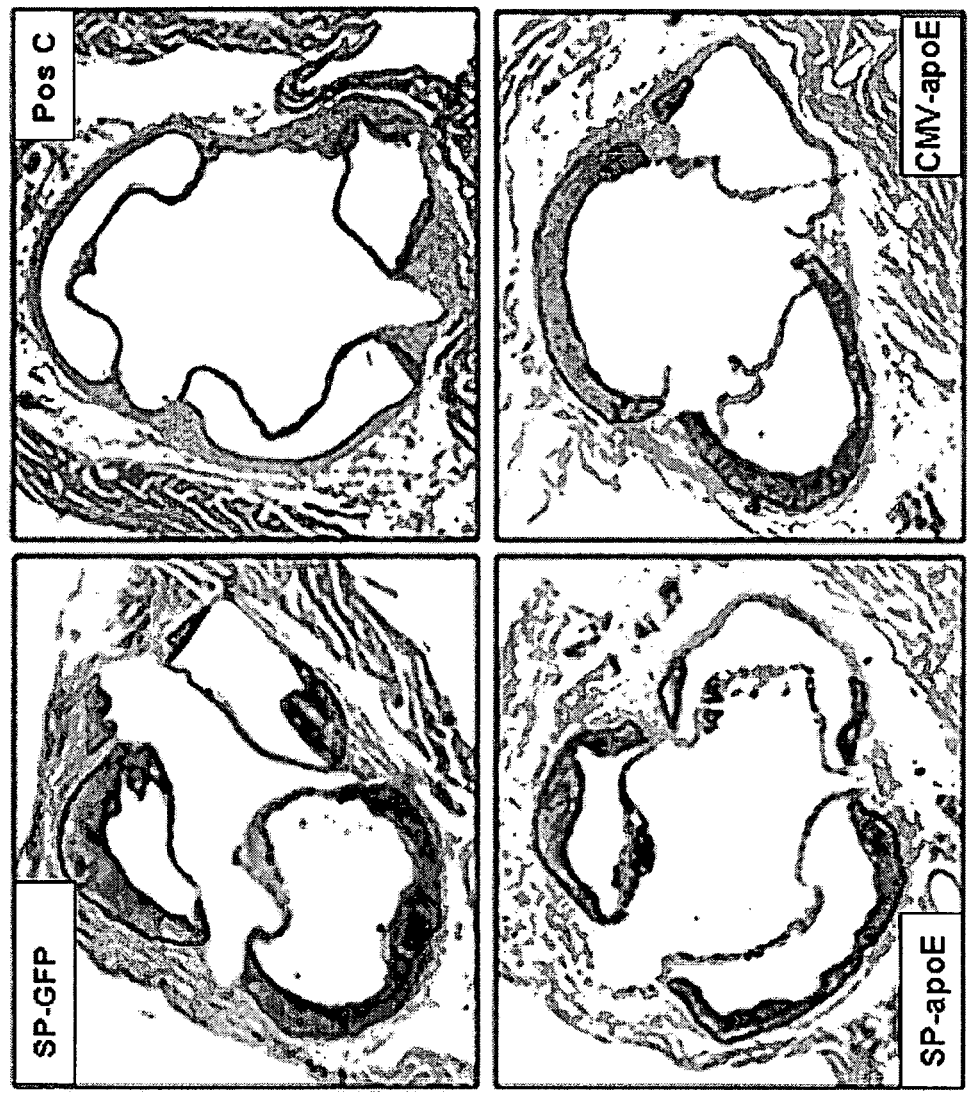
FIG. 3. Macrophage apoE replacement reduces atherosclerotic lesion. Frozen sections of 8 μm thick were cut from the region of the proximal aorta starting from the end of the aortic sinus and continuing distally according to the technique of Paigen et al. Sections were stained with oil red O and counterstained with hematoxylin. Quantification of lesion area was performed on 15 sections per animal by digitizing morphometry and was reported in mean $\mu m^2$/section. Representative aorta lesion area from each group as indicated (40×).

A SMP drives transgenic apoE expression in lentiviral vectors-transduced bone marrow-derived macrophages and ameliorates atherosclerosis in apoE−/− mice: Macrophage production of apoE in the artery wall has been demonstrated to provide protection against atherosclerotic lesion development (6). To test the usefulness of the SMP and the feasibility of the macrophage gene therapy approach, an experiment was performed to replace apoE gene expression in macrophages of apoE−/− mice using the procedures described herein. Briefly, bone marrow cells were harvested from either apoE−/− (Table 2, Group A-D) or wild type C57BL/6 (Group E) mice, transduced with high titers ($3 \times 10^8$ IU/ml for group A and $1 \times 10^8$ IU/ml for groups B,C) of various lentivectors as indicated, and transplanted into lethally irradiated syngeneic apoE−/− recipients. The recipient mice were 10 weeks of age. At week 16 post-transplantation, the mice were sacrificed for collections of tissues, blood, and peritoneal macrophages. Transgenic human apoE in serum or secreted from cultured peritoneal macrophages was analyzed by Western blotting. Aortic atherosclerotic lesion area was examined with immunohistochemistry and quantified by computer-assisted image analysis. There was no apoE detected in serum from mice of Group C or D, whereas a significant amount of serum apoE was observed in serum from mice of Group A or Group B. Levels of serum apoE in mice transduced with lentivectors carrying a ubiquitous-active CMV promoter were high and may be contributed by multiple cell types in blood. In contrast, levels of serum apoE in mice transduced with lentivectors carrying a SMP were relatively low and may be due to monocytes/macrophage being the only or major source of apoE production. This claim is supported by the observation that peritoneal macrophages from mice transduced with lentivectors carrying either a SMP or a CMV promoter secreted comparable amounts of apoE. Moreover, higher titer of lentivectors carrying a CMV promoter, resulting in higher copy numbers of viral integration, may correlate to higher apoE expression. GFP expression in the peripheral blood of group C mice was analyzed by FACS. Using Mac-1/CD11b as a macrophage/myeloid marker, GFP was shown to be expressed strongly (~$2 \times 10^3$ relative units) in monocytes/macrophages, but weakly (~$6 \times 10^1$ relative units) in some Mac-1/CD11b negative leukocytes and none in majority of Mac-1/CD11b negative cells. These data demonstrate strong macrophage-specific activity of the SMP used in this experiment. However, 58.5% of the Mac-1/CD11b positive cells were GFP negative, suggesting that GFP or apoE expression can be increased dramatically. Most importantly, experimental mice (n=7) given transplants transduced with lentivectors carrying apoE had significant smaller lesions than control mice (n=7) (FIG. 3).

As noted above, LDLR−/− mice are used as the model of atherosclerosis. Bone marrow cells are collected, transduced ex vivo with lentiviral vectors expressing human or mouse LXR genes driven by a SMP, and then infused back into syngeneic, lethally irradiated recipients of 6-8 weeks of age. The mice are placed on a Western diet one week after transplantation. At week 6 and week 20, expression of transgenic LXRs is examined in peritoneal macrophages using Western blotting and/or immunohistochemical staining. LXR induced macrophage expression of genes involved in lipid metabolism such as ABCA1, apoE and genes involved in immune response such as iNOS, COX-2, IL-6, IL-1β is measured at mRNA and/or protein levels. Plasma cholesterol levels are determined biweekly. Atherosclerotic lesions are examined by immunohistochemistry and quantified by computer-assisted image analysis.

Mice LDLR−/−, and C57BL/6 female mice are purchased from The Jackson Laboratory. Eight mice are used for each experimental or control group. BMT recipient mice are given drinking water with 100 mg/liter neomycin and 10 mg/liter polymyxin B for 3 days before and 14 days after transplantation.

Lentiviral vector construction The replication-incompetent third generation lentivectors are gifts from Dr. Didier Trono (Geneva, Switzerland) (67). They are self-inactivating, stripped of all HIV accessory proteins, and strictly dependent on complementation with Rev protein in trans. EGFP gene or LXRβ cDNA (a gift from Dr. Ronald Evans, The Salk Institute) is inserted downstream of a SMP in a lentivector.

Lentiviral vector production VSV-G-pseudotyped lentivector-SP-LXRα or -SP-LXRβ particles are generated by transient cotransfection of the specific transfer vector plasmid with the three packaging plasmids (pMDLg/pRRE, the gag-pol plasmid; pRSV-Rev, a Rev expressing plasmid; and pMD.G, a VSV-G envelope expressing plasmid) into 293T cells as described. Lentivector supernatant is filtered, concentrated by twice ultracentrifugation (55,000 g for 3 hours), and stored at 70° C. (33, 34). The viral titers are estimated by transduction of 293T cells with the CMV-EGFP lentivector processed simultaneously.

Bone marrow cell culture, lentiviral infection, and transplantation Isolation, transduction, and transplantation of BM cells from wildtype or LDLR−/− mice are done essentially as described[29]. Briefly, bone marrow (BM) is obtained from femurs and tibias of 6- to 8-week-old male mice 4 days after i.v. injection of 5-FU at a dose of 100 mg/kg body weight.

Bone marrow cells are treated with Lympholyte-M (Gibco, Cat # 10639-011) for enrichment of HSCs, and stimulated overnight in StemPro medium along with 6 ng/ml of IL-3, 10 ng/ml of IL-6, 10 ng/ml of murine IL-1α and 100 ng/ml of Stem Cell factor. The next day, cells are pelleted and resuspended in 0.85 ml of the aforementioned medium containing the same growth factor combination with concentrated, vesicular stomatitis virus glycoprotein-G-pseudotyped SP-LXR lentivectors at a final virus concentration of $2\text{-}10\times10^9$ infectious units/ml. Infection is performed for 5 h on fibronectin-coated Petri dishes in the presence of 8 μg/ml protamine sulfate. After infection, $2\times10^6$ cells are transplanted, without selection, by i.v. injection into each syngeneic recipient given 950 cGy of total body irradiation.

Real-time PCR analysis of proviral copy number Vector copy number in mouse peripheral blood cells is determined by real-time quantitative TaqMan polymerase chain reaction (PCR) (PE Applied Biosystems, Foster City, Calif.). Primers and probes are used that are completely within the extended LTR lentivector sequence and can be used regardless of the transgene, as described above. The following incubation periods are applied for all primer sets: 2 min at 50° C., 10 min at 95° C., 40 cycles of 15 sec at 95° C., and 60 sec and 60° C. Standard curves for the TaqMan™ PCR analyses are obtained by using vector single-copy clones of NIH 3T3 cells transduced with the lentiviral vector.

Immunoblotting Macrophages are homogenized in PBS containing 1% NP-40, 0.5% sodium deoxycholate, 0.1% SDS, and protease inhibitors (Complete Protease Inhibitor Cocktail Tablets, Roche Molecular Biochemicals), and a soluble protein-fraction is obtained after collection of the supernatant after centrifugation. Protein concentration is determined with the Bio-Rad calorimetric assay system (Bio-Rad Laboratories, Inc. Hercules, Calif.). Aliquots of each sample (150 μg protein) are separated on a 10% SDS-polyacrylamide gel and transferred to nitrocellulose membrane (Hybond-C-Extra, Amersham Pharmacia Biotech). LXR proteins are immunochemically detected using a commercially available antibody specific to LXRα (no. SC-1206, Santa Cruz Biotechnology, Inc.), at a dilution of 2 μg/ml, and signal detection is achieved using ECL chemiluminescence (Amersham Pharmacia Biotech) according to the manufacturer's instructions. An antibody that recognizes both LXR proteins is available from EMD Bioscience (San Diego). Antibodies against NOS-2 (SC-651) and COX-2 (160106) are from Santa Cruz Biotechnology and Cayman Chemicals, respectively[40].

Atherosclerotic lesion analysis Twenty weeks after transplantation, animals are sacrificed for examination of atherosclerosis as described previously. Briefly, mice are anaesthetized by ketamine (10 mg/kg body weight). After perfusion with phosphate-buffered saline (PBS) and subsequently with formal-sucrose (4% paraformaldehyde and 5% sucrose in PBS, pH 7.4), the top half of the heart is removed and immersed in cold PBS for 2 h and then in fornal-sucrose overnight at 4° C. The hearts are embedded in OCT, snap frozen in liquid nitrogen, and stored at −70° C. until sectioning. Serial sections of 8 μm thickness are cut through a −250 μm segment of the aortic valve. Five sections, each separated by 40 μm encompassing 200 μm of the valve, are examined from each mouse. The sections are stained with Oil Red O to reveal the bright red staining of the lesions and counterstained with hematoxylin. The Oil Red O-stained areas of each section are quantitated using a computer-assisted video imaging system.

Statistical Analyses. Results are analyzed by one-way ANOVA and/or Student's unpaired t test by using GraphPad (San Diego) PRISM.

REFERENCE LIST FOR EXAMPLE 3

1. Glass C K, Witztum J L. Atherosclerosis. the road ahead. *Cell.* 2001; 104:503-516.
2. Smith J D, Trogan E, Ginsberg M, Grigaux C, Tian J, Miyata M. Decreased atherosclerosis in mice deficient in both macrophage colony-stimulating factor (op) and apolipoprotein E. *Proc Natl Acad Sci USA.* 1995; 92:8264-8268.
3. Smith J D. An A+ for macrophages in reducing atherosclerosis? *Arterioscler Thromb Vasc Biol.* 2001; 21:1710-1711.
4. Fazio S, Babaev V R, Murray A B, Hasty A H, Carter K J, Gleaves L A, Atkinson J B, Linton M F. Increased atherosclerosis in mice reconstituted with apolipoprotein E null macrophages. *Proc Natl Acad Sci USA.* 1997; 94:4647-4652.
5. Hasty A H, Linton M F, Brandt S J, Babaev V R, Gleaves L A, Fazio S. Retroviral gene therapy in ApoE-deficient mice: ApoE expression in the artery wall reduces early foam cell lesion formation. *Circulation.* 1999; 99:2571-2576.
6. Aiello R J, Brees D, Bourassa P A, Royer L, Lindsey S, Coskran T, Haghpassand M, Francone O L. Increased atherosclerosis in hyperlipidemic mice with inactivation of ABCA1 in macrophages. *Arterioscler Thromb Vasc Biol.* 2002; 22:630-637.
7. Tangirala R K, Bischoff E D, Joseph S B, Wagner B L, Walczak R, Laffitte B A, Daige C L, Thomas D, Heyman R A, Mangelsdorf D J, Wang X, Lusis A J, Tontonoz P, Schulman I G. Identification of macrophage liver X receptors as inhibitors of atherosclerosis. *Proc Natl Acad Sci USA.* 2002; 99:11896-11901.
8. Chawla A, Boisvert W A, Lee C H, Laffitte B A, Barak Y, Joseph S B, Liao D, Nagy L, Edwards P A, Curtiss L K, Evans R M, Tontonoz P. A PPAR gamma-LXR-A-BCA1 pathway in macrophages is involved in cholesterol efflux and atherogenesis. *Mol Cell.* 2001; 7:161-171.
9. Okazaki H, Osuga J, Tsukamoto K, Isoo N, Kitamine T, Tamura Y, Tomita S, Sekiya M, Yahagi N, Iizuka Y, Ohashi K, Harada K, Gotoda T, Shimano H, Kimura S, Nagai R, Yamada N, Ishibashi S. Elimination of cholesterol ester from macrophage foam cells by adenovirus-mediated gene transfer of hormone-sensitive lipase. *J Biol Chem.* 2002; 277:31893-31899.
10. Makowski L, Boord J B, Maeda K, Babaev V R, Uysal K T, Morgan M A, Parker R A, Suttles J, Fazio S, Hotamisligil G S, Linton M F. Lack of macrophage fatty-acid-binding protein aP2 protects mice deficient in apolipoprotein E against atherosclerosis. *Nat Med.* 2001; 7:699-705.
11. Boring L, Gosling J, Cleary M, Charo I F. Decreased lesion formation in CCR2−/− mice reveals a role for chemokines in the initiation of atherosclerosis. *Nature.* 1998; 394:894-897.
12. Cybulsky M I, Iiyama K, Li H, Zhu S, Chen M, Iijyama M, Davis V, Gutierrez-Ramos J C, Connelly P W, Milstone D S. A major role for VCAM-1, but not ICAM-1, in early atherosclerosis. *J Clin Invest.* 2001; 107:1255-1262.
13. Babaev V R, Gleaves L A, Carter K J, Suzuki H, Kodama T, Fazio S, Linton M F. Reduced atherosclerotic lesions in mice deficient for total or macrophage-specific expression of scavenger receptor-A. *Arterioscler Thromb Vasc Biol.* 2000; 20:2593-2599.
14. Stein O, Thiery J, Stein Y. Is there a genetic basis for resistance to atherosclerosis? *Atherosclerosis.* 2002; 160: 1-10.

15. Repa J J, Mangelsdorf D J. The liver X receptor gene team: potential new players in atherosclerosis. *Nat Med.* 2002; 8:1243-1248.
16. Tontonoz P, Mangelsdorf D J. Liver x receptor signaling pathways in cardiovascular disease. *Mol Endocrinol.* 2003; 17:985-993.
17. Joseph S B, Castrillo A, Laffitte B A, Mangelsdorf D J, Tontonoz P. Reciprocal regulation of inflammation and lipid metabolism by liver X receptors. *Nat Med.* 2003; 9:213-219.
18. Repa J J, Liang G, Ou J, Bashmakov Y, Lobaccaro J M, Shimomura I, Shan B, Brown M S, Goldstein J L, Mangelsdorf D J. Regulation of mouse sterol regulatory element-binding protein-1c gene (SREBP-1c) by oxysterol receptors, LXRalpha and LXRbeta. *Genes Dev.* 2000; 14:2819-2830.
19. Schultz J R, Tu H, Luk A, Repa J J, Medina J C, Li L, Schwendner S, Wang S, Thoolen M, Mangelsdorf D J, Lustig K D, Shan B. Role of LXRs in control of lipogenesis. *Genes Dev.* 2000; 14:2831-2838.
20. Grefhorst A, Elzinga B M, Voshol P J, Plosch T, Kok T, Bloks V W, van der Sluijs F H, Havekes L M, Romijn J A, Verkade H J, Kuipers F. Stimulation of lipogenesis by pharmacological activation of the liver X receptor leads to production of large, triglyceride-rich very low density lipoprotein particles. *J Biol Chem.* 2002; 277:34182-34190.
21. Inaba T, Matsuda M, Shimamura M, Takei N, Terasaka N, Ando Y, Yasumo H, Koishi R, Makishima M, Shimomura I. Angiopoietin-like protein 3 mediates hypertriglyceridemia induced by the liver X receptor. *J Biol Chem.* 2003; 278: 21344-21351.
22. Joseph S B, Laffitte B A, Patel P H, Watson M A, Matsukuma K E, Walczak R, Collins J L, Osborne T F, Tontonoz P. Direct and indirect mechanisms for regulation of fatty acid synthase gene expression by liver X receptors. *J Biol Chem.* 2002; 277:11019-11025.
23. Cavazzana-Calvo M, Hacein-Bey S, de Saint B G, Gross F, Yvon E, Nusbaum P, Selz F, Hue C, Certain S, Casanova J L, Bousso P, Deist F L, Fischer A. Gene therapy of human severe combined immunodeficiency (SCID)-X1 disease. *Science.* 2000; 288:669-672.
24. Aiuti A, Slavin S, Aker M, Ficara F, Deola S, Mortellaro A, Morecki S, Andolfi G, Tabucchi A, Carlucci F, Marinello E, Cattaneo F, Vai S, Servida P, Miniero R, Roncarolo M G, Bordignon C. Correction of ADA-SCID by stem cell gene therapy combined with nonmyeloablative conditioning. *Science.* 2002; 296:2410-2413.
25. Hacein-Bey-Abina S, Le Deist F, Carlier F, Bouneaud C, Hue C, De Villartay J P, Thrasher A J, Wulffraat N, Sorensen R, Dupuis-Girod S, Fischer A, Davies E G, Kuis W, Leiva L, Cavazzana-Calvo M. Sustained correction of X-linked severe combined immunodeficiency by ex vivo gene therapy. *N Engl J Med.* 2002; 346:1185-1193.
26. Hacein-Bey-Abina S, von Kalle C, Schmidt M, Le Deist F, Wulffraat N, McIntyre E, Radford I, Villeval J L, Fraser C C, Cavazzana-Calvo M, Fischer A. A serious adverse event after successful gene therapy for X-linked severe combined immunodeficiency. *N Engl J Med.* 2003; 348: 255-256.
27. Hacein-Bey-Abina S, de Saint B G, Cavazzana-Calvo M. Gene therapy of X-linked severe combined immunodeficiency. *Methods Mol Biol.* 2003; 215:247-259.
28. Wu X, Li Y, Crise B, Burgess S M. Transcription start regions in the human genome are favored targets for MLV integration. *Science.* 2003; 300:1749-1751.
29. Imren S, Payen E, Westerman K A, Pawliuk R, Fabry M E, Eaves C J, Cavilla B, Wadsworth L D, Beuzard Y, Bouhassira E E, Russell R, London I M, Nagel R L, Leboulch P, Humphries R K. Permanent and panerythroid correction of murine beta thalassemia by multiple lentiviral integration in hematopoietic stem cells. *Proc Natl Acad Sci USA.* 2002; 99:14380-14385.
30. Pawliuk R, Westerman K A, Fabry M E, Payen E, Tighe R, Bouhassira E E, Acharya S A, Ellis J, London I M, Eaves C J, Humphries R K, Beuzard Y, Nagel R L, Leboulch P. Correction of sickle cell disease in transgenic mouse models by gene therapy. *Science.* 2001; 294:2368-2371.
31. Persons D A, Nienhuis A W. Gene therapy for the hemoglobin disorders: past, present, and future. *Proc Natl Acad Sci USA.* 2000; 97:5022-5024.
32. Malik P, Krall W J, Yu X J, Zhou C, Kohn D B. Retroviral-mediated gene expression in human myelomonocytic cells: a comparison of hematopoietic cell promoters to viral promoters. *Blood.* 1995; 86:2993-3005.
33. Li X, Eastman E M, Schwartz R J, Draghia-Akli R. Synthetic muscle promoters: activities exceeding naturally occurring regulatory sequences. Nat Biotechnol. 1999; 17:241-245.
34. Clarke S, Gordon S. Myeloid-specific gene expression. *J Leukoc Biol.* 1998; 63:153-168.
35. Ward A C, Loeb D M, Soede-Bobok A A, Touw I P, Friedman A D. Regulation of granulopoiesis by transcription factors and cytokine signals. *Leukemia.* 2000; 14:973-990.
36. Shivdasani R A, Orkin S H. The transcriptional control of hematopoiesis. *Blood.* 1996; 87:4025-4039.
37. Tenen D G, Hromas R, Licht J D, Zhang D E. Transcription factors, normal myeloid development, and leukemia. *Blood.* 1997; 90:489-519.
38. Roberts W M, Shapiro L H, Ashmun R A, Look A T. Transcription of the human colony-stimulating factor-1 receptor gene is regulated by separate tissue-specific promoters. *Blood.* 1992; 79:586-593.
39. Dziennis S, Van Etten R A, Pahl H L, Morris D L, Rothstein T L, Blosch C M, Perlmutter R M, Tenen D G. The CD11b promoter directs high-level expression of reporter genes in macrophages in transgenic mice. *Blood.* 1995; 85:319-329.
40. Tolba K A, Bowers W J, Hilchey S P, Halterman M W, Howard D F, Giuliano R E, Federoff H J, Rosenblatt J D. Development of herpes simplex virus-1 amplicon-based immunotherapy for chronic lymphocytic leukemia. *Blood.* 2001; 98:287-295.

Example 4

Chronic Granulomatous Disease

In this embodiment, the present invention is directed to a treatment for chronic granulomatous disease (CGD) through hematopoietic stem cell (HSC)-mediated gene therapy. The sequence of events would be that HSC are mobilized by G-CSF, collected via apheresis, transduced ex vivo with lentiviral vectors expressing therapeutic genes (e.g., gp91$^{phox}$, p47$^{phox}$ or others) in mature phagocytes driven by a strong myeloid-specific promoter, and then infused back into the same individual CGD patient. The expected results are full restoration of the respiratory burst activity in mature phagocytic leukocytes and long-term correction of the defect in host defense.

A gp91$^{phox}$ variant (gp91$^{phox}$-T196F) has been developed that is enzymatically super-active, 7-fold over the wild-type protein.

This aspect of the present invention is directed to the correction of $gp91^{phox}$-deficient mice by syngeneic transplantation of HSC transduced ex vivo with lentivector expressing $gp91^{phox}$ encoding nucleic acid in mature phagocytes driven by super-myeloid promoters (SMP). Human $gp91^{phox}$ and its variant $gp91^{phox}$-T196F cDNA are separately inserted into Lenti-SMP-GFP to replace the EGFP gene. The resulting constructs, Lenti-SMP-hgp91$^{phox}$, Lenti-SMP-hgp91$^{phox}$-r196F, and the parent vector, Lenti-SMP-GFP, are co-transfected respectively by Fugene6 reagents together with the three packaging plasmids into 293T cells to produce lentiviral particles, which are then concentrated by ultra-centrifugation and used to transduce mouse X-CGD bone marrow stem cells ex vivo for 5-6 hours. The transduced bone marrow cells are infused into lethally irradiated X-CGD recipient mice by tail vein injection. For each construct, 20 mice are used as recipients and analyzed for a proportion of superoxide-generating cells in peripheral neutrophils by nitroblue tetrazolium (NBT) testing or dihydrorhodamine 123 (DHR) flow cytometric analysis. Whole cell superoxide production is quantified by chemiluminescence with a Diogenes kit and by spectrophotometric assay of cytochrome C reduction. Expression of the transgenes is determined in various lineages of bone marrow by RT-PCR and Western blot analysis. Provirus copy number in the genome of blood cells is measured using real-time PCR. Reconstitution of host defense is examined by A fumigatus and B cepacia challenges. Secondary X-CGD transplantation is carried out to confirm integration of the functional provirus in reconstituting stem cells.

It is a further aspect of this embodiment of the present invention to correct $p47^{phox}$-deficient mice by syngeneic transplantation of HSC transduced ex vivo with lentivector expressing the $gp47^{phox}$ gene in mature phagocytic leukocytes driven by SMP. Both murine and human $p47^{phox}$ cDNA are used. The assessment of reconstitution of NADPH oxidase function and host defense is done as described herein.

Phagocyte NADPH oxidase: Polymorphonuclear neutrophils and macrophages constitute the first line of host defense against many pathogenic bacteria and fungi (1). Their ability to kill invading microorganisms depends to a large extent on superoxide and derivative microbicidal oxidants generated by NADPH oxidase (also referred to as respiratory burst oxidase). The superoxide-generating NADPH oxidase is a coordinated assembly of the membrane-associated heterodimeric flavocytochrome $b_{558}$ ($gp91^{phox}$ plus $p22^{phox}$) with four cytosolic factors, $p67^{phox}$, $p47^{phox}$, $p40^{phox}$, and a small Rho-family GTP-ase (Rac1 or Rac2) (2, 3). Upon activation of the oxidase in response to physiologic stimuli such as phagocytosis, the cytoplasmic subunits $p47^{phox}$, $p67^{phox}$, and $p40^{phox}$ translocate to the membrane-bound cytochrome. NADPH is oxidized to NADP$^+$, and electrons are transported down a reducing potential gradient to flavin adenine dinucleotide (FAD) and then to two non-identical heme groups. On the vacuolar or extracellular side of the membrane, the final step in the electron transport chain occurs when two molecules of diatomic oxygen each accept an electron and are converted to superoxide anion. The net equation involves the reduction of two molecules of $O_2$ to two molecules of superoxide anion ($O_2^-$) at the expense of one molecule of NADPH. Superoxide, a relatively weak microbicidal oxidant, is then metabolized to the more toxic hydrogen peroxide, hypohalous acids (bleach in the neutrophil), and hydroxyl anion by other reactions (2, 4-8). Whereas $p22^{phox}$ is ubiquitously expressed, $gp91^{phox}$, $p47^{phox}$, $p67^{phox}$, and $p40^{phox}$ exhibit myeloid-specific expression, which is controlled to a large extent by the myeloid transcription factor PU.1 (9-13). B-cells contain all of the components of the phagocyte NADPH oxidase, and generate superoxide upon stimulation with various agonists, but at a far lower level than neutrophils, perhaps due to lower levels of the phox proteins. However, several non-phagocytic cells such as endothelial cells, fibroblasts, and renal mesangial cells contain NADPH oxidase-like components and can generate low levels of superoxide anion. A number of homologues of the membrane-bound core enzyme subunit $gp91^{phox}$ have been identified. Members of this family of NADPH oxidase (NOX) proteins have a different tissue distribution from $gp91^{phox}$ (14). One member, NOX1, is expressed predominantly in the epithelial cells of the gut, particularly the colon (15-17). There are also reports describing homologues of $p67^{phox}$ and $p47^{phox}$ (NOXA1 and NOXO1, respectively), which like NOX1, are expressed in the gut epithelial cells (18-20).

These co-factors interact with NOX1 in an unknown manner to stimulate both constitutive and agonist-induced superoxide. Initial studies suggest that the levels of superoxide generated by the human NOX1 system are far less than those seen with the phagocyte system, suggesting that the function of NOX1/NOXA1/NOXO1 may not necessarily be that of host defense.

CGD: a rare, but life-threatening disorder: Chronic granulomatous disease is a rare, inherited disorder in which superoxide generation by the phagocyte NADPH oxidase is absent or markedly deficient. CGD can result from a defect in any of the four phox subunit genes, with 60%-80% of cases due to the X-linked $gp91^{phox}$ deficiency, one-third of cases due to the autosomal recessive $p47^{phox}$ deficiency, and ~2%-3% each due to the autosomal recessive $p22^{phox}$ deficiency or $p67^{phox}$ deficiency (21-23). Victims suffer from recurrent and often life-threatening bacterial and fungal infections. CGD is also characterized by abnormally exuberant inflammatory responses leading to granuloma formation, manifested by granulomatous enteritis, genitourinary obstruction, and poor wound healing (6, 7, 23).

While daily administration of prophylactic oral antibiotics and thrice-weekly administration of prophylactic subcutaneous interferon-γ have been demonstrated to decrease the frequency of infection, CGD continues to be associated with significant morbidity and mortality, with a current mortality of two deaths per 100 patient years. Patients with CGD often die at childhood or in young adult years. Few patients survive beyond 40 years of age. CGD occurs with a frequency of 4-5 per million, appearing to affect all ethnic and racial populations. Whereas the X-linked form affects only males, the autosomal recessive forms affect males and females equally. Female carriers of the X-linked form of CGD are mosaics for the CGD phenotype (2, 7, 21, 22).

CGD can be cured by identically matched sibling allogeneic bone marrow transplant, but the difficulty of finding good matches and the considerable morbidity and mortality associated with allogeneic transplantation have made this treatment an impractical option for most patients. Since bone marrow transplantation can cure CGD, this satisfies an important criterion for a disease potentially treatable with gene transfer into the hematopoietic stem cells that give rise to granulocytes and monocytes (5, 6, 21, 22).

CGD: a good target for gene therapy: Because CGD results from a single-gene defect in hematopoietic stem cells, and mouse models of CGD have been developed that recapitulate the human disease, CGD has become an attractive target disease for hematopoietic cell gene replacement therapy. Autologous marrow transplantation provides an opportunity for the ex vivo introduction of normal genes into hematopoietic stem cells, using retroviruses or other vector systems, for the correction of genetic diseases. Autologous marrow transplantation avoids complications of allogeneic marrow transplantation, such as graft-versus-host disease (21, 22, 24-26).

CGD is considered as a good candidate for gene therapy by correction of autologous hematopoietic stem cells for additional reasons. Clinical observations suggest that even low percentages of normal circulating neutrophils can provide significant protection against infection. Female carriers of the X-linked form of CGD are mosaics for the CGD phenotype. Some of these carriers have only 5% to 10% of their neutrophils capable of superoxide generation yet show no apparent increase in infections, although others experience recurrent bacterial infections similar to those seen in classic CGD. An important laboratory observation is that when normal and CGD neutrophils are mixed, a small amount of the hydrogen peroxide released extracellularly by normal cells diffuses into CGD cells, partially restoring microbicidal activity (27). Thus, one would expect a "bystander effect" to magnify the relative impact of provision of even very small numbers of oxidase-positive granulocytes to CGD patients. However, it must be pointed out that because the in vivo expression of a transgene (~20% of nonnal in corrected CGD cells) is much lower than that of endogenous genes, the proportion of corrected cells required for effective correction of CGD phenotype must be higher than the number of normal cells present in the CGD carriers (21, 22, 28, 29).

All patients with $p47^{phox}$-deficient and $p67^{phox}$-deficient forms of CGD have a protein-null phenotype, as do the vast majority of patients with $p22^{phox}$-deficient and $gp91^{phox}$-deficient CGD. Thus, in considering gene therapy for most patients with this disorder, the potential of a dominant negative effect of an abnormal protein on the ability of the normal gene to correct the abnormality need not be considered. However, some patients with X-linked CGD have point mutations in the $gp91^{phox}$ open reading frame that result in production of normal amounts of a non-functional protein. The same has been reported in rare patients with $p22^{phox}$-deficient CGD. Although a dominant negative effect on the product of a therapeutic gene is a theoretical limitation in these patients, this has not yet proven to be a significant issue (21, 22).

Super-active $gp91^{phox}$ mutant In a structure/function study of $gp91^{phox}$, a super-active variant of $gp91^{phox}$ (T196F) was generated, in which residue 196 is mutated from threonine to phenylalanine. PMA-stimulated superoxide generation was 7-fold greater when $gp91^{phox}$(T196F), versus wild-type $gp91^{phox}$, was used to reconstitute the NADPH oxidase in K562 cells. The mutant construct was made by QuikChange™ site-directed mutagenesis of $gp91^{phox}$ using sense primer CCTCCACCAAATTCATCCGGAGGTC (SEQ ID NO:5) and antisense primer GACCTCCGGATG AATTTGGTGGAGG (SEQ ID NO:6). The construct was sequenced and subcloned into fresh pcDNA3.1 (−) using NheI and XhoI.

$gp91^{phox}$ expressing lentivector production and transduction: Human $gp91^{phox}$, cDNA was inserted into a replication-incompetent third-generation lentivector (gift of Dr. Didier Trono, University of Geneva, Switzerland) downstream of the CMV promoter. The insert and its flanking regions were fully sequenced to confirm the identity. This lentivector is self-inactivating, stripped of all HIV accessory proteins, and strictly dependent on complementation of Rev protein in trans. VSV-G-pseudotyped lentivector CMV-EGFP particles were generated by transient co-transfection of the specific transfer vector plasmid with the three packaging plasmids (pMDLg/pRRE, the gag-pol plasmid; pRSV-Rev, a Rev expressing plasmid; and pMD.G, a VSV-G envelope expressing plasmid) into 293T cells by calcium phosphate or Fugen6 transfection reagents. Two days after transfection, the culture medium with various dilutions was used to transduce the A2 cell line (K562 cells bearing stably expressing human $p47^{phox}$ and $p67^{phox}$ vectors). Sixty hours later, the cells were processed for superoxide measurement using the Diogenes reagent. lentivector-$gp91^{phox}$ transduction could reconstitute NADPH oxidase activity in the cells in a dose-dependent manner.

In consideration of moving into clinical trials in future, both human $gp91^{phox}$ and human $p47^{phox}$ are used, in addition to murine $p47^{phox}$ gene, in the studies on CGD gene therapy. Human $gp91^{phox}$ and $p47^{phox}$ have been shown to work well in CGD mouse models (25, 32, 59). The murine and human $gp91^{phox}$ and $p47^{phox}$ protein sequences are highly similar, and exhibit cross-species complementation of respiratory burst oxidase activity in human and murine CGD phagocytes cultured in vitro (32).

Correction of $gp91^{phox}$ deficiency by bone marrow transplantation combined with ex vivo lentiviral transduction of a super-promoter (SP)-$gp91^{phox}$ gene.

Mice. C57B1/6J wild-type and X-CGD ($gp91^{phox}$−/) mice are obtained from available sources, such as Jackson Laboratories (Bar Harbor, Me.). Mice with a null allele for $gp91^{phox}$ were generated initially by targeted disruption of the $gp91^{phox}$ locus in 129-SV murine embryonic stem cells and backcrossed for more than 11 generations with wild-type C57B1/6J mice (25). Genotyping of mice was performed using a polymerase chain reaction of tail blood and confirmed by nitroblue tetrazolium (NBT) testing of peripheral blood (PB) neutrophils (1). Mice were maintained under specific pathogen-free conditions and fed autoclaved food and acidified water. BMT recipient mice are given drinking water with 100 mg/liter neomycin and 10 mg/liter polymyxin B for 3 days before and 14 days after transplantation.

Lentiviral vector construction The replication incompetent third generation lentivectors are gifts from Dr. Didier Trono (Geneva, Switzerland) (33). They are self-inactivating, stripped of all HIV accessory proteins, and strictly dependent on complementation of Rev protein in trans. The CMV-EGFP or EF1α-EGFP cassette is replaced with SP-hgp91$^{phox}$ and SP-hgp91$^{phox}$ (T196F).

Lentiviral vector production VSV-G-pseudotyped lentivector-SP-hgp91$^{phox}$ or -SP-hgp91$^{phox}$ (T196F) particles are generated by transient cotransfection of the specific transfer vector plasmid with the three packaging plasmids (pMDLg/pRRE, the gag-pol plasmid; pRSV-Rev, a Rev expressing plasmid; and pMD.G, a VSV-G envelope expressing plasmid) into 293T cells as described. Lentivector supernatant is filtered, concentrated by twice ultracentrifugation (55, 000 g for 3 hours), and stored at 70° C. (38, 41). The viral titers are estimated by transduction of 293T cells with the CMV-EGFP lentivector processed simultaneously.

Bone marrow cell culture, lentiviral infection and transplantation. Isolation, transduction, and transplantation of murine X-CGD BM cells is essentially as previously described (41). Briefly, bone marrow (BM) is obtained from femurs and tibias of 6- to 8-week-old X-CGD male mice 4 days after i.v. injection of 5-FU at a dose of 100 mg/kg body weight. Bone marrow cells are treated with Lympholyte-M (Gibco, Cat # 10639-011) for enrichment of HSCs, and stimulated overnight in StemPro medium along with 6 ng/ml of IL-3, 10 ng/ml of IL-6, 10 ng/ml of murine IL-1α and 100 ng/ml of Stem Cell factor. The next day, cells are pelleted and resuspended in 0.85 ml of the aforementioned medium containing the same growth factor combination with concentrated, vesicular stomatitis virus glycoprotein-G-pseudotyped Sp-gp91$^{phox}$ lentivectors at a final virus concentration of 2-10×10$^9$ infectious units/ml. Infection is performed for 5 h on fibronectin-coated Petri dishes in the presence of 8 μg/ml protamine sulfate. After infection, $2 \times 10^6$ cells are transplanted, without selection, by i.v. injection into each syngeneic recipient given 950 cGy of total body irradiation.

Secondary bone marrow transplantation (BMT) of X-CGD mice. Secondary BMT is performed to confirm that integration of functional lentivector-gp91$^{phox}$ provirus has occurred in reconstituting stem cells. BM from primary recipients is harvested 8 to 11 months post-transplantation and used for secondary transplants (32).

gp91$^{phox}$ expression in peripheral blood neutrophils and monocytes/macrophages. Gene-corrected gp91$^{phox}$-null, untreated control gp91$^{phox}$-null, and wild-type mice are bled by tail venisection. Two hundred microliters of whole blood is placed in polypropylene tubes and lysed with prewarmed ammonium chloride lysis buffer (pH 8.0). Cells are washed once and then resuspended in 400 μL of Hanks' Buffered Saline Solution (HBSS, without $Ca^{2+}$, $Mg^{2+}$, or phenol red), 0.5 g albumin (human fraction V), and 1 ml of 0.5 mol/L EDTA (pH 8.0). Cells are analyzed by flow cytometry to determine coexpression of murine CD3 (all leukocytes) and CD11b (myeloid cells), or Gr-1 (granulocytes) with human gp91$^{phox}$ detected using fluorescein isothiocyanate (FITC)-conjugated murine monoclonal antibody 7D5, which does not bind to mouse gp91$^{phox}$(25, 32)

Phagocyte NADPH oxidase activity. Nitroblue tetrazolium (NBT) dye (Sigma, St Louis, Mo.) reduction to formazan precipitate is used as a measure of superoxide production at the cellular level. The NBT assay is performed on tail blood PB neutrophils allowed to adhere to a glass slide for 15 to 20 minutes or on BM-derived neutrophils allowed to adhere to a chamber slide (Nunc, Inc, Naperville, Ill.) for 1 hour before activation of the respiratory burst oxidase with phorbol myristate acetate (PMA) (25). After incubation for 20 to 30 minutes at 37° C., slides are fixed and counterstained with safranin and the percentage of NBT-positive cells (containing blue-purple formazan deposits from reduction of NBT) determined by evaluating 100 to 200 cells using light microscopy. A similar protocol is used to examine phagocyte oxidase activity in peritoneal exudate macrophages.

NADPH oxidase activity is also tested by flow cytometric analysis of PB neutrophils using the dihydrorhodamine 123 (DHR) assay as described (66). Briefly, gene-corrected gp91$^{phox}$-null, untreated control gp91$^{phox}$-null, and wild-type mice are bled by tail venisection. Two hundred microliters of whole blood is placed in polypropylene tubes and lysed with prewarmed ammonium chloride lysis buffer (pH 8.0). Cells are washed once and then resuspended in 400 μl of Hanks' Buffered Saline Solution (HBSS, without Ca2+, Mg2+, or phenol red), 0.5 g albumin (human fraction V), and 1 ml of 0.5 mol/L EDTA (pH 8.0). 1.8 μl of 29 mmol/L DHR, and 5 μL of catalase (1,400 U/μL) are added to each tube, which is incubated for 5 min in a 37° C. shaking water bath. After 5 min, 100 μl of $3.2 \times 10^3$ nmol/L PMA is added to each reaction tube and the tubes are returned to the water bath for an additional 14 min. After incubation, all samples are immediately analyzed by flow cytometry using a FACSort™ (Becton Dickinson Immunocytometry System [BDIS], San Jose, Calif.) with CellQuest™ software (BDIS). Neutrophils are identified based on forward and side scatter characteristics. However, with mouse blood, it is not possible to establish a gate including most neutrophils that completely excludes lymphocytes. For this reason, the data for experimental p47$^{phox}$-/- mice are adjusted to reflect the results with wild-type mice. Each sample is run in the setup mode until a neutrophil acquisition gate is established, at which point only events in this gate are acquired. At least 10,000 events are collected in this gate in all studies. Analysis of neutrophil DHR fluorescence is performed by constructing a side scatter/FL2 dot plot and DHR-positive cells are identified by gating based on negative (untreated p47$^{phox}$-/-) and positive wild-type control samples. The experimental mice are bled and evaluated 1 week before transplantation (baseline analysis), 1 month after transplantation, and every 2 weeks thereafter.

NADPH oxidase activity is measured in a population of neutrophils using a luminol-based chemiluminescence assay (Diogenes) of superoxide production. Isolated neutrophils are resuspended in Krebs-Ringer-Glucose buffer (KRG), and kept on ice while viable counts are determined. $5 \times 10^5$ cells are transferred to luminometer tubes, pelleted, and resuspended in 75 μl KRG. 100 μl of Diogenes reagent (National Diagnostics) is added, and the baseline chemiluminescence at 37° C. is monitored for 0.5 seconds every minute for 3 minutes. Samples are kept at 37° C. between readings. 25 μl of 16 μg/ml PMA are added to stimulate superoxide production, and readings are taken every minute for 40 minutes in a Luminoskan luminometer (Promega). This is sufficient time in each case to reach a peak rate of photon emission. Total photon emission over this period is taken as the measurement of superoxide output.

A continuous assay of superoxide-dismutase-inhibitable ferricytochrome c reduction is used to quantitate absolute levels of superoxide formation (e.g., $nmol/min/10^6$ cells) by PMA-stimulated BM-derived neutrophils, as described previously (4). The cell compartment of the dual-beam spectrophotometer is kept at 37° C. with a circulating water system. Cuvettes of 0.5-ml capacity quartz cells and with black masked sides are used (Spectrocell, Inc., Oreland, Pa.). The sample cuvette contains 0.1 mM ferricytochrome C in PiCM buffer (138 mM NaCl, 2.7 mM KCl, 0.6 mM $CaCl_2$, 1.0 mM $MgCl_2$, 10 mM phosphate buffer, pH 7.4), isolated cells, electron donor (NADPH), and activating agent (PMA) in a total volume of 0.5 ml. The reference cuvette contains the same reagents plus 62.5 μg/ml of superoxide dismutase. After initiation of the reaction with PMA, the net increase in absorbance at 550 nm (sample minus reference) is followed for several minutes. The rate of superoxide production is calculated based on a specific extinction coefficient for ferrocytochrome C of 21.1/mM/cm (38).

Isolation of neutrophil-enriched BM cells and peritoneal exudate macrophages. BM cells are flushed from hind limbs and neutrophil-enriched fractions obtained essentially as described previously (25) by either isolating the nonadherent cell population (approximately 50% to 60% mature neutrophils as determined by examination of Wright's-stained cytospin preparations) or by discontinuous Percoll density gradient centrifugation (70% to 90% mature neutrophils). Neutrophil-enriched preparations are maintained on ice in 1×Hanks' balanced salt solution (HBSS) without Ca2+ or Mg2+ with 1% glucose and 0.1% BSA until further processing for NADPH oxidase assay and/or extraction of protein, RNA, or DNA.

For isolation of peritoneal exudate macrophages, mice are injected with aged thioglycollate broth by intraperitoneal injection, and 72 hours later, exudate cells (approximately 90% macrophages) are isolated by peritoneal lavage as previously described (25). Cells are incubated on ice as described above for neutrophil-enrichment before assay for NADPH oxidase activity and for RNA extraction.

Isolation of T and B cells. To demonstrate the myeloid specificity of the promoters further, lymphocytes are analyzed for lack of expression. Spleens are disaggregated to obtain a single cell suspension, and low-density mononuclear cells are isolated by centrifugation on Ficoll 1119. Cells are labeled with biotin-conjugated anti-mouse CD3 or CD45R/B220 monoclonal antibodies (PharMingen, San Diego, Calif.) for purification of T- and B-cell fractions respectively, using the MiniMACS (Miltenyi Biotec, Auburn, Calif.) magnetic cell separation system according to the manufacturer's instructions. Extracts for protein, RNA, and/or DNA are prepared as described below. Analysis of immunoselected cells by staining and flow cytometry shows greater than 98% purity. In some cases, total thymus is also extracted for protein and/or nucleic acids analysis (25, 32).

PB counts. To examine whether hematopoiesis is altered by the proposed manipulation, PB counts (hematocrit, white blood cell, differential, and reticulocyte counts) are determined at various times post-transplant using blood obtained from the tail vein. In some cases, blood is obtained either from the retro-orbital plexus or from the inferior vena cava post-mortem for platelet counts (32).

RNA, and immunoblot analysis. These are done using similar procedures as described herein.

Real-time PCR analysis of proviral copy number. Vector copy number in mouse peripheral blood cells is determined by real-time quantitative TaqMan polymerase chain reaction (PCR) (PE Applied Biosystems, Foster City, Calif.). Primers and probes completely within the extended LTR lentivector sequence that can be used regardless of the transgene ($gp91^{phox}$ or $p47^{phox}$) are used herein. Forward primer, TGAAAGCGAAAGGGAAACCA (SEQ ID NO:2); 6FAM-labeled probe, AGCTCTCTCGACGCAGGACTC (SEQ ID NO:3); reverse primer, CCGTGCGCGCTTCAG (SEQ ID NO:4). In some cases, $gp91^{phox}$ cDNA will also be targeted: forward primer, GTCGAAATCTGCTGTCCTTCCT (SEQ ID NO:7); 6FAM-labeled probe, TTCCAGTGCGTGCTGCTCAACAAGA (SEQ ID NO:8); reverse primer, TTCGAAGACAACTGGACAGGAAT (SEQ ID NO:9). The following incubation periods are applied for all primer sets: 2 min at 50° C., 10 min at 95° C., 40 cycles of 15 sec at 95° C., and 60 sec at 60° C. Standard curves for the TaqMan PCR analyses are obtained by using vector single-copy clones of NIH 3T3 cells transduced with the lentiviral vector (42).

*Asperillus fumizatus* infection X-CGD mice have a marked impairment in host defense to the opportunistic fungus, *A fumigatus*. Although wild-type mice are resistant to respiratory challenge with millions of *A fumigatus conidia*, as few as 50 conidia always resulted in chronic and sometimes fatal bronchopneumonia in X-CGD mice. Mice are infected by intratracheal instillation of *A. fumigatus* conidia (spores) obtained from a clinical isolate (ATCC No. 90240; American Tissue Culture Center, Rockville, Md.), as previously described (28). The test doses are 150 or 500 conidia per animal. The number of conidia in the inoculum is confirmed by plate culture. The trachea is exposed in mice anesthetized with ketamine, acepromazine, and atropine and the inoculum is instilled through a 24G angiocath (Becton Dickinson Vascular Access, Sandy, Utah) in 35 µL of sterile saline containing 5% colloidal carbon (Eberhard Faber, Inc, Lewisburg, Tenn.) to allow localization of the inoculum to each lung. As prophylaxis against secondary bacterial infection, mice are given an intramuscular injection of Ceftriaxone (Rocephin; Hoffman-La Roche, Nutley, N.J.), 1.25 mg per animal, immediately before infection, and again 24 hours later, followed by oral Tetracycline (Polyotic; American Cyanamid Co, Wayne, N.J.), 5 mg/ml, in the drinking water for the remainder of the experiment. Mice are examined daily, and electively killed by cervical dislocation 17 to 21 days after challenge with *A. fumigatus*. Lungs are removed and inflated and fixed in neutral buffered formalin for histologic examination of paraffin-embedded sections obtained from carbon-stained regions of lung. Sections are stained with hematoxylin and eosin for assessment of pathological changes or Grocott methamine silver for assessment of hyphae. Findings used to score for *A. fumigatus* lung disease, based on previous studies in murine X-CGD,31,32 include areas of purulent bronchopneumonia, granulomas with mixed inflammatory cell infiltrate, and presence of hyphae or abscesses.

Burkholderia cepacia infection B cepacia is an opportunistic gram-negative pathogen that can produce serious infections in patients with CGD, including pneumonia and associated sepsis. In a report on a national registry of 368 CGD patients, *B. cepacia* sepsis/pneumonia was the second most lethal infection on patients. Mice are injected intraperitoneally with a 0.5 ml saline suspension containing various numbers of *B. cepacia* bacilli (clinical isolate from bronchial washings; ATCC No. 25609; ATCC) at 12 to 14 weeks post-transplantation. Animals are monitored daily and killed if moribund. Tail venisection is performed to determine bacteremia for 7 to 8 days after challenge with $10^6$ colony-forming unit (CFU) or greater per mouse and for 15 to 17 days after challenge with $10^5$ CFU or less per mouse. Bacteremia is quantitated by plate culture. Blood is diluted in sterile water at 1:10 to lyse blood cells; further 10-fold serial dilutions of the lysed blood are plated in semi-soft agar (Becton Dickinson, Cockeysville, Md.) and colonies enumerated 48 hours after incubation at 37° C. (28).

*Staphylococcus aureus* infection *S aureus* is a common cause of soft tissue or visceral abscesses in CGD patients. Clearance of *S aureus* from the peritoneal cavity is impaired in X-CGD mice compared with wild-type mice after intraperitoneal injection of a sublethal dose of *S aureus*. Mice are injected intraperitoneally with a 0.2 ml suspension of $1\times10^8$/ml *S. aureus* strain 502A (ATCC No. 27217; ATCC), as previously described (28). The number of bacteria in the inoculum is confirmed by plate culture of serial dilutions. Mice are examined daily and killed 7 days after peritoneal challenge. The presence of staphylococcal intraperitoneal abscesses is assessed by visual inspection, and the organism is confirmed by culture and Gram stain.

Safety testing. Because the $gp91^{phox}$-deficient mice have a protein null phenotype of X-CGD and human $gp91^{phox}$ is expressed as transgene, mouse serum are tested for the development of antibody specific to human $gp91^{phox}$ by SDS/PAGE and immunoblot detection. Genomic DNA from peripheral blood cells is screened for the presence of replication competent retrovirus by using a PCR assay to detect sequence encoding the envelope (30, 31, 42).

Correction of $p47^{phox}$-deficiency by bone marrow transplantation combined with ex vivo lentiviral transduction of SP-$p47^{phox}$ gene Animals. $p47^{phox}$–/– mice are provided by Dr. Steven Holland at NIH. Gene deletants were created in the 129 background strain and bred on C57BL/6 as described. Heterozygous deletants were crossed back onto the C57BL/6 background and then intercrossed (67). $p47^{phox}$–/– mice and wild-type littermates are used for the described experiments. Genotyping of mice is performed using polymerase chain reaction of tail blood and confirmed by NBT testing of peripheral blood neutrophils. Mice are maintained under specific pathogen-free conditions and fed autoclaved food and acidified water. In addition, all $p47^{phox}$–/– mice are maintained on *Bactrim prophylaxis* (30 mg/kg), except during and after bacterial challenge studies.

Other procedures. Lentivector construction, viral production, transduction of HSC, bone marrow transplantation, assessment of NADPH oxidase reconstitution and host defense are done as described herein.

Statistical analysis. ANOVA is used to examine any statistical difference among groups, followed by Newman-Keuls comparison or Bonferroni comparison analysis. For the infection challenge studies, statistical analysis using the Fischer exact test or the Mann-Whitney nonparametric test with 2-tailed P values is performed by using Instat 2.0 software. Log rank-tests for equality of survival are performed using GB-Stat version 6.5 software (Dynamic Microsystems, Silver Spring, Md.) (28).

REFERENCE FOR EXAMPLE 4

1. Clark, R. A. The human neutrophil respiratory burst oxidase. J Infect Dis, 161: 1140-1147., 1990.
2. Segal, B. H., Leto, T. L., Gallin, J. I., Malech, H. L., and Holland, S. M. Genetic, biochemical, and clinical features of chronic granulomatous disease. Medicine (Baltimore), 79: 170-200., 2000.
3. Goldblatt, D. and Thrasher, A. J. Chronic granulomatous disease. Clin Exp Immunol, 122: 1-9., 2000.
4. Clark, R. A., Leidal, K. G., Pearson, D. W., and Nauseef, W. M. NADPH oxidase of human neutrophils. Subcellular localization and characterization of an arachidonate-activatable superoxide-generating system. J Biol Chem, 262: 4065-4074., 1987.
5. Horwitz, M. E., Barrett, A. J., Brown, M. R., Carter, C. S., Childs, R., Gallin, J. I., Holland, S. M., Linton, G. F., Miller, J. A., Leitman, S. F., Read, E. J., and Malech, H. L. Treatment of chronic granulomatous disease with nonmyeloablative conditioning and a T-cell-depleted hematopoietic allograft. N Engi J Med, 344: 881-888, 2001.
6. Seger, R. A., Gungor, T., Belohradsky, B. H., Blanche, S., Bordigoni, P., Di Bartolomeo, P., Flood, T., Landais, P., Muller, S., Ozsahin, H., Passwell, J. H., Porta, F., Slavin, S., Wulffraat, N., Zintl, F., Nagler, A., Cant, A., and Fischer, A. Treatment of chronic granulomatous disease with myeloablative conditioning and an unmodified hematopoietic allograft: a survey of the European experience, 1985-2000. Blood, 100: 4344-4350., 2002.
7. Lakshman, R. and Finn, A. Neutrophil disorders and their management. J Clin Pathol, 54: 7-19., 2001.
8. Lekstrom-Himes, J. A. and Gallin, J. I. Immunodeficiency diseases caused by defects in phagocytes. N Engl J Med, 343: 1703-1714., 2000.
9. Suzuki, S., Kumatori, A., Haagen, I. A., Fujii, Y., Sadat, M. A., Jun, H. L., Tsuji, Y., Roos, D., and Nakamura, M. PU.1 as an essential activator for the expression of gp91(phox) gene in human peripheral neutrophils, monocytes, and B lymphocytes. Proc Natl Acad Sci USA, 95: 6085-6090., 1998.
10. Li, S. L., Valente, A. J., Zhao, S. J., and Clark, R. A. PU.1 is essential for p47(phox) promoter activity in myeloid cells. J Biol Chem, 272: 17802-17809., 1997.
11. Li, S. L., Schlegel, W., Valente, A. J., and Clark, R. A. Critical flanking sequences of PU.1 binding sites in myeloid-specific promoters. J Biol Chem, 274: 32453-32460., 1999.
12. Li, S. L., Valente, A. J., Wang, L., Gamez, M. J., and Clark, R. A. Transcriptional regulation of the p67phox gene: role of AP-1 in concert with myeloid-specific transcription factors. J Biol Chem, 276: 39368-39378., 2001.
13. Li, S. L., Valente, A. J., Qiang, M., Schlegel, W., Gamez, M., and Clark, R. A. Multiple PU.1 sites cooperate in the regulation of p40(phox) transcription during granulocytic differentiation of myeloid cells. Blood, 99: 4578-4587, 2002.
14. Cheng, G., Cao, Z., Xu, X., van Meir, E. G., and Lambeth, J. D. Homologs of gp91phox: cloning and tissue expression of Nox3, Nox4, and Nox5. Gene, 269: 131-140., 2001.
15. Arnold, R. S., Shi, J., Murad, E., Whalen, A. M., Sun, C. Q., Polavarapu, R., Parthasarathy, S., Petros, J. A., and Lambeth, J. D. Hydrogen peroxide mediates the cell growth and transformation caused by the mitogenic oxidase Nox1. Proc Natl Acad Sci USA, 98: 5550-5555., 2001.
16. Suh, Y. A., Arnold, R. S., Lassegue, B., Shi, J., Xu, X., Sorescu, D., Chung, A. B., Griendling, K. K., and Lambeth, J. D. Cell transformation by the superoxide-generating oxidase Mox1. Nature, 401: 79-82., 1999.
17. Banfi, B., Maturana, A., Jaconi, S., Arnaudeau, S., Laforge, T., Sinha, B., Ligeti, E., Demaurex, N., and Krause, K. H. A mammalian H+ channel generated through alternative splicing of the NADPH oxidase homolog NOH-1. Science, 287: 138-142., 2000.
18. Banfi, B., Clark, R. A., Steger, K., and Krause, K. H. Two novel proteins activate superoxide generation by the NADPH oxidase NOX1. J Biol Chem, 278: 3510-3513, 2003.
19. Geiszt, M., Lekstrom, K., Witta, J., and Leto, T. L. Proteins Homologous to p47phox and p67phox Support Superoxide Production by NAD(P)H Oxidase 1 in Colon Epithelial Cells. J Biol Chem, 278: 20006-20012., 2003.
20. Takeya, R., Ueno, N., Kami, K., Taura, M., Kohjima, M., Izaki, T., Nunoi, H., and Sumimoto, H. Novel human homologues of p47phox and p67phox participate in activation of superoxide-producing NADPH oxidases. J Biol Chem, 25: 25, 2003.
21. Malech, H. L. Progress in gene therapy for chronic granulomatous disease. J Infect Dis, 179 Suppl 2: S318-325., 1999.
22. Kume, A. and Dinauer, M. C. Gene therapy for chronic granulomatous disease. J Lab Clin Med, 135: 122-128., 2000.
23. Winkelstein, J. A., Marino, M. C., Johnston, R. B., Jr., Boyle, J., Curnutte, J., Gallin, J. I., Malech, H. L., Holland, S. M., Ochs, H., Quie, P., Buckley, R. H., Foster, C. B., Chanock, S. J., and Dickler, H. Chronic granulomatous disease. Report on a national registry of 368 patients. Medicine (Baltimore), 79: 155-169., 2000.
24. Malech, H. L., Maples, P. B., Whiting-Theobald, N., Linton, G. F., Sekhsaria, S., Vowells, S. J., Li, F., Miller, J. A., DeCarlo, E., Holland, S. M., Leitman, S. F., Carter, C. S., Butz, R. E., Read, E. J., Fleisher, T. A., Schneiderman, R. D., Van Epps, D. E., Spratt, S. K., Maack, C. A., Rokovich, J. A., Cohen, L. K., and Gallin, J. I. Prolonged production of NADPH oxidase-corrected granulocytes after gene therapy of chronic granulomatous disease. Proc Natl Acad Sci USA, 94: 12133-12138., 1997.
25. Dinauer, M. C., Li, L. L., Bjorgvinsdottir, H., Ding, C., and Pech, N. Long-term correction of phagocyte NADPH oxidase activity by retroviral-mediated gene transfer in murine X-linked chronic granulomatous disease. Blood, 94: 914-922., 1999.
26. May, C., Rivella, S., Callegari, J., Heller, G., Gaensler, K. M., Luzzatto, L., and Sadelain, M. Therapeutic haemoglobin synthesis in beta-thalassaemic mice expressing lentivirus-encoded human beta-globin. Nature, 406: 82-86., 2000.
27. Rex, J. H., Bennett, J. E., Gallin, J. I., Malech, H. L., and Melnick, D. A. Normal and deficient neutrophils can cooperate to damage Aspergillus fumigatus hyphae. J Infect Dis, 162: 523-528., 1990.

28. Dinauer, M. C., Gifford, M. A., Pech, N., Li, L. L., and Emshwiller, P. Variable correction of host defense following gene transfer and bone marrow transplantation in murine X-linked chronic granulomatous disease. Blood, 97: 3738-3745., 2001.

29. Goebel, W. S. and Dinauer, M. C. Retroviral-mediated gene transfer and nonmyeloablative conditioning: studies in a murine X-linked chronic granulomatous disease model. J Pediatr Hematol Oncol, 24: 787-790., 2002.

30. Brenner, S. and Malech, H. L. Current developments in the design of onco-retrovirus and lentivirus vector systems for hematopoietic cell gene therapy. Biochim Biophys Acta, 1640: 1-24., 2003.

31. Galimi, F. and Verma, I. M. Opportunities for the use of lentiviral vectors in human gene therapy. Curr Top Microbiol Immunol, 261: 245-254, 2002.

32. Bjorgvinsdottir, H., Ding, C., Pech, N., Gifford, M. A., Li, L. L., and Dinauer, M. C. Retroviral-mediated gene transfer of gp91phox into bone marrow cells rescues defect in host defense against Aspergillus fumigatus in murine X-linked chronic granulomatous disease. Blood, 89: 41-48., 1997.

33. Miyoshi, H., Blomer, U., Takahashi, M., Gage, F. H., and Verma, I. M. Development of a self-inactivating lentivirus vector. J Virol, 72: 8150-8157., 1998.

34. Naldini, L. In vivo gene delivery by lentiviral vectors. Thromb Haemost, 82: 552-554., 1999.

35. Pan, D., Gunther, R., Duan, W., Wendell, S., Kaemmerer, W., Kafri, T., Verma, I. M., and Whitley, C. B. Biodistribution and toxicity studies of VSVG-pseudotyped lentiviral vector after intravenous administration in mice with the observation of in vivo transduction of bone marrow. Mol Ther, 6: 19-29., 2002.

36. Yam, P. Y., Li, S., Wu, J., Hu, J., Zaia, J. A., and Yee, J. K. Design of HIV vectors for efficient gene delivery into human hematopoietic cells. Mol Ther, 5: 479-484., 2002.

37. Kootstra, N. A. and Verma, I. M. Gene therapy with viral vectors. Annu Rev Pharmacol Toxicol, 43: 413-439, 2003.

38. Pawliuk, R., Westerman, K. A., Fabry, M. E., Payen, E., Tighe, R., Bouhassira, E. E., Acharya, S. A., Ellis, J., London, I. M., Eaves, C. J., Humphries, R. K., Beuzard, Y., Nagel, R. L., and Leboulch, P. Correction of sickle cell disease in transgenic mouse models by gene therapy. Science, 294: 2368-2371., 2001.

39. Woods, N. B., Ooka, A., and Karlsson, S. Development of gene therapy for hematopoietic stem cells using lentiviral vectors. Leukemia, 16: 563-569., 2002.

40. Kondo, M., Wagers, A. J., Manz, M. G., Prohaska, S. S., Scherer, D. C., Beilhack, G. F., Shizuru, J. A., and Weissman, I. L. BIOLOGY OF HEMATOPOIETIC STEM CELLS AND PROGENITORS: Implications for Clinical Application. Annu Rev Immunol, 21: 759-806, 2003.

41. Imren, S., Payen, E., Westerman, K. A., Pawliuk, R., Fabry, M. E., Eaves, C. J., Cavilla, B., Wadsworth, L. D., Beuzard, Y., Bouhassira, E. E., Russell, R., London, I. M., Nagel, R. L., Leboulch, P., and Humphries, R. K. Permanent and panerythroid correction of murine beta thalassemia by multiple lentiviral integration in hematopoietic stem cells. Proc Natl Acad Sci U S A, 99: 14380-14385., 2002.

42. Roesler, J., Brenner, S., Bukovsky, A. A., Whiting-Theobald, N., Dull, T., Kelly, M., Civin, C. I., and Malech, H. L. Third-generation, self-inactivating gp91(phox) lentivector corrects the oxidase defect in NOD/SCID mouse-repopulating peripheral blood-mobilized CD34+ cells from patients with X-linked chronic granulomatous disease. Blood, 100: 4381-4390., 2002.

43. Sclimenti, C. R., Baba, E. J., and Calos, M. P. An extrachromosomal tetracycline-regulatable system for mammalian cells. Nucleic Acids Res, 28: E80., 2000.

44. Vigna, E., Cavalieri, S., Ailles, L., Geuna, M., Loew, R., Bujard, H., and Naldini, L. Robust and efficient regulation of transgene expression in vivo by improved tetracycline-dependent lentiviral vectors. Mol Ther, 5: 252-261., 2002.

45. Li, X., Eastman, E. M., Schwartz, R. J., and Draghia-Akli, R. Synthetic muscle promoters: activities exceeding naturally occurring regulatory sequences. Nat Biotechnol, 17: 241-245., 1999.

46. Clarke, S. and Gordon, S. Myeloid-specific gene expression. J Leukoc Biol, 63: 153-168., 1998.

47. Ward, A. C., Loeb, D. M., Soede-Bobok, A. A., Touw, I. P., and Friedman, A. D. Regulation of granulopoiesis by transcription factors and cytokine signals. Leukemia, 14: 973-990., 2000.

48. Shivdasani, R. A. and Orkin, S. H. The transcriptional control of hematopoiesis. Blood, 87: 4025-4039., 1996.

49. Tenen, D. G., Hromas, R., Licht, J. D., and Zhang, D. E. Transcription factors, normal myeloid development, and leukemia. Blood, 90: 489-519., 1997.

50. Roberts, W. M., Shapiro, L. H., Ashmun, R. A., and Look, A. T. Transcription of the human colony-stimulating factor-1 receptor gene is regulated by separate tissue-specific promoters. Blood, 79: 586-593., 1992.

51. Dziennis, S., Van Etten, R. A., Pahl, H. L., Morris, D. L., Rothstein, T. L., Blosch, C. M., Perlmutter, R. M., and Tenen, D. G. The CD11b promoter directs high-level expression of reporter genes in macrophages in transgenic mice. Blood, 85: 319-329., 1995.

52. Persons, D. A. and Nienhuis, A. W. Gene therapy for the hemoglobin disorders: past, present, and future. Proc Natl Acad Sci U S A, 97: 5022-5024., 2000.

53. Malik, P., Krall, W. J., Yu, X. J., Zhou, C., and Kohn, D. B. Retroviral-mediated gene expression in human myelomonocytic cells: a comparison of hematopoietic cell promoters to viral promoters. Blood, 86: 2993-3005., 1995.

54. Jiang, Y., Jahagirdar, B. N., Reinhardt, R. L., Schwartz, R. E., Keene, C. D., Ortiz-Gonzalez, X. R., Reyes, M., Lenvik, T., Lund, T., Blackstad, M., Du, J., Aldrich, S., Lisberg, A., Low, W. C., Largaespada, D. A., and Verfaillie, C. M. Pluripotency of mesenchymal stem cells derived from adult marrow. Nature, 418: 41-49., 2002.

55. Hubner, K., Fuhrmann, G., Christenson, L. K., Kehler, J., Reinbold, R., De La Fuente, R., Wood, J., Strauss, J. F., 3rd, Boiani, M., and Scholer, H. R. Derivation of oocytes from mouse embryonic stem cells. Science, 300: 1251-1256., 2003.

56. Horwitz, E. M., Gordon, P. L., Koo, W. K., Marx, J. C., Neel, M. D., McNall, R. Y., Muul, L., and Hofmann, T. Isolated allogeneic bone marrow-derived mesenchymal cells engraft and stimulate growth in children with osteogenesis imperfecta: Implications for cell therapy of bone. Proc Natl Acad Sci USA, 99: 8932-8937., 2002.

57. Shariatmadari, R., Sipila, P. P., Huhtaniemi, I. T., and Poutanen, M. Improved technique for detection of enhanced green fluorescent protein in transgenic mice. Biotechniques, 30: 1282-1285., 2001.

58. Recillas-Targa, F., Bell, A. C., and Felsenfeld, G. Positional enhancer-blocking activity of the chicken beta-globin insulator in transiently transfected cells. Proc Natl Acad Sci USA, 96: 14354-14359., 1999.

59. Mardiney, M., 3rd, Jackson, S. H., Spratt, S. K., Li, F., Holland, S. M., and Malech, H. L. Enhanced host defense after gene transfer in the murine p47phox- deficient model of chronic granulomatous disease. Blood, 89: 2268-2275., 1997.
60. Rhoades, K. L., Hetherington, C. J., Harakawa, N., Yergeau, D. A., Zhou, L., Liu, L. Q., Little, M. T., Tenen, D. G., and Zhang, D. E. Analysis of the role of AML1-ETO in leukemogenesis, using an inducible transgenic mouse model. Blood, 96: 2108-2115., 2000.
61. Fedorov, L. M., Tyrsin, O. Y., Sakk, O., Ganscher, A., and Rapp, U. R. Generation dependent reduction of tTA expression in double transgenic NZL-2/tTA(CMV) mice. Genesis, 31: 78-84., 2001.
62. Hahn, C. N., del Pilar Martin, M., Zhou, X. Y., Mann, L. W., and d'Azzo, A. Correction of murine galactosialidosis by bone marrow-derived macrophages overexpressing human protective protein/cathepsin A under control of the colony-stimulating factor-1 receptor promoter. Proc Nati Acad Sci U S A, 95: 14880-14885., 1998.
63. Back, A., East, K., and Hickstein, D. Leukocyte integrin CD11b promoter directs expression in lymphocytes and granulocytes in transgenic mice. Blood, 85: 1017-1024., 1995.
64. Blum, M. A null mutation in TGF-alpha leads to a reduction in midbrain dopaminergic neurons in the substantia nigra. Nat Neurosci, 1: 374-377., 1998.
65. Ho, A. and Blum, M. Induction of interleukin-1 associated with compensatory dopaminergic sprouting in the denervated striatum of young mice: model of aging and neurodegenerative disease. J Neurosci, 18: 5614-5629., 1998.
66. Vowells, S. J., Sekhsaria, S., Malech, H. L., Shalit, M., and Fleisher, T. A. Flow cytometric analysis of the granulocyte respiratory burst: a comparison study of fluorescent probes. J Immunol Methods, 178: 89-97., 1995.
67. Jackson, S. H., Gallin, J. I., and Holland, S. M. The p47phox mouse knock-out model of chronic granulomatous disease. J Exp Med, 182: 751-758., 1995.

Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference into this application in order to more fully describe the state of the art to which this invention pertains.

TABLE 1

FACS analysis of EGFP Expression in Liver Cells of Mice Injected with the Indicated DNA(%)

| Plasmid | GFP(+)/CD11b(+) | GFP(+)/CD11b(−) |
|---|---|---|
| none | 0 | 0 |
| pEGFPC1 | 16.48 ± 4.22 | 13.20 ± 5.64 |
| pEGFPC1-SP-144 | 15.94 ± 4.79 | 2.34 ± 1.90 |

Mouse-tail vein injections were carried out using the TransIT in vivo gene delivery system (Mirus, Cat# MIR 5125). pEGFPC1 is an EGFP-fusion protein expression/reporter vector from Clontech. CMV promoter is used in this vector. In construct pEGFPC1-SP-144, CMV was replaced by a synthetic macrophage promoter. Data shown are means (±S.E.) of three experiments.

TABLE 2

| Group | Donor mice | Lentiviral vector transduction of HSC | Recipient mice |
|---|---|---|---|
| A | ApoE−/− | CMV-ApoE3 | ApoE−/− |
| B | ApoE−/− | SMP-146-ApoE3 | ApoE−/− |
| C | ApoE−/− | SMP-146-GFP | ApoE−/− |
| D | ApoE−/− | None (Self control) | ApoE−/− |
| E | C57BL/6 | None (WT control) | ApoE−/− |

TABLE 3

| | | |
|---|---|---|
| 5'-CTGGAAAGAGGAAGTCGCTT-3' | PU.1A (p47phox) | SEQ ID NO:10 |
| 5'-CAGAAAAGGAGAAGTAGGAG-3' | PU.1B (CD11b) | SEQ ID NO:11 |
| 5'-CCAAGATTTCCAAACTCTGTGGTTGCCTTG-3' | C/EBPα + AML1 (CSF-1R) | SEQ ID NO:12 |
| 5'-GGGTTATGAGTCAGTTGCCA-3' | AP1 (p67phox) | SEQ ID NO:13 |
| 5'-CTGAGCCTCCGCCCTCTTCCT-3' | Sp1 (CD11b) | SEQ ID NO:14 |
| 5'-GTCCGCCCTCGCTAGCGTCCGCCCTC-3' | NheI-linker | SEQ ID NO:15 |
| 5'-TGAGCCTCCGCCCTCTTCCT-3' | Sp1 (CD11b) | SEQ ID NO:27 |
| 5'-AAGCGACTTCCTCTTTCCAG-3' | PU.1A | SEQ ID NO:25 |
| 5'-CTCCTACTTCTCCTTTTCTG-3' | PU.1B | SEQ ID NO:26 |

What is claimed is:

1. An isolated nucleic acid comprising a promoter operably linked to a nucleic acid encoding a peptide or protein of interest, wherein the promoter comprises the following elements, in order: [C/EBPα forward]-[AM L-1 forward]-[PU.1A reverse]-[PU.1B reverse]-[PU.1A reverse]-[AM L-1 reverse]-[C/EBPα reverse]-[C/EBPα forward]-[AM L-1 forward] [PU.1B reverse] [PU.1A forward]-[Sp1 forward]-[Sp1 forward][C/EBPα forward]-[AM L-1 forward].

2. An isolated nucleic acid comprising a promoter operably linked to a nucleic acid encoding a peptide or protein of interest, wherein the promoter comprises the following elements, in order: [PU.1B reverse]-[C/EBPα forward]-[AM L-1 forward]-[C/EBPα forward]-[AM L-1 forward]-[PU.1B reverse]-[PU.1A forward]-[PU.1A forward]-[Sp1 reverse]-[AM L-1 reverse]-[C/EBPα reverse]-[PU.1A forward]-[PU.1B reverse]-[PU.1A forward].

3. The nucleic acid of claim 1, wherein the peptide or protein of interest is a therapeutic peptide or protein.

4. The nucleic acid of claim 3, wherein the peptide or protein is selected from the group consisting of: glial cell-derived neurotrophic factor (GDNF), nerve growth factor (NGF), brain-derived neurotrophic factor (BDNF), ciliary neurotrophic factor (CNTF), neprilysin, lysosomal protective protein 1 cathepsin A (PPCA), insulin-like growth factor (IGF-1), glucocerebrosidase, liver X receptors, apoE, apoA1, ATP-binding cassette transporter A1 (ABCA1), $gp91^{phox}$, $p47^{phox}$, $p67^{phox}$ and $p22^{phox}$.

5. A vector comprising the nucleic acid of claim 1.

6. A cell comprising the vector of claim 5.

7. An isolated nucleic acid comprising a promoter operably linked to a nucleic acid encoding a peptide or protein of interest, wherein the promoter comprises a nucleotide sequence selected from the group consisting of the nucleotide sequence of SEQ ID NO:18 and the nucleotide sequence of SEQ ID NO:19.

8. A method of expressing a nucleic acid encoding a peptide or protein of interest in a myeloid cell, comprising introducing into the myeloid cell the nucleic acid of claim 1.

9. The nucleic acid of claim 2, wherein the peptide or protein of interest is a therapeutic peptide or protein.

10. The nucleic acid of claim 9, wherein the peptide or protein is selected from the group consisting of: glial cell-derived neurotrophic factor (GDNF), nerve growth factor (NGF), brain-derived neurotrophic factor (BDNF), ciliary neurotrophic factor (CNTF), neprilysin, lysosomal protective protein 1 cathepsin A (PPCA), insulin-like growth factor (IGF-1), glucocerebrosidase, liver X receptors, apoE, apoA1, ATP-binding cassette transporter A1 (ABCA 1), $gp91^{phox}$, $p47^{phox}$, $p67^{phox}$ and $p22^{phox}$.

11. A vector comprising the nucleic acid of claim 2.

12. A cell comprising the vector of claim 11.

13. A method of expressing a nucleic acid encoding a peptide or protein of interest in a myeloid cell, comprising introducing into the myeloid cell the nucleic acid of claim 2.

14. The nucleic acid of claim 7, wherein the peptide or protein of interest is a therapeutic peptide or protein.

15. The nucleic acid of claim 14, wherein the peptide or protein is selected from the group consisting of: glial cell-derived neurotrophic factor (GDNF), nerve growth factor (NGF), brain-derived neurotrophic factor (BDNF), ciliary neurotrophic factor (CNTF), neprilysin, lysosomal protective protein 1 cathepsin A (PPCA), insulin-like growth factor (IGF-1), glucocerebrosidase, liver X receptors, apoE, apoA1, ATP-binding cassette transporter A1 (ABCA1), $gp91^{phox}$, $p47^{phox}$, $p67^{phox}$ and $p22^{phox}$.

16. A vector comprising the nucleic acid of claim 7.

17. A cell comprising the vector of claim 16.

18. A method of expressing a nucleic acid encoding a peptide or protein of interest in a myeloid cell, comprising introducing into the myeloid cell the nucleic acid of claim 7.

19. A hematopoietic stem cell comprising the vector of claim 5.

20. A hematopoietic stem cell comprising the vector of claim 11.

21. A hematopoietic stem cell comprising the vector of claim 16.

* * * * *

UNITED STATES PATENT AND TRADEMARK OFFICE
CERTIFICATE OF CORRECTION

PATENT NO. : 7,709,625 B2  
APPLICATION NO. : 11/199465  
DATED : May 4, 2010  
INVENTOR(S) : Li et al.

It is certified that error appears in the above-identified patent and that said Letters Patent is hereby corrected as shown below:

In the Specification:

Column 52, Line 27: Please correct "LXR ligand7" to read -- LXR ligand$^{17}$ --

Line 53: Please correct "hypertriglyceridemial$^{6;21;22}$" to read -- hypertriglyceridemial$^{16;21;22}$ --

Signed and Sealed this  
Twenty-second Day of March, 2011

David J. Kappos  
*Director of the United States Patent and Trademark Office*

UNITED STATES PATENT AND TRADEMARK OFFICE
CERTIFICATE OF CORRECTION

Page 1 of 1

PATENT NO. : 7,709,625 B2
APPLICATION NO. : 11/199465
DATED : May 4, 2010
INVENTOR(S) : Li et al.

It is certified that error appears in the above-identified patent and that said Letters Patent is hereby corrected as shown below:

In the Specification:

Column 52, Line 27: Please correct "LXR ligand7" to read -- LXR ligand$^{17}$ --

Line 53: Please correct "hypertriglyceridemia1$^{6;21;22}$"
to read -- hypertriglyceridemia$^{16;21;22}$ --

This certificate supersedes the Certificate of Correction issued March 22, 2011.

Signed and Sealed this
Seventeenth Day of May, 2011

David J. Kappos
*Director of the United States Patent and Trademark Office*

SEQUENCE LISTING

<160> NUMBER OF SEQ ID NOS: 27

<210> SEQ ID NO 1
<211> LENGTH: 8
<212> TYPE: PRT
<213> ORGANISM: Artificial
<220> FEATURE:
<223> OTHER INFORMATION: Flag sequence

<400> SEQUENCE: 1

Asp Tyr Lys Asp Asp Asp Asp Lys
1               5

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
tgaaagcgaa agggaaacca                                               20

<210> SEQ ID NO 3
<211> LENGTH: 21
<212> TYPE: DNA
<213> ORGANISM: Artificial
<220> FEATURE:
<223> OTHER INFORMATION: Probe sequence

<400> SEQUENCE: 3
agctctctcg acgcaggact c                                             21

<210> SEQ ID NO 4
<211> LENGTH: 15
<212> TYPE: DNA
<213> ORGANISM: Artificial
<220> FEATURE:
<223> OTHER INFORMATION: Primer

<400> SEQUENCE: 4
ccgtgcgcgc ttcag                                                    15

<210> SEQ ID NO 5
<211> LENGTH: 25
<212> TYPE: DNA
<213> ORGANISM: Artificial
<220> FEATURE:
<223> OTHER INFORMATION: Primer

<400> SEQUENCE: 5
cctccaccaa attcatccgg aggtc                                         25

<210> SEQ ID NO 6
<211> LENGTH: 25
<212> TYPE: DNA
<213> ORGANISM: Artificial
<220> FEATURE:
<223> OTHER INFORMATION: Primer

<400> SEQUENCE: 6
gacctccgga tgaatttggt ggagg                                         25

<210> SEQ ID NO 7

-continued

```
<211> LENGTH: 22
<212> TYPE: DNA
<213> ORGANISM: Artificial
<220> FEATURE:
<223> OTHER INFORMATION: Primer

<400> SEQUENCE: 7
gtcgaaatct gctgtccttc ct                                              22

<210> SEQ ID NO 8
<211> LENGTH: 25
<212> TYPE: DNA
<213> ORGANISM: Artificial
<220> FEATURE:
<223> OTHER INFORMATION: Probe sequence

<400> SEQUENCE: 8
ttccagtgcg tgctgctcaa caaga                                           25

<210> SEQ ID NO 9
<211> LENGTH: 23
<212> TYPE: DNA
<213> ORGANISM: Artificial
<220> FEATURE:
<223> OTHER INFORMATION: Primer

<400> SEQUENCE: 9
ttcgaagaca actggacagg aat                                             23

<210> SEQ ID NO 10
<211> LENGTH: 20
<212> TYPE: DNA
<213> ORGANISM: Artificial
<220> FEATURE:
<223> OTHER INFORMATION: Synthetic oligonucleotide

<400> SEQUENCE: 10
ctggaaagag gaagtcgctt                                                 20

<210> SEQ ID NO 11
<211> LENGTH: 20
<212> TYPE: DNA
<213> ORGANISM: Artificial
<220> FEATURE:
<223> OTHER INFORMATION: Synthetic oligonucleotide

<400> SEQUENCE: 11
cagaaaagga gaagtaggag                                                 20

<210> SEQ ID NO 12
<211> LENGTH: 30
<212> TYPE: DNA
<213> ORGANISM: Artificial
<220> FEATURE:
<223> OTHER INFORMATION: Synthetic oligonucleotide

<400> SEQUENCE: 12
ccaagatttc caaactctgt ggttgccttg                                      30

<210> SEQ ID NO 13
<211> LENGTH: 21
<212> TYPE: DNA
<213> ORGANISM: Artificial
<220> FEATURE:
<223> OTHER INFORMATION: Synthetic oligonucleotide

<400> SEQUENCE: 13
```

```
gggttatgag tcagttgccc a                                              21

<210> SEQ ID NO 14
<211> LENGTH: 21
<212> TYPE: DNA
<213> ORGANISM: Artificial
<220> FEATURE:
<223> OTHER INFORMATION: Synthetic oligonucleotide

<400> SEQUENCE: 14
ctgagcctcc gccctcttcc t                                              21

<210> SEQ ID NO 15
<211> LENGTH: 26
<212> TYPE: DNA
<213> ORGANISM: Artificial
<220> FEATURE:
<223> OTHER INFORMATION: Linker sequence

<400> SEQUENCE: 15
gtccgccctc gctagcgtcc gccctc                                         26

<210> SEQ ID NO 16
<211> LENGTH: 176
<212> TYPE: DNA
<213> ORGANISM: Artificial
<220> FEATURE:
<223> OTHER INFORMATION: SP-60 synthetic promoter

<400> SEQUENCE: 16
ctagcgtccg ccctcaggaa gagggcggag gctcaccaag atttccaaac tctgtggttg    60
ccttgccaag atttccaaac tctgtggttg ccttgccaag atttccaaac tctgtggttg   120
ccttgtgagc ctccgccctc ttcctaagcg acttcctctt tccaggaggg cggacg       176

<210> SEQ ID NO 17
<211> LENGTH: 266
<212> TYPE: DNA
<213> ORGANISM: Artificial
<220> FEATURE:
<223> OTHER INFORMATION: SP-107 synthetic promoter

<400> SEQUENCE: 17
ctagcgaggg cggacaagcg acttcctctt tccagcagaa aaggagaagt aggagccaag    60
atttccaaac tctgtggttg ccttgaagcg acttcctctt tccagaagcg acttcctctt   120
tccagcagaa aaggagaagt aggagctcct acttctcctt ttctgccaag atttccaaac   180
tctgtggttg ccttgctcct acttctcctt ttctgcagaa aaggagaagt aggagctgga   240
aagaggaagt cgcttgaggg cggacg                                        266

<210> SEQ ID NO 18
<211> LENGTH: 276
<212> TYPE: DNA
<213> ORGANISM: Artificial
<220> FEATURE:
<223> OTHER INFORMATION: SP-146 synthetic promoter

<400> SEQUENCE: 18
ctagcgaggg cggaccagaa aaggagaagt aggagccaag atttccaaac tctgtggttg    60
ccttgccaag atttccaaac tctgtggttg ccttgcagaa aaggagaagt aggagaagcg   120
acttcctctt tccagaagcg acttcctctt tccagaggaa gagggcggag gctcacaagg   180
```

```
caaccacaga gtttggaaat cttggaagcg acttcctctt tccagcagaa aaggagaagt    240
aggagaagcg acttcctctt tccaggtccg ccctcg                              276
```

<210> SEQ ID NO 19
<211> LENGTH: 260
<212> TYPE: DNA
<213> ORGANISM: Artificial
<220> FEATURE:
<223> OTHER INFORMATION: SP-30 synthetic promoter

<400> SEQUENCE: 19

```
ctagcgtccg ctcctcccaa gatttccaaa ctctgtggtt gccttgctgg aaagaggaag     60
tcgcttcaga aaaggagaag taggagctgg aaagaggaag tcgcttcaag gcaaccacag    120
agtttgaaat ttggccaaga tttccaaact ctggtctgtg cagaaaagga gaagtaggag    180
aagcgacttc ctctttcggt cccctcgcta gcgtccgccc tcccaagatt tccaaactct    240
gtggttgcct tggagggcgg                                                260
```

<210> SEQ ID NO 20
<211> LENGTH: 479
<212> TYPE: DNA
<213> ORGANISM: Artificial
<220> FEATURE:
<223> OTHER INFORMATION: SP-144 synthetic promoter
<220> FEATURE:
<221> NAME/KEY: misc_feature
<222> LOCATION: (471)..(471)
<223> OTHER INFORMATION: n is a, c, g, or t

<400> SEQUENCE: 20

```
ctagccgccc tccagaaaag gagaagtagg agtgagcctc cgccctcttc ctcaaggcaa     60
ccacagagtt tggaaatctt ggaagcgact tcctctttcc agcagaaaag gagaagtagg    120
aggggttatg agtcagttgc cactcctact tctcttttct aaggcaacca cagagtttgg    180
aaatcttgga gggcggactg gcaactgact cataacccca aggcaaccac agagtttgga    240
aatcttggaa gcgacttcct ctttccagga gagggcgga ggctcactcc tacttctcct    300
ttttctagag ccacagagtt tgaaaatctt ggctctctac ttctccttt ctcaagatct    360 ctgtggttgc cttgctccta cttctccttt tctggagggc ggaccctaga gggcggacca    420
aggcaaccac agagtttgga aatcttggct cctacttctc cttttctggt ncgccctcg    479
```

<210> SEQ ID NO 21
<211> LENGTH: 272
<212> TYPE: DNA
<213> ORGANISM: Artificial
<220> FEATURE:
<223> OTHER INFORMATION: Synthetic promoter

<400> SEQUENCE: 21

```
ctagcgtccg ccctcccaag atttccaaac tctgtggttg ccttgctgga aagaggaagt     60
cgcttcagaa aaggagaagt aggagctgga aagaggaagt cgcttcaagg caaccacaga    120
gtttggaaat cttggccaag atttccaaac tctgtggttg ccttgcagaa aaggagaagt    180
aggagaagcg acttcctctt tccaggtccg ccctcgctag cgtccgccct cccaagattt    240
ccaaactctg tggttgcctt ggagggcgga cg                                  272
```

<210> SEQ ID NO 22
<211> LENGTH: 176
<212> TYPE: DNA
<213> ORGANISM: Artificial

```
<220> FEATURE:
<223> OTHER INFORMATION: Synthetic promoter

<400> SEQUENCE: 22
ctagcgtccg ccctcaggaa gagggcggag gctcaccaag atttccaaac tctgtggttg      60
ccttgccaag atttccaaac tctgtggttg ccttgccaag atttccaaac tctgtggttg     120
ccttgtgagc ctccgccctc ttcctaagcg acttcctctt tccaggaggg cggacg         176

<210> SEQ ID NO 23
<211> LENGTH: 266
<212> TYPE: DNA
<213> ORGANISM: Artificial
<220> FEATURE:
<223> OTHER INFORMATION: Synthetic promoter

<400> SEQUENCE: 23
ctagcgaggg cggacaagcg acttcctctt tccagcagaa aaggagaagt aggagccaag      60
atttccaaac tctgtggttg ccttgaagcg acttcctctt tccagaagcg acttcctctt    120
tccagcagaa aaggagaagt aggagctcct acttctcctt ttctgccaag atttccaaac    180
tctgtggttg ccttgctcct acttctcctt ttctgcagaa aaggagaagt aggagctgga    240
aagaggaagt cgcttgaggg cggacg                                          266

<210> SEQ ID NO 24
<211> LENGTH: 276
<212> TYPE: DNA
<213> ORGANISM: Artificial
<220> FEATURE:
<223> OTHER INFORMATION: Synthetic promoter

<400> SEQUENCE: 24
ctagcgaggg cggaccagaa aaggagaagt aggagccaag atttccaaac tctgtggttg      60
ccttgccaag atttccaaac tctgtggttg ccttgcagaa aaggagaagt aggagaagcg    120
acttcctctt tccagaagcg acttcctctt tccagaggaa gagggcggag gctcacaagg    180
caaccacaga gtttggaaat cttggaagcg acttcctctt tccagcagaa aaggagaagt    240
aggagaagcg acttcctctt tccaggtccg ccctcg                               276

<210> SEQ ID NO 25
<211> LENGTH: 20
<212> TYPE: DNA
<213> ORGANISM: Artificial
<220> FEATURE:
<223> OTHER INFORMATION: Oligonucleotide primer

<400> SEQUENCE: 25
aagcgacttc ctctttccag                                                  20

<210> SEQ ID NO 26
<211> LENGTH: 19
<212> TYPE: DNA
<213> ORGANISM: Artificial
<220> FEATURE:
<223> OTHER INFORMATION: Oligonucleotide primer

<400> SEQUENCE: 26
ctcctacttc tcctttctg                                                   19

<210> SEQ ID NO 27
<211> LENGTH: 20
<212> TYPE: DNA
```

-continued

```
<213> ORGANISM: Artificial
<220> FEATURE:
<223> OTHER INFORMATION: Oligonucleotide primer

<400> SEQUENCE: 27
tgagcctccg ccctcttcct                                          20
```